(12) United States Patent
Zheng

(10) Patent No.: US 9,309,249 B2
(45) Date of Patent: Apr. 12, 2016

(54) ENTECAVIR SYNTHESIS METHOD AND INTERMEDIATE COMPOUND THEREOF

(75) Inventor: Zhiguo Zheng, Taizhou (CN)

(73) Assignee: Zhejiang Ausun Pharmaceutical Co., Ltd, Zhejiang (CN)

( * ) Notice: Subject to any disclaimer, the term of this patent is extended or adjusted under 35 U.S.C. 154(b) by 0 days.

(21) Appl. No.: 13/810,062

(22) PCT Filed: Jul. 15, 2011

(86) PCT No.: PCT/CN2011/077195
§ 371 (c)(1),
(2), (4) Date: Apr. 1, 2013

(87) PCT Pub. No.: WO2012/006964
PCT Pub. Date: Jan. 19, 2012

(65) Prior Publication Data
US 2013/0217879 A1   Aug. 22, 2013

(30) Foreign Application Priority Data

Jul. 15, 2010   (CN) .......................... 2010 1 0230153
Jul. 13, 2011   (CN) .......................... 2011 1 0196709

(51) Int. Cl.
| | | |
|---|---|---|
| C07D 473/02 | (2006.01) |
| C07D 473/18 | (2006.01) |
| C07C 41/26 | (2006.01) |
| C07C 67/29 | (2006.01) |
| C07C 67/293 | (2006.01) |
| C07C 69/76 | (2006.01) |
| C07C 69/78 | (2006.01) |
| C07F 7/18 | (2006.01) |
| C07D 473/40 | (2006.01) |
| C07C 41/18 | (2006.01) |
| C07D 319/08 | (2006.01) |
| C07D 309/12 | (2006.01) |

(52) U.S. Cl.
CPC .............. *C07D 473/18* (2013.01); *C07C 41/18* (2013.01); *C07C 41/26* (2013.01); *C07C 67/29* (2013.01); *C07C 67/293* (2013.01); *C07C 69/76* (2013.01); *C07C 69/78* (2013.01); *C07D 309/12* (2013.01); *C07D 319/08* (2013.01); *C07D 473/40* (2013.01); *C07F 7/184* (2013.01); *C07F 7/1824* (2013.01); *C07F 7/1892* (2013.01); *C07C 2101/08* (2013.01)

(58) Field of Classification Search
CPC ..................................................... C07D 473/02
See application file for complete search history.

(56) References Cited

U.S. PATENT DOCUMENTS

2011/0201809 A1*   8/2011   Hu et al. ....................... 544/276

FOREIGN PATENT DOCUMENTS

| CN | 1747959 A | 3/2006 |
| CN | 101130542 A | 2/2008 |
| CN | 101148450 A | 3/2008 |
| WO | 2010/074534 A2 | 7/2010 |

OTHER PUBLICATIONS

"Aprotic Solvents." Michigan State University. (c) Nov. 18, 2009. Available from: < http://web.archive.org/web/20091118204155/http://www.cem.msu.edu/~reusch/OrgPage/solvent.htm >.*

* cited by examiner

*Primary Examiner* — Noble Jarrell
*Assistant Examiner* — John S Kenyon
(74) *Attorney, Agent, or Firm* — Ladas & Parry LLP

(57) ABSTRACT

The present invention relates to a preparation method for a medicine and an intermediate compound thereof, specifically, relates to a preparation method for entecavir, an intermediate compound thereof, and a synthesis method for the intermediate compound.

27 Claims, No Drawings

ENTECAVIR SYNTHESIS METHOD AND INTERMEDIATE COMPOUND THEREOF

RELATED APPLICATION INFORMATION

This application is a 371 of International Application PCT/CN2011/077195 filed 15 Jul. 2011 entitled "Entecavir Synthesis Method And Intermediate Compound Thereof" which was published 19 Jan. 2012, with International Publication Number WO 2012/006964 A1, and which claims priority from Chinese Patent Applications Nos.: CN 201010230153.7 filed 15 Jul. 2010 and CN 201110196709.X filed 13 Jul. 2011, the contents of which are incorporated herein by reference.

FIELD OF TECHNOLOGY

The present invention relates to a method for preparation of a medicine and to intermediate compounds thereof, specifically, relates to a method for preparation of entecavir, to intermediate compounds thereof, and to a method for synthesis of the intermediate compounds.

BACKGROUND OF THE INVENTION

Entecavir, i.e., Compound 2-amino-1,9-dihydro-9-[(1S,3R,4S)-4-hydroxy-3-(hydroxymethyl)-2-methylene-cyclopentyl]-6H-purine-6-one as shown in Formula (1) below, is a new nucleoside type of anti-viral agent.

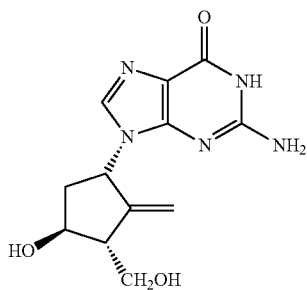

Entecavir is the third anti-HBV (Hepatitis B virus) drug which is marketed following Lamivudine and Adefovir Dipivoxil, and it has the highest anti-HBV activity among current anti-HBV drugs in the market. The anti-HBV effect of Entecavir is 100 times higher than Lamivudin, and is more than 30 times higher than Adefovir Dipivoxil. Moreover, its adverse effect is very low, its selection index is more than 8000, and it also has good therapeutic effect on Lamivudin-resistant HBV viruses. Thus, Entecavir provides theoretical possibility of healing Hepatitis B.

Up to now, the synthetic routes of preparing Entecavir mainly include the following routes.

Chinese patent ZL91110831.9 and International application WO98/09964 disclosed a method for preparation of Entecavir. Said method uses cyclopentadiene 8 as the starting material. Cyclopentadiene 8 is reacted with chloromethyl benzyl ether, followed by reacting with dipinene-borane complex ($Ipc_2BH$) prepared from (+)-α-pinene, to afford chiral Intermediate 9. Then epoxidation of Intermediate 9 by $t-BuO_2H$ under catalysis of acetylacetone vanadium oxide [$VO(acac)_2$] gives Intermediate 10. Reaction of Intermediate 10 with sodium hydride, tetrabutylammonium iodide and benzyl bromide affords Intermediate 11. Reaction of Intermediate 11 with lithium hydride and 6-benzyloxy-2-aminopurine 12 gives Intermediate 13. (mono-p-methoxy-triphenyl)-methyl chloride (MMTCl) is used to protect the amino of Intermediate 13 to afford Intermediate 14, which is subsequently oxidized with Dess-Martin reagent so as to oxidize hydroxy group to ketone group, thereby yielding Intermediate 15. Intermediate 15 is treated with Nysted reagent and titanium tetrachloride to perform methylenation, to give Intermediate 16. Then Intermediate 16 is reacted with hydrochloric acid to cleave the MMT group on the amino group and the benzyl group on the purine ring, to obtain Intermediate 17. Finally Intermediate 17 is treated with boron trichloride to cleave benzyl groups on the hydroxyl groups of the cycloalkyl. The method is shown as the following scheme.

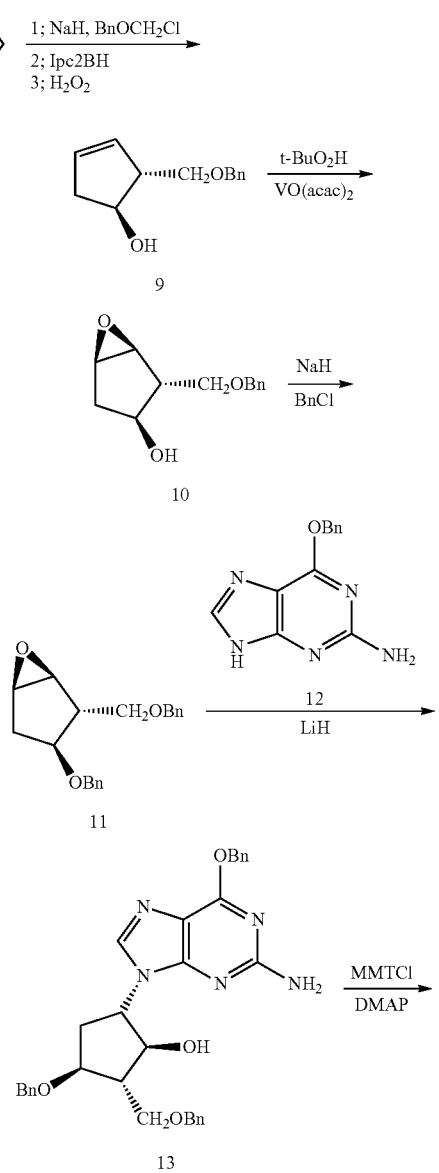

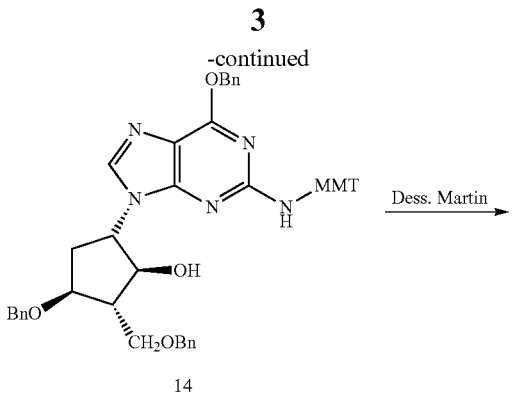
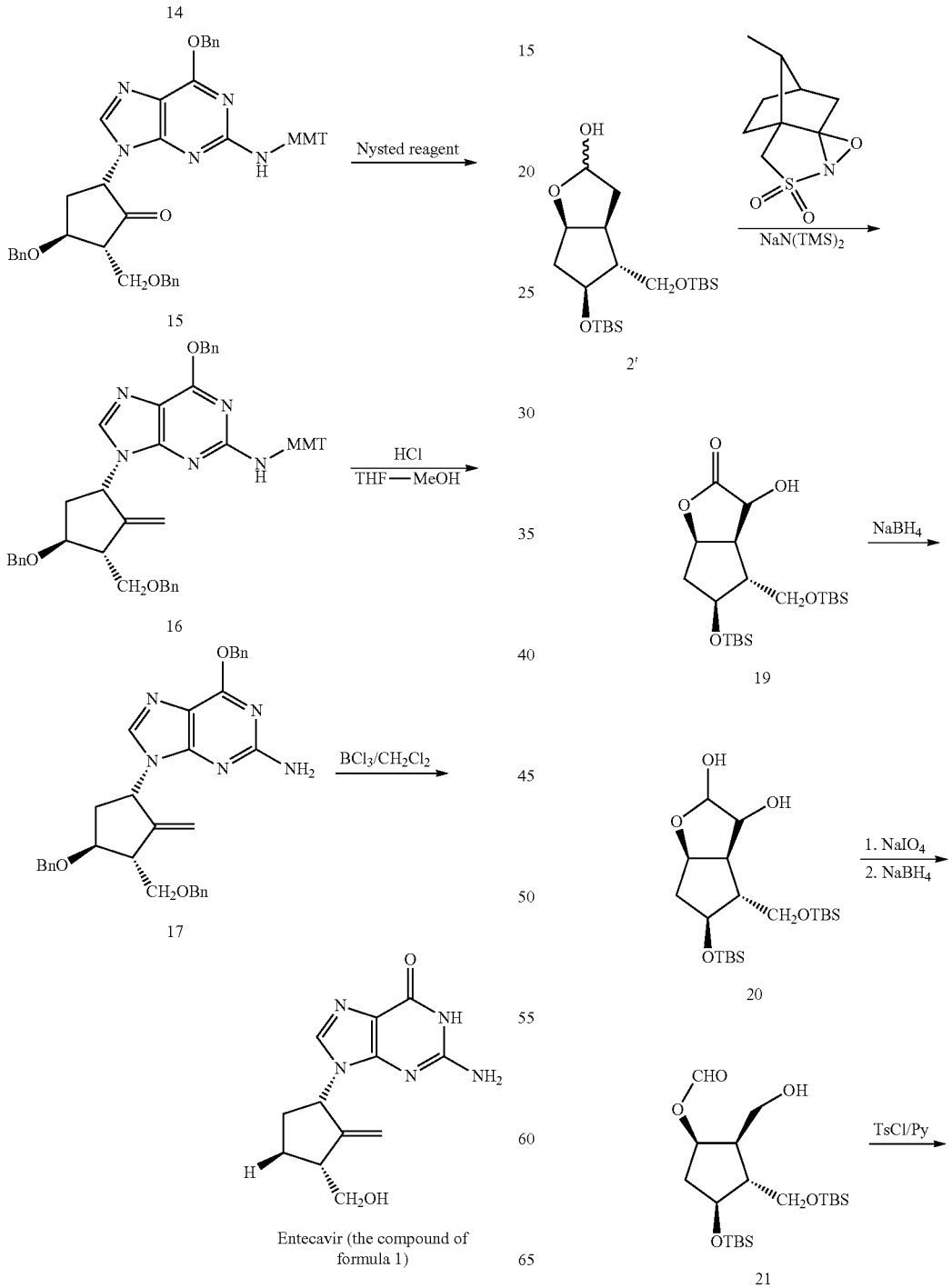

There are some problems in above preparation method. The starting materials include chiral boron reagent which is very expensive, removing benzyl in the last step utilizes hypertoxic boron trichloride, the synthetic steps of the Intermediates are difficult and need harsh conditions and high-quality equipments, and some reagents used in above method are expensive.

In addition, a patent application (Publication No. WO2004/052310A2) of Bristol Meyer Squibb Company disclosed a synthetic method using compound 2' as starting material, which is shown in the following scheme.

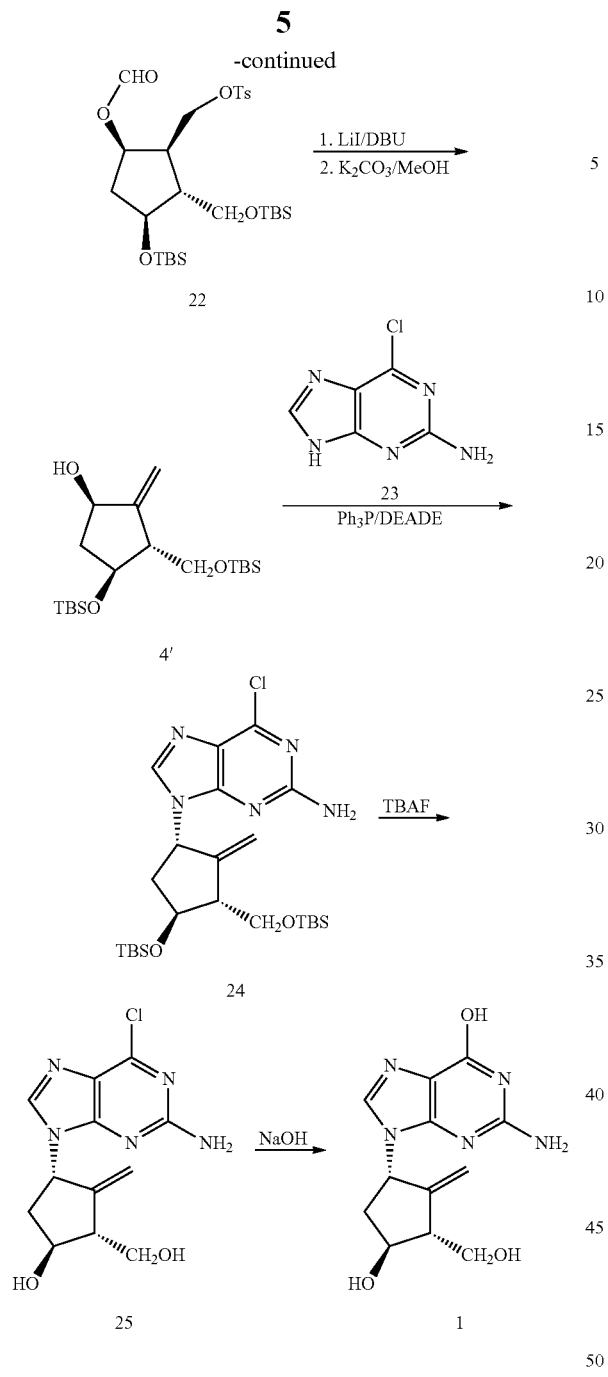

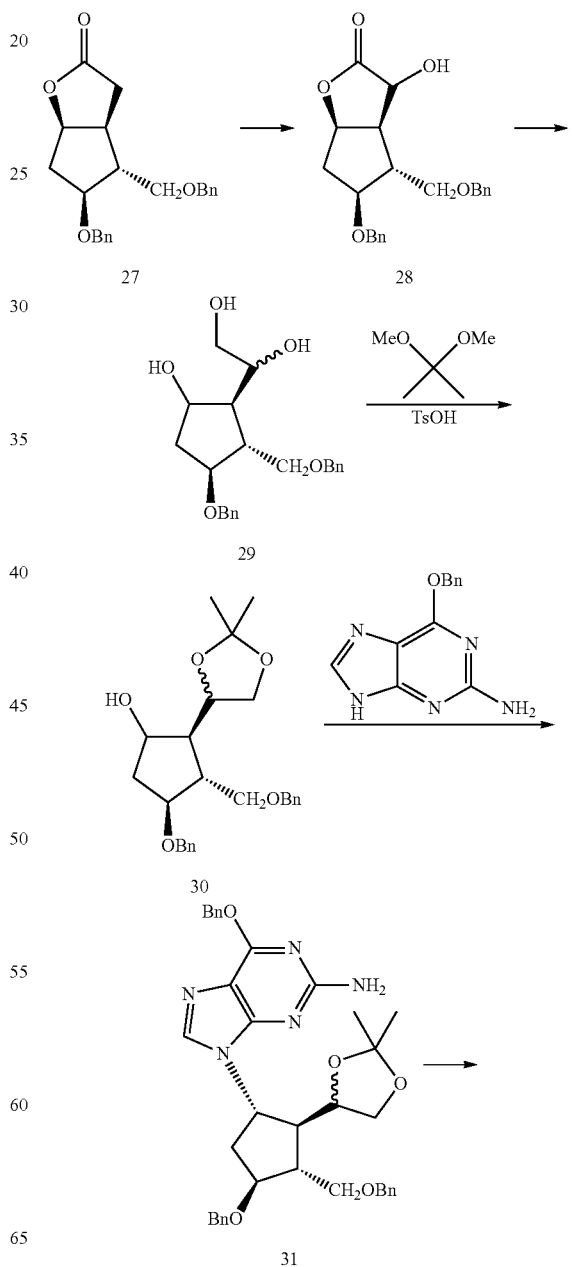

ing material is treated with iodophenyl acetate and iodine can be utilized to generate an iodide, and said iodide is subjected to elimination reaction followed by alcoholysis to prepare Intermediate 4, the patent application failed to provide specific experimental examples and experimental data to prove feasibility of said method.

When the inventor of the present invention used the reported conditions ($PhI(OAc)_2/I_2$, hv (Tetrahedron Letters, 1987, 28, 3397-3400)) according to above method of WO 2004/052310A2 to prepare Intermediate 4, he found the yield of said method was low, thus it is difficult to apply said method to industrial production.

Another method was disclosed in Chinese Chemical Letters, 2006, 17(7) 907-910 and Chinese patent application publication CN 1861602A, which is shown in the following scheme.

However, when the applicant used above method of WO2004/052310A2 to synthesize Entecavir, Mitsunobu reaction of 2-aminopurine compound 23 (in which the amino group was not protected) with Intermediate 4 as described in said method was found to have lower and instable yield. Moreover, the coupling reaction product 24 of said Mitsunobu reaction has similar polarity to triphenyl phosphine oxide generated from the reagent triphenylphosphine, thus it is difficult to isolate and purify the reaction product. Furthermore, the Intermediate 25 obtained by removing hydroxy-protecting group from the reaction product 24 has high water-solubility, thus it is difficult to obtain the Intermediate 25 by simple extraction and isolation, and its yield is low. Therefore, the method of WO2004/052310A2 was considered unsuitable to large-scale industrial production.

Furthermore, although above method also mentioned a photochemistry method in which compound 2' used as start-

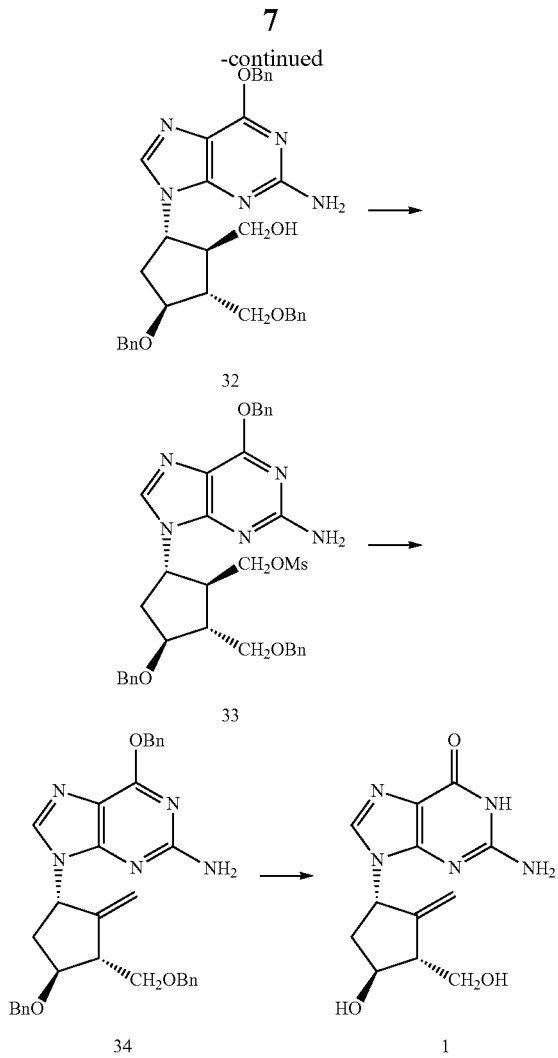

However, above method has long synthetic route and complicated operations, thus it is difficult to apply said method to industrial production.

Therefore, there is still a need for development of a new preparation method now, which can overcome above-mentioned problems and is convenient to use in industrial production.

Contents of the Invention

Throughout the description, the following terms have the meanings as indicated below.

The term "alkyl", whether it is used alone or in combination with other groups, represents a straight or branched monovalent saturated hydrocarbon group consisting of carbon atom and hydrogen atom. The term "$C_{1-6}$ alkyl" represents straight or branched alkyl having 1-6 carbon atoms, such as methyl, ethyl, n-propyl, isopropyl, n-butyl, sec-butyl, tert-butyl, and n-hexyl.

"Halo" or "Halogen" represents fluoro, chloro, bromo or iodo.

"Halo-alkyl" represents alkyl as defined above which is substituted with one or more halogens, e.g., trifluoromethyl.

The term "alkoxy", whether it is used alone or in combination with other groups, represents group R'—O—, wherein R' represents alkyl as defined above. "$C_{1-6}$ alkoxy" represents group R'—O—, wherein R' represents $C_{1-6}$ alkyl as defined above.

"Halo-alkoxy" represents alkoxy as defined above which is substituted with one or more halogens, e.g., trifluoromethoxy.

"Aryl" represents monocyclic or fused bicyclic aromatic ring containing carbon atoms. "$C_{5-10}$ aryl" represents aryl having 5-10 carbon atoms. For example, $C_{5-10}$ aryl may be phenyl or naphthyl.

"Aralkyl" represents alkyl as defined above which is substituted with aryl as defined above.

"Aralkoxy" represents alkoxy as defined above which is substituted with aryl as defined above.

"Acyl" represents group —CO—R, wherein R is alkyl, aryl or aralkyl as defined above.

The aryl as mentioned above, whether it is used as itself per se or used as a part of other groups such as aralkyl and aralkoxy, may be optionally substituted with one or more substituents. In the case of substituted aryl, the substituents thereon are preferably selected from $C_{1-6}$ alkyl, $C_{1-6}$ alkoxy, halo, aryl and nitro, more preferably selected from methoxy, ethoxy, halo, phenyl and nitro.

The present invention provides a novel method for synthesis of Entecavir, which involves less reaction steps, is easy to manipulate and is able to improve the yield and reduce the cost.

In one aspect, the present invention relates to a method for synthesis of Entecavir (the compound of formula 1) using 2-protected amino-6-substituted purine compound as starting material, comprising the following steps:

c) Mitsunobu reaction of compound 4 with 2-protected amino-6-substituted purine compound 5 to give the coupling reaction product 6

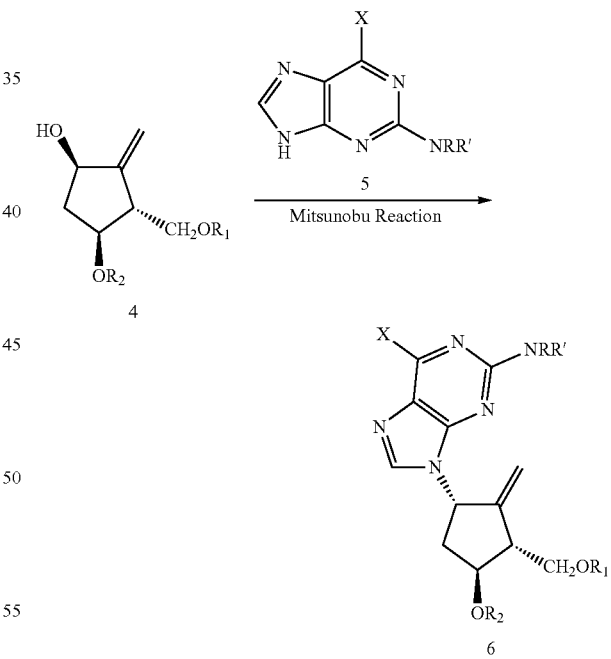

wherein $R_1$ and $R_2$, which are the same or different, are independently selected from hydroxy-protecting groups of the following Groups (i) to (iii):

(i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si; or (iii) $R_1$ and $R_2$ together with the five-member carbocycle to which they are attached form one of the following fused ring systems:

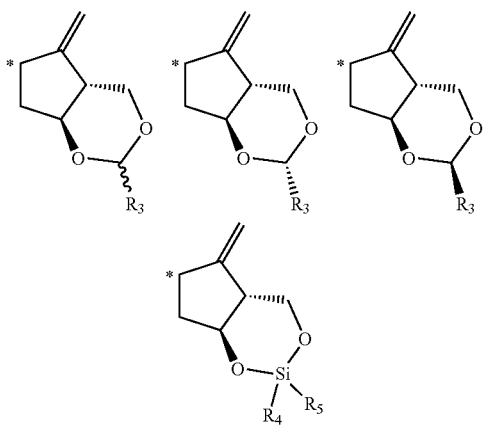

wherein $R_3$ is hydrogen atom, $C_{1-6}$ alkyl, phenyl or substituted phenyl in which the substituent on said phenyl is preferably selected from methoxy, ethoxy, halo, phenyl and nitro; $R_4$ and $R_5$, which are the same or different, are independently selected from $C_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

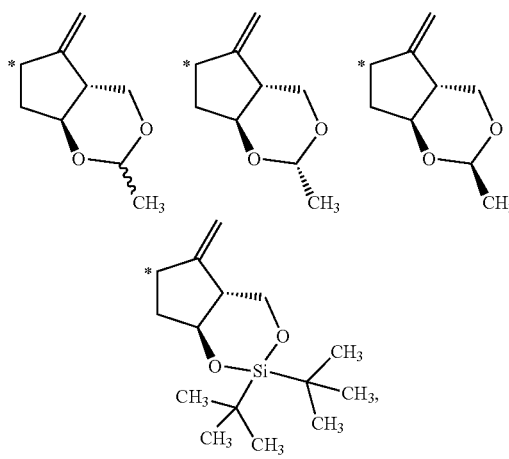

R and R', which are the same or different, are independently selected from hydrogen, alkoxycarbonyl or aralkoxycarbonyl, such as $C_{1-6}$ alkoxycarbonyl or $C_{5-10}$ aralkoxycarbonyl, preferably tert-butyloxycarbonyl, provided that R and R' are not both hydrogen; X is halo, alkoxy, halo-alkoxy or aralkoxy, such as $C_{1-6}$ alkoxy, halo-$C_{1-6}$ alkoxy or $C_{5-10}$ aralkoxy, preferably chloro, methoxy, benzyloxy, tert-butyloxy, particularly preferably chloro;

d) when $R_1$ and $R_2$ are both acyl protective groups or neither of them is acyl protective group, removing hydroxy-protecting groups from compound 6, to give compound 7

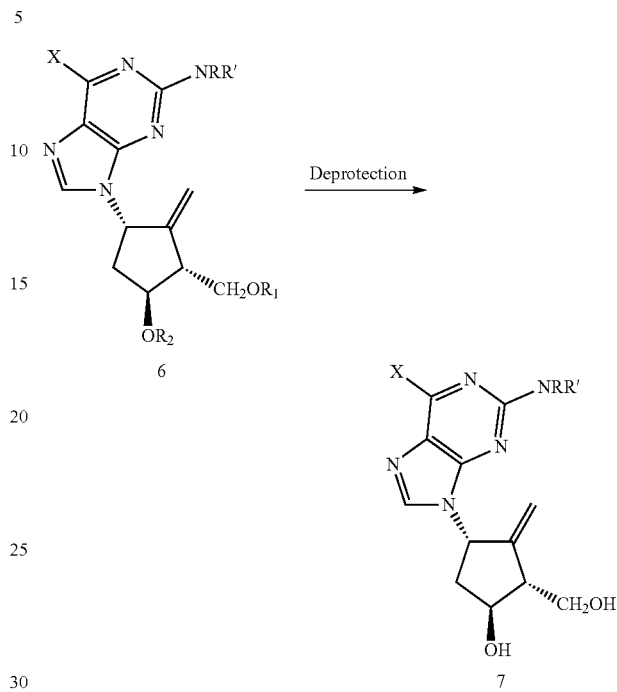

wherein X, $R_1$, $R_2$, R and R' are defined as above;

e) hydrolysis of compound 7 to give the compound of formula 1 (Entecavir)

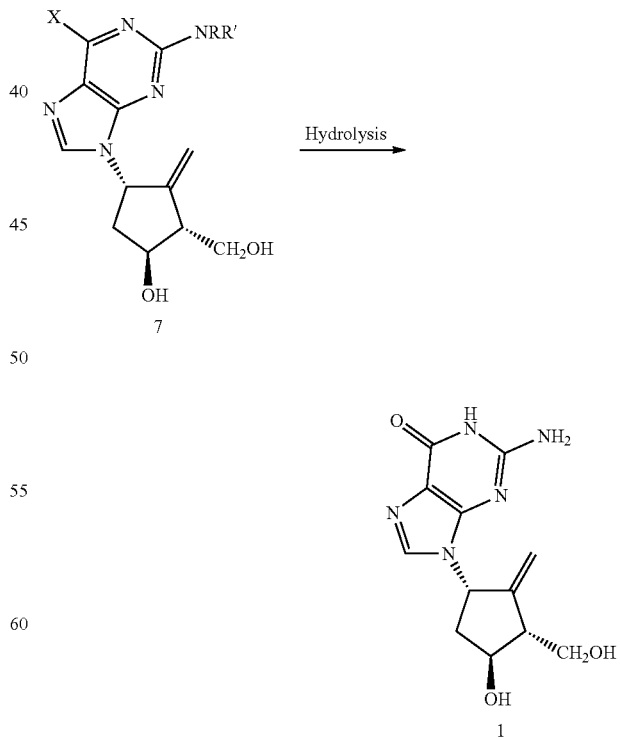

wherein X, R and R' are defined as above; or d') when neither of $R_1$ and $R_2$ is acyl protective group, deprotecting compound 6 while hydrolysis in one-pot manner, to directly yield the compound of formula 1

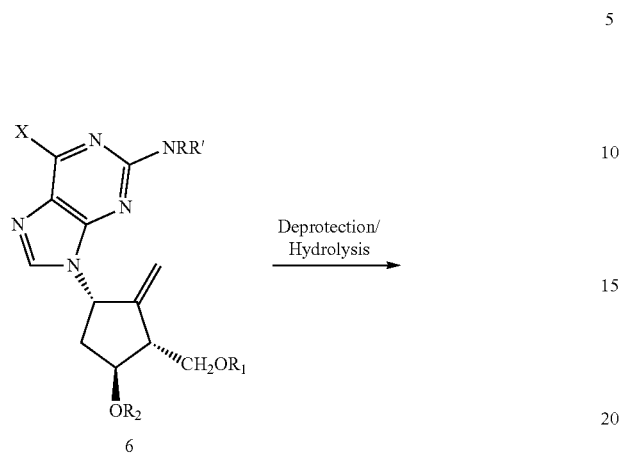

6

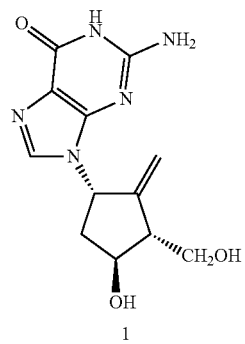

1 wherein X, $R_1$, $R_2$, R and R' are defined as above, or d") when either of $R_1$ and $R_2$ is acyl protective group, such as benzoyl, benzoyl in which the phenyl ring bears substituent(s), or biphenylformyl, deprotecting compound 6 to give compound 8 or 9 which is then hydrolyzed to give compound 1 or is converted to compound 7 followed by hydrolysis to give compound 1,

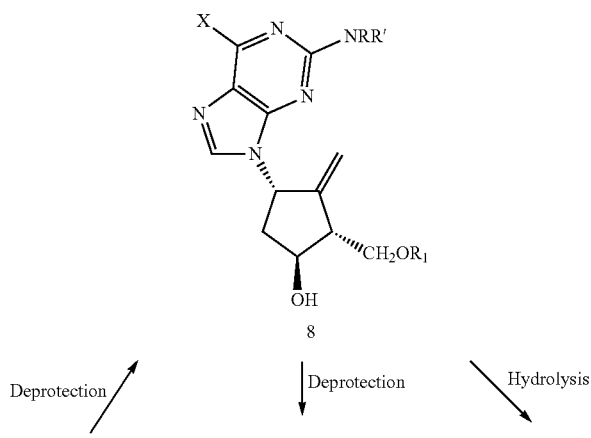

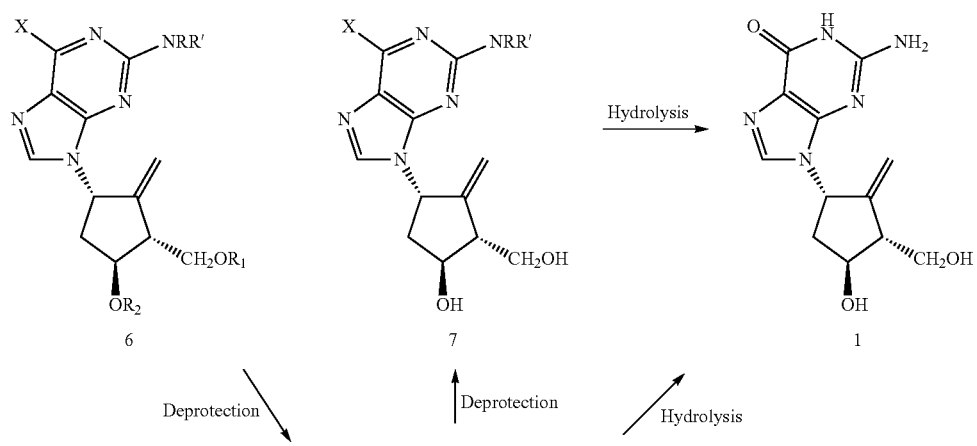

-continued

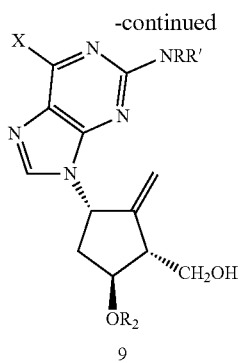

9 wherein X, $R_1$, $R_2$, R and R' are defined as above.

In above step c), reaction of compound 4 with compound 5 is performed in the presence of Mitsunobu reaction reagent, such as $Ph_3P/EtO_2CN=NCO_2Et$ or $Ph_3P/i-PrO_2CN=NCO_2i-Pr$, in a non-protonic solvent such as aromatic hydrocarbons, halogenated aromatic hydrocarbons, halogenated hydrocarbons or ethers, e.g., THF.

In above step d), deprotection of compound 6 is performed in the presence of an acid (e.g., when $R_1$ and $R_2$ are both silyl protective groups) or a base (e.g., when $R_1$ and $R_2$ are both acyl protective groups), for example, in the presence of hydrohalogen acid such as hydrochloric acid or hydrogen fluoride, formic acid or a quaternary ammonium salt containing fluorinion, for example tetra-butylammonium fluoride (TBAF) or pyridinium hydrofluoride, or potassium carbonate or an alkoxide such as sodium alkoxide. Preferably, the reaction is performed in the presence of tetra-butylammonium fluoride (TBAF) or hydrochloric acid. Said reaction is performed in an appropriate solvent or a mixture of said solvent and water, such as tetrahydrofuran, dichloromethane, methanol or ethanol, or any combination thereof.

In above step e), hydrolysis of compound 7 is performed under acid or basic condition, preferably in the presence of hydrochloric acid or formic acid, in water or in a mixture of water and organic solvents, such as a mixture of tetrahydrofuran or ethanol and water, more preferably in the presence of hydrochloric acid in a solvent of tetrahydrofuran.

In above step d'), deprotection and hydrolysis of compound 6 may be performed in the presence of hydrohalogen acid, such as diluted hydrochloric acid, for example 0.1 N-3 N of diluted hydrochloric acid, in an appropriate organic solvent or a mixture of said solvent and water, such as methanol, ethanol or tetrahydrofuran, or a mixture of said solvent and water.

In above step d"), compound 8 or 9 derived from compound 6 may be used to directly give compound 1, or may be used to generate compound 7 that is then used to obtain compound 1, which depends on the sequence of cleaving silyl protective groups and cleaving acyl protective groups. For acyl protective groups, they are cleaved by alkaline hydrolysis, for example, the reaction is performed in the presence of a base, such as potassium carbonate, alkali metal hydroxide, an alkoxide e.g., sodium alkoxide.

Thus, in a preferred embodiment, Entecavir of formula (1) is prepared by the process comprising:

c) reacting compound 4 with 2-protected amino-6-substituted purine compound 5 in the presence of $Ph_3P/EtO_2CN=NCO_2Et$ or $Ph_3P/i-PrO_2CN=NCO_2i-Pr$, in a non-protonic solvent such as aromatic hydrocarbons, halogenated aromatic hydrocarbons, halogenated hydrocarbons or ethers, e.g., THF, to give the coupling reaction product 6;

d) removing hydroxy-protecting groups from compound 6, in the presence of tetrabutylammonium fluoride (TBAF) or hydrochloric acid, to give compound 7; and e) hydrolysis of compound 7 in the presence of hydrochloric acid, in tetrahydrofuran, to give the compound of formula 1.

In above steps c) to e), depending on the reaction condition used, reaction time may be from several minutes to several days, such as from 30 minutes to 14 days; reaction temperature may be from about −78° C. to reflux temperature of the solvent used, such as from 0° C. to 150° C., especially from room temperature to reflux temperature of the solvent used.

The applicant found that, in above step c), when using 2-protected amino-6-substituted purine compound as the starting material, the reaction rate of said Mitsunobu reaction can be accelerated and the yield is significantly improved, thereby rendering the total yield of preparation of Entecavir greatly increased. Without being bound by any theories, it is believed that the reason for accelerating the reaction rate and improving the yield is that use of 2-protected amino-6-substituted purine compound 5 overcomes the problem of poor solubility of unprotected amino-purine compound in the reaction solvent, and improves the physico-chemical properties of coupling reaction product obtained, resulting in the subsequent reactions and purification of the intermediate compounds are easy to be handled. The 2-protected amino-6-substituted purine compound of the invention may be prepared according to the synthetic method of 2-tert-butyloxycarbonylamino-6-chloro-guanine as described in the literature (*J. Org. Chem.* 2000, 65, 7697-7699), using 2-amino-6-substituted guanine as the starting material.

In above methods, the intermediate compounds of formulae 6 and 7 are novel compounds.

Thus, in one aspect, the present invention also relates to the compounds of the formula below:

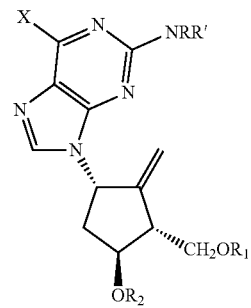

wherein

R$_1$ and R$_2$, which are the same or different, are independently selected from hydrogen or hydroxy-protecting groups of the following Groups (i) to (iii):

(i) R$_1$ and R$_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) R$_1$ and R$_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that R$_1$ and R$_2$ are not both t-BuMe$_2$Si; or (iii) R$_1$ and R$_2$ together with the five-member carbocycle to which they are attached form one of the following fused ring systems:

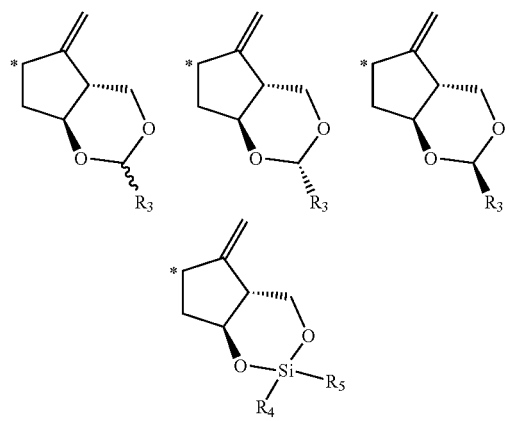

wherein R$_3$ is hydrogen atom, C$_{1-6}$ alkyl, phenyl or substituted phenyl in which the substituent on said phenyl is preferably selected from methoxy, ethoxy, halo, phenyl and nitro; R$_4$ and R$_5$, which are the same or different, are independently selected from C$_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

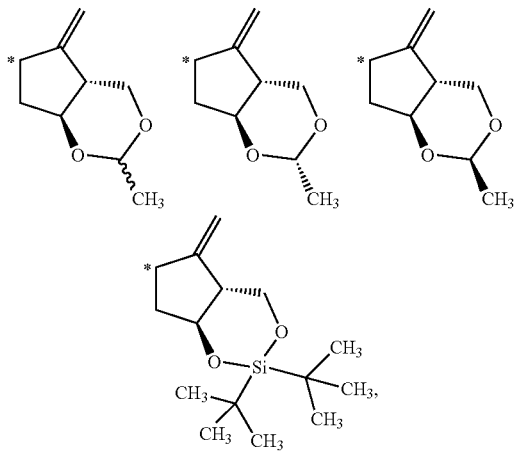

R and R', which are the same or different, are independently selected from hydrogen, alkoxycarbonyl or aralkoxycarbonyl, such as C$_{1-6}$ alkoxycarbonyl or C$_{5-10}$ aralkoxycarbonyl, preferably tert-butyloxycarbonyl, provided that R and R' are not both hydrogen; X is halo, alkoxy, halo-alkoxy or aralkoxy, such as C$_{1-6}$ alkoxy, halo-C$_{1-6}$ alkoxy or C$_{5-10}$ aralkoxy, preferably chloro, methoxy, benzyloxy, tert-butyloxy, particularly preferably chloro.

In the compounds of above formula, the compounds in the following table are particularly preferred.

| Compound name | Structure |
|---|---|
| 9-[(1S,3R,4S)-4-tert-butyldimethylsilyloxy-3-(tert-butyldimethylsilyloxymethyl)-2-methylene-cyclopentyl]-6-chloro-9H-purine-2-carbamic acid tert-butyl ester; | 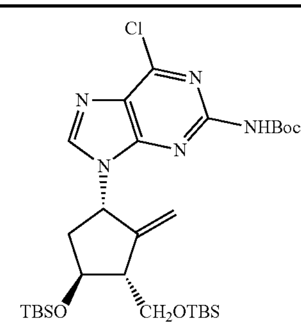 |
| 9-[(1S,3R,4S)-4-tert-butyldimethylsilyloxy-3-(tert-butyldimethylsilyloxymethyl)-2-methylene-cyclopentyl]-6-chloro-N-(tert-butyloxycarbonyl)-9H-purine-2-carbamic acid tert-butyl ester; | 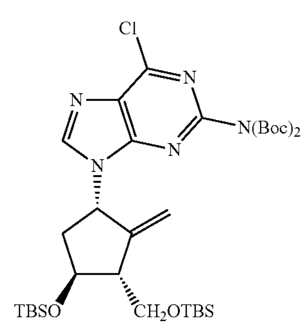 |

| Compound name | Structure |
|---|---|
| 9-[(1S,3R,4S)-4-tert-butyldimethylsilyloxy-3-(tert-butyldimethylsilyloxymethyl)-2-methylene-cyclopentyl]-6-methoxy-9H-purine-2-carbamic acid tert-butyl ester; | 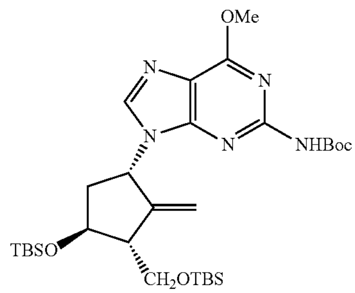 |
| 6-benzyloxy-9-[(1S,3R,4S)-4-tert-butyldimethylsilyloxy-3-(tert-butyldimethylsilyloxymethyl)-2-methylene-cyclopentyl]-9H-purine-2-carbamic acid tert-butyl ester; | 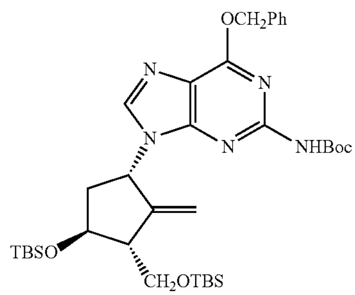 |
| 6-tert-butyloxy-9-[(1S,3R,4S)-4-tert-butyldimethylsilyloxy-3-(tert-butyldimethylsilyloxymethyl)-2-methylene-cyclopentyl]-9H-purine-2-carbamic acid tert-butyl ester; | 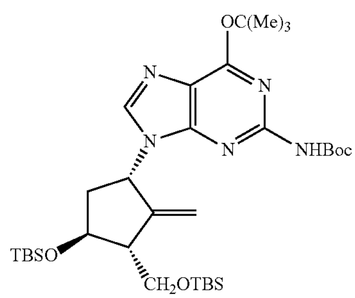 |
| 9-[(1S,3R,4S)-4-benzyloxy-3-(benzyloxymethyl)-2-methylene-cyclopentyl]-6-chloro-9H-purine-2-carbamic acid tert-butyl ester; | 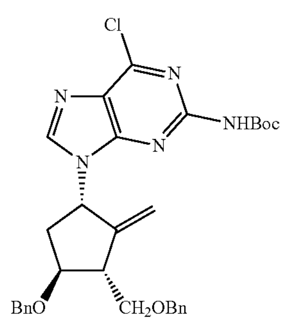 |
| 6-chloro-9-[(1S,3R,4S)-4-hydroxy-3-hydroxymethyl-2-methylene-cyclopentyl]-9H-purine-2-carbamic acid tert-butyl ester; | 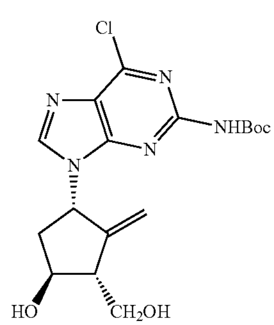 [SMILES: C=C1[C@H](CO)[C@@H](O)C[C@@H]1n1cnc2c(Cl)nc(NC(=O)OC(C)(C)C)nc21] |

-continued

| Compound name | Structure |
|---|---|
| 6-chloro-9-[(1S,3R,4S)-4-hydroxy-3-hydroxymethyl-2-methylene-cyclopentyl]-N-(tert-butyloxycarbonyl)-9H-purine-2-carbamic acid tert-butyl ester; | 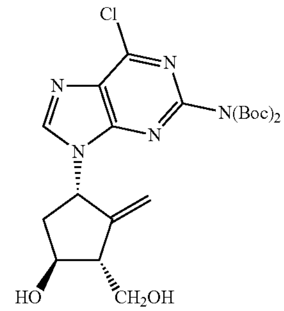 |
| 9-[(1S,3R,4S)-4-hydroxy-3-hydroxymethyl-2-methylene-cyclopentyl]-6-methoxy-9H-purine-2-carbamic acid tert-butyl ester; | 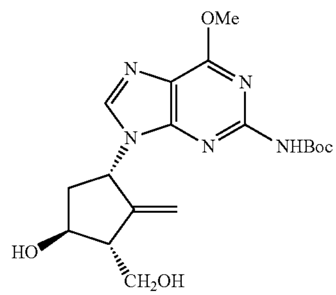 [SMILES: C=C1[C@H](CO)[C@@H](O)C[C@@H]1n1cnc2c(OC)nc(NC(=O)OC(C)(C)C)nc21] |
| 6-benzyloxy-9-[(1S,3R,4S)-4-hydroxy-3-hydroxymethyl-2-methylene-cyclopentyl]-9H-purine-2-carbamic acid tert-butyl ester; | 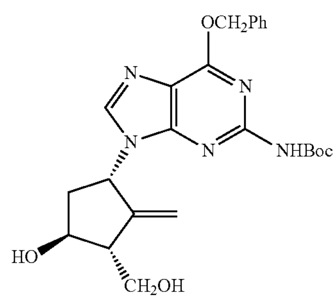 |
| 6-tert-butyloxy-9-[(1S,3R,4S)-4-hydroxy-3-hydroxymethyl-2-methylene-cyclopentyl]-9H-purine-2-carbamic acid tert-butyl ester; and | 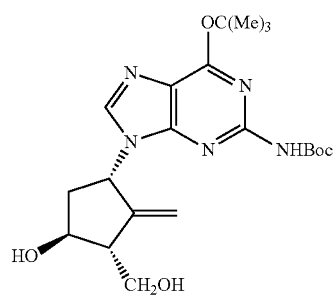 |
| 9-[(1S,3R,4S)-3-(tert-butyldimethylsilyloxymethyl)-4-(tetrahydropyran-2-yloxy)-2-methylene-cyclopentyl]-6-chloro-9H-purine-2-carbamic acid tert-butyl ester | 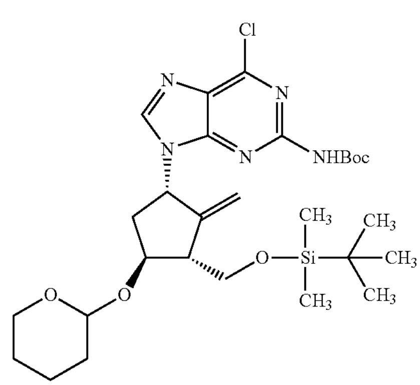 [SMILES: C=C1[C@H](CO[Si](C)(C)C(C)(C)C)[C@@H](OC2CCCCO2)C[C@@H]1n1cnc2c(Cl)nc(NC(=O)OC(C)(C)C)nc21] |

| Compound name | Structure |
|---|---|
| 9-[(1S,3R,4S)-3-(tert-butyldimethylsilyloxymethyl)-4-(tert-butyldiphenylsilyloxy)-2-methylene-cyclopentyl]-6-chloro-9H-purine-2-carbamic acid tert-butyl ester; | 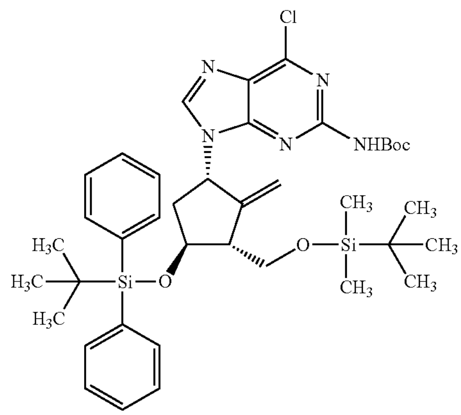 [SMILES: C=C1[C@H](CO[Si](C)(C)C(C)(C)C)[C@@H](O[Si](c2ccccc2)(c2ccccc2)C(C)(C)C)C[C@@H]1n1cnc2c(Cl)nc(NC(=O)OC(C)(C)C)nc21] |
| 9-[(1S,3R,4S)-3-(tert-butyldimethylsilyloxymethyl)-4-(biphenyl-4-formyloxy)-2-methylene-cyclopentyl]-6-chloro-9H-purine-2-carbamic acid tert-butyl ester; | 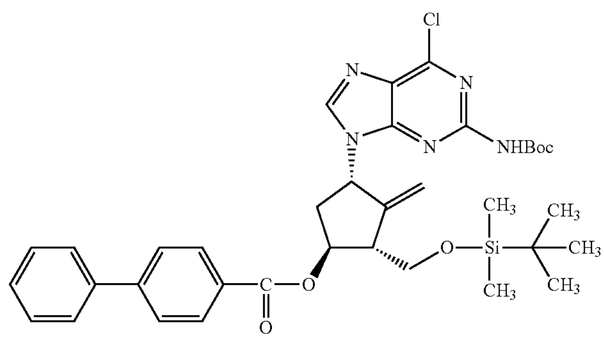 [SMILES: C=C1[C@H](CO[Si](C)(C)C(C)(C)C)[C@@H](OC(=O)c2ccc(-c3ccccc3)cc2)C[C@@H]1n1cnc2c(Cl)nc(NC(=O)OC(C)(C)C)nc21] |
| 9-[(1S,3R,4S)-3-(tert-butyldimethylsilyloxymethyl)-4-benzoyloxy-2-methylene-cyclopentyl]-6-chloro-9H-purine-2-carbamic acid tert-butyl ester; | 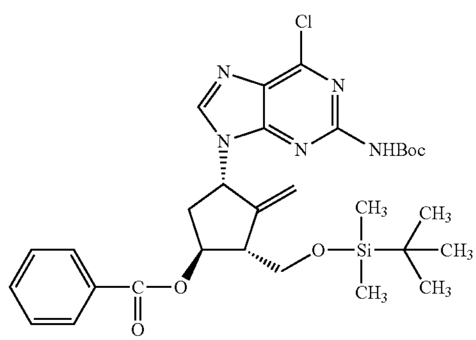 [SMILES: C=C1[C@H](CO[Si](C)(C)C(C)(C)C)[C@@H](OC(=O)c2ccccc2)C[C@@H]1n1cnc2c(Cl)nc(NC(=O)OC(C)(C)C)nc21] |
| 9-[(1S,3R,4S)-3-(tert-butyldiphenylsilyloxymethyl)-4-(tetrahydropyran-2-yloxy)-2-methylene-cyclopentyl]-6-chloro-9H-purine-2-carbamic acid tert-butyl ester; | 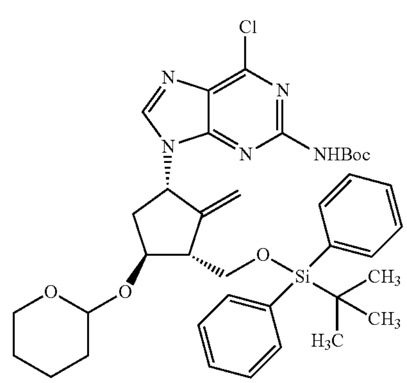 [SMILES: C=C1[C@H](CO[Si](c2ccccc2)(c2ccccc2)C(C)(C)C)[C@@H](OC2CCCCO2)C[C@@H]1n1cnc2c(Cl)nc(NC(=O)OC(C)(C)C)nc21] |

| Compound name | Structure |
|---|---|
| 9-[(1S,3R,4S)-4-tert-butyldimethylsilyloxy-3-(tert-butyldiphenylsilyloxymethyl)-2-methylene-cyclopentyl]-6-chloro-9H-purine-2-carbamic acid tert-butyl ester; | 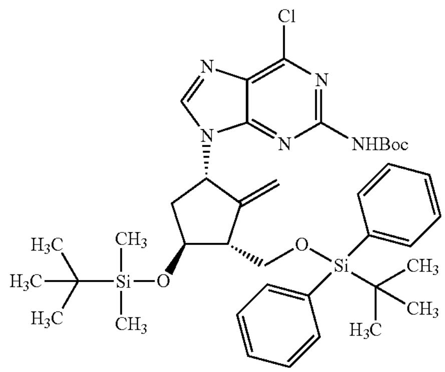 [SMILES: C=C1[C@H](CO[Si](c2ccccc2)(c2ccccc2)C(C)(C)C)[C@@H](O[Si](C)(C)C(C)(C)C)C[C@@H]1n1cnc2c(Cl)nc(NC(=O)OC(C)(C)C)nc21] |
| 9-[(1S,3R,4S)-4-(biphenyl-4-formyloxy)-3-(tert-butyldiphenylsilyloxymethyl)-2-methylene-cyclopentyl]-6-chloro-9H-purine-2-carbamic acid tert-butyl ester; | 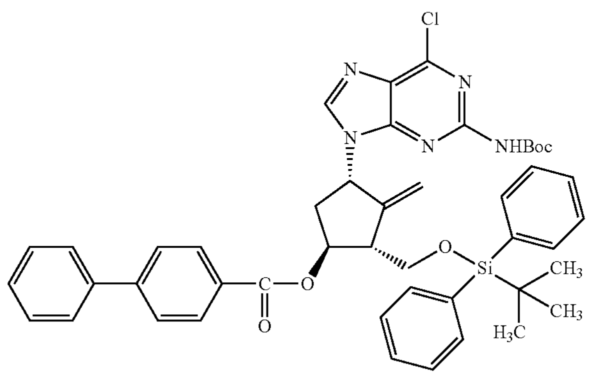 [SMILES: C=C1[C@H](CO[Si](c2ccccc2)(c2ccccc2)C(C)(C)C)[C@@H](OC(=O)c2ccc(-c3ccccc3)cc2)C[C@@H]1n1cnc2c(Cl)nc(NC(=O)OC(C)(C)C)nc21] |
| 9-[(1S,3R,4S)-4-(tert-butyldiphenylsilyloxy)-3-(tert-butyldiphenylsilyloxymethyl)-2-methylene-cyclopentyl]-6-chloro-9H-purine-2-carbamic acid tert-butyl ester; | 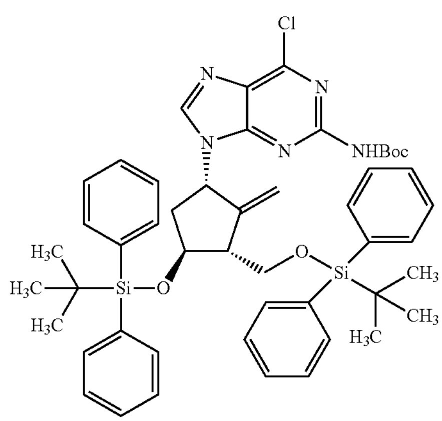 [SMILES: C=C1[C@H](CO[Si](c2ccccc2)(c2ccccc2)C(C)(C)C)[C@@H](O[Si](c2ccccc2)(c2ccccc2)C(C)(C)C)C[C@@H]1n1cnc2c(Cl)nc(NC(=O)OC(C)(C)C)nc21] |
| 9-[(1S,3R,4S)-4-benzoyloxy-3-(tert-butyldiphenylsilyloxymethyl)-2-methylene-cyclopentyl]-6-chloro-9H-purine-2-carbamic acid tert-butyl ester; | 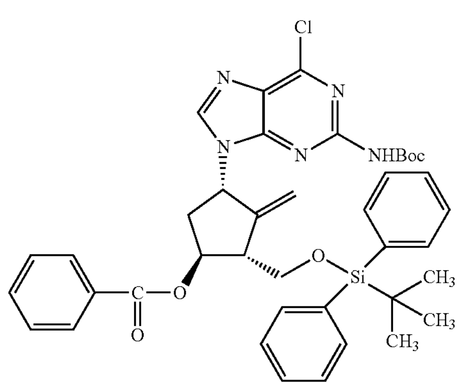 [SMILES: C=C1[C@H](CO[Si](c2ccccc2)(c2ccccc2)C(C)(C)C)[C@@H](OC(=O)c2ccccc2)C[C@@H]1n1cnc2c(Cl)nc(NC(=O)OC(C)(C)C)nc21] |

-continued

| Compound name | Structure |
|---|---|
| 9-[(1S,3R,4S)-4-benzoyloxy-3-(benzoyloxymethyl)-2-methylene-cyclopentyl]-6-chloro-9H-purine-2-carbamic acid tert-butyl ester; | 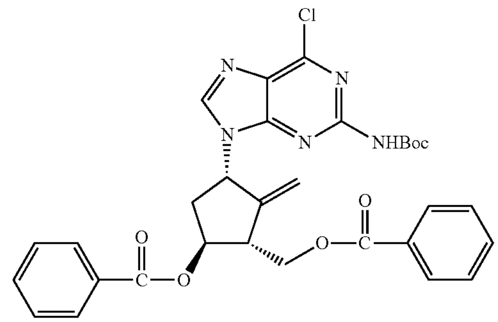 [SMILES: C=C1[C@H](COC(=O)c2ccccc2)[C@@H](OC(=O)c2ccccc2)C[C@@H]1n1cnc2c(Cl)nc(NC(=O)OC(C)(C)C)nc21] |
| 9-[(1S,3R,4S)-4-(tetrahydropyran-2-yloxy)-3-(benzoyloxymethyl)-2-methylene-cyclopentyl]-6-chloro-9H-purine-2-carbamic acid tert-butyl ester; | 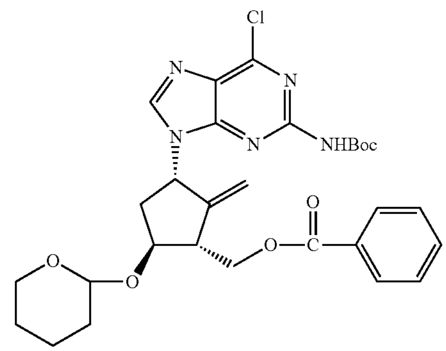 [SMILES: C=C1[C@H](COC(=O)c2ccccc2)[C@@H](OC2CCCCO2)C[C@@H]1n1cnc2c(Cl)nc(NC(=O)OC(C)(C)C)nc21] |
| 9-[(1S,3R,4S)-4-tert-butyldimethylsilyloxy-3-(benzoyloxymethyl)-2-methylene-cyclopentyl]-6-chloro-9H-purine-2-carbamic acid tert-butyl ester; | 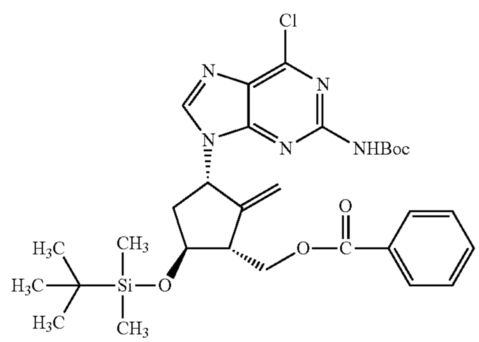 [SMILES: C=C1[C@H](COC(=O)c2ccccc2)[C@@H](O[Si](C)(C)C(C)(C)C)C[C@@H]1n1cnc2c(Cl)nc(NC(=O)OC(C)(C)C)nc21] |
| 9-[(1S,3R,4S)-4-(tert-butyldiphenylsilyloxy)-3-(benzoyloxymethyl)-2-methylene-cyclopentyl]-6-chloro-9H-purine-2-carbamic acid tert-butyl ester; | 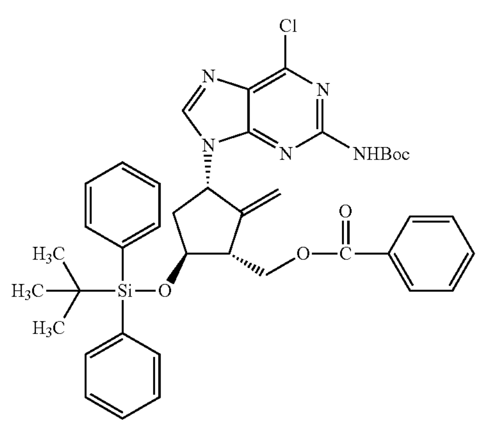 [SMILES: C=C1[C@H](COC(=O)c2ccccc2)[C@@H](O[Si](c2ccccc2)(c2ccccc2)C(C)(C)C)C[C@@H]1n1cnc2c(Cl)nc(NC(=O)OC(C)(C)C)nc21] |

| Compound name | Structure |
|---|---|
| 9-[(1S,3R,4S)-4-(biphenyl-4-formyloxy)-3-(benzoyloxymethyl)-2-methylene-cyclopentyl]-6-chloro-9H-purine-2-carbamic acid tert-butyl ester; | 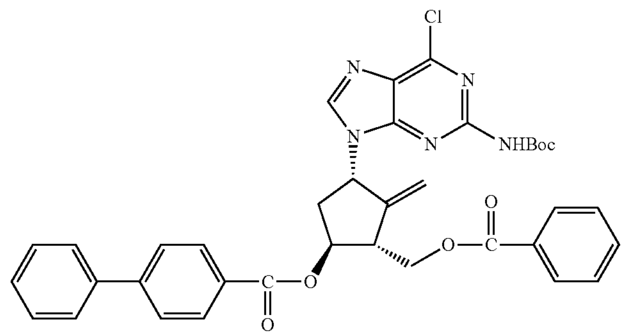 [SMILES: C=C1[C@H](COC(=O)c2ccccc2)[C@@H](OC(=O)c2ccc(-c3ccccc3)cc2)C[C@@H]1n1cnc2c(Cl)nc(NC(=O)OC(C)(C)C)nc21] |
| 9-[(1S,3R,4S)-4-benzoyloxy-3-(biphenyl-4-formyloxymethyl)-2-methylene-cyclopentyl]-6-chloro-9H-purine-2-carbamic acid tert-butyl ester; | 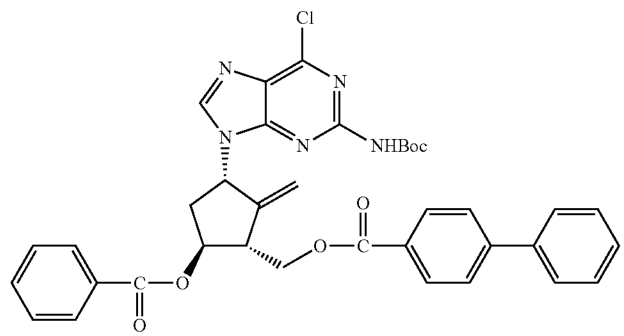 [SMILES: C=C1[C@H](COC(=O)c2ccc(-c3ccccc3)cc2)[C@@H](OC(=O)c2ccccc2)C[C@@H]1n1cnc2c(Cl)nc(NC(=O)OC(C)(C)C)nc21] |
| 9-[(1S,3R,4S)-4-(tetrahydropyran-2-yloxy)-3-(biphenyl-4-formyloxymethyl)-2-methylene-cyclopentyl]-6-chloro-9H-purine-2-carbamic acid tert-butyl ester; | 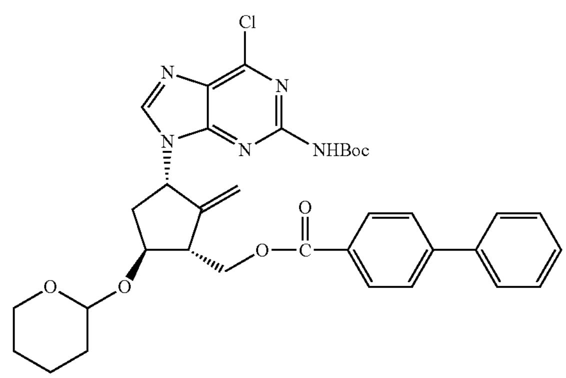 [SMILES: C=C1[C@H](COC(=O)c2ccc(-c3ccccc3)cc2)[C@@H](OC2CCCCO2)C[C@@H]1n1cnc2c(Cl)nc(NC(=O)OC(C)(C)C)nc21] |
| 9-[(1S,3R,4S)-4-tert-butyldimethylsilyloxy-3-(biphenyl-4-formyloxymethyl)-2-methylene-cyclopentyl]-6-chloro-9H-purine-2-carbamic acid tert-butyl ester; | 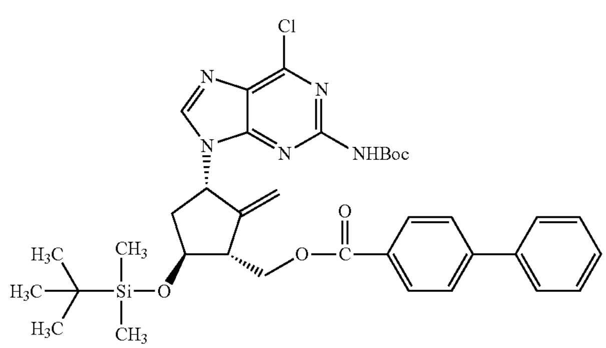 [SMILES: C=C1[C@H](COC(=O)c2ccc(-c3ccccc3)cc2)[C@@H](O[Si](C)(C)C(C)(C)C)C[C@@H]1n1cnc2c(Cl)nc(NC(=O)OC(C)(C)C)nc21] |

| Compound name | Structure |
|---|---|
| 9-[(1S,3R,4S)-4-(tert-butyldiphenylsilyloxy)-3-(biphenyl-4-formyloxymethyl)-2-methylene-cyclopentyl]-6-chloro-9H-purine-2-carbamic acid tert-butyl ester; | 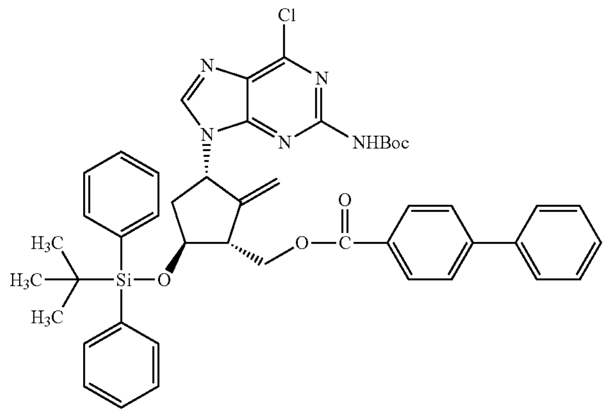 [SMILES: C=C1[C@H](COC(=O)c2ccc(-c3ccccc3)cc2)[C@@H](O[Si](c2ccccc2)(c2ccccc2)C(C)(C)C)C[C@@H]1n1cnc2c(Cl)nc(NC(=O)OC(C)(C)C)nc21] |
| 9-[(1S,3R,4S)-4-(biphenyl-4-formyloxy)-3-(tetrahydropyran-2-yloxymethyl)-2-methylene-cyclopentyl]-6-chloro-9H-purine-2-carbamic acid tert-butyl ester; | 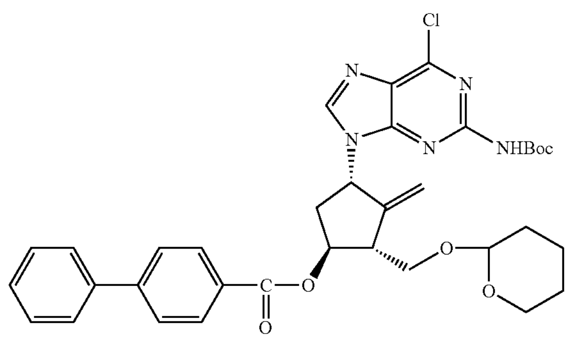 [SMILES: C=C1[C@H](COC2CCCCO2)[C@@H](OC(=O)c2ccc(-c3ccccc3)cc2)C[C@@H]1n1cnc2c(Cl)nc(NC(=O)OC(C)(C)C)nc21] |
| 9-[(1S,3R,4S)-4-tert-butyldimethylsilyloxy-3-(tetrahydropyran-2-yloxymethyl)-2-methylene-cyclopentyl]-6-chloro-9H-purine-2-carbamic acid tert-butyl ester; | 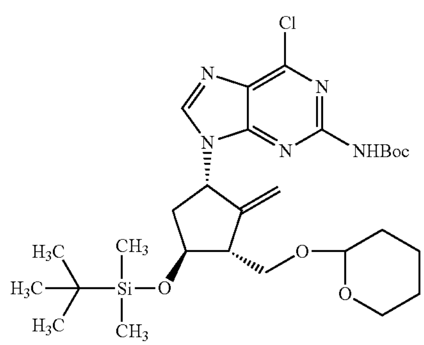 [SMILES: C=C1[C@H](COC2CCCCO2)[C@@H](O[Si](C)(C)C(C)(C)C)C[C@@H]1n1cnc2c(Cl)nc(NC(=O)OC(C)(C)C)nc21] |
| 9-[(1S,3R,4S)-4-(biphenyl-4-formyloxy)-3-(biphenyl-4-formyloxymethyl)-2-methylene-cyclopentyl]-6-chloro-9H-purine-2-carbamic acid tert-butyl ester; | 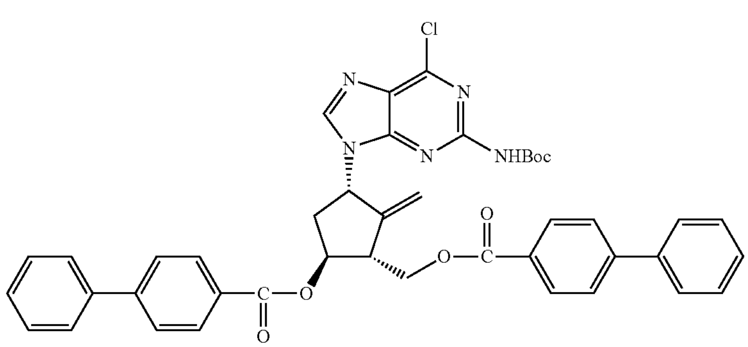 [SMILES: C=C1[C@H](COC(=O)c2ccc(-c3ccccc3)cc2)[C@@H](OC(=O)c2ccc(-c3ccccc3)cc2)C[C@@H]1n1cnc2c(Cl)nc(NC(=O)OC(C)(C)C)nc21] |

| Compound name | Structure |
|---|---|
| (4aR,6S,7aS)-6-chloro-9-(2,2-di-tert-butyl-5-methylene-hexahydro-cyclopenta[1,3,2]dioxasilin-6-yl)-9H-purine-2-carbamic acid tert-butyl ester | 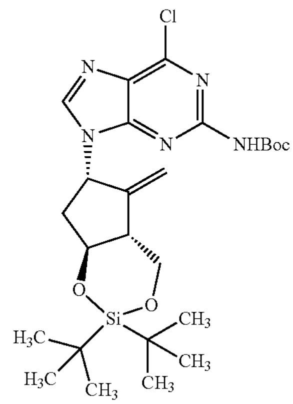 [SMILES: C=C1[C@@H]2CO[Si](C(C)(C)C)(C(C)(C)C)O[C@H]2C[C@@H]1n1cnc2c(Cl)nc(NC(=O)OC(C)(C)C)nc21] |
| (2S,4aR,6S,7aS)-6-chloro-9-(2-methyl-5-methylene-hexahydro-cyclopenta[1,3]dioxin-6-yl)-9H-purine-2-carbamic acid tert-butyl ester | 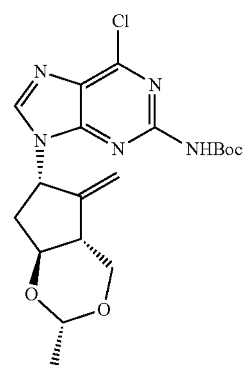 [SMILES: C=C1[C@@H]2CO[C@H](C)O[C@H]2C[C@@H]1n1cnc2c(Cl)nc(NC(=O)OC(C)(C)C)nc21] |
| (2R,4aR,6S,7aS)-6-chloro-9-(2-methyl-5-methylene-hexahydro-cyclopenta[1,3]dioxin-6-yl)-9H-purine-2-carbamic acid tert-butyl ester | 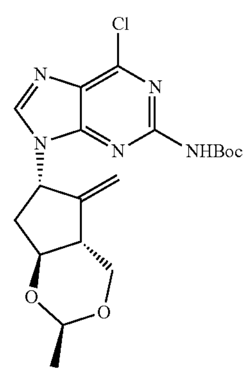 [SMILES: C=C1[C@@H]2CO[C@@H](C)O[C@H]2C[C@@H]1n1cnc2c(Cl)nc(NC(=O)OC(C)(C)C)nc21] |
| (4aR,6S,7aS)-6-chloro-9-(2-methyl-5-methylene-hexahydro-cyclopenta[1,3]dioxin-6-yl)-9H-purine-2-carbamic acid tert-butyl ester | 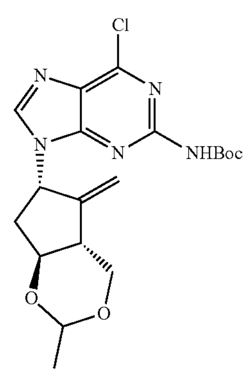 |

In another aspect, the present invention relates to a method for preparation of the compounds of formula 6, comprising reacting compound 4 with 2-protected amino-6-substituted purine compound 5 in the presence of Mitsunobu reaction reagents, to give the coupling reaction product 6

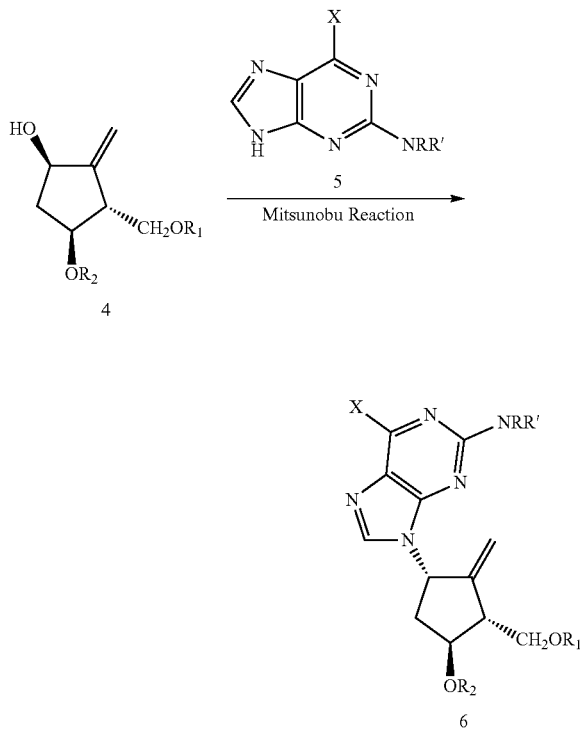

wherein $R_1$ and $R_2$, which are the same or different, are independently selected from hydroxy-protecting groups of the following Groups (i) to (iii):

(i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si; or (iii) $R_1$ and $R_2$ together with the five-member carbocycle to which they are attached form one of the following fused ring systems:

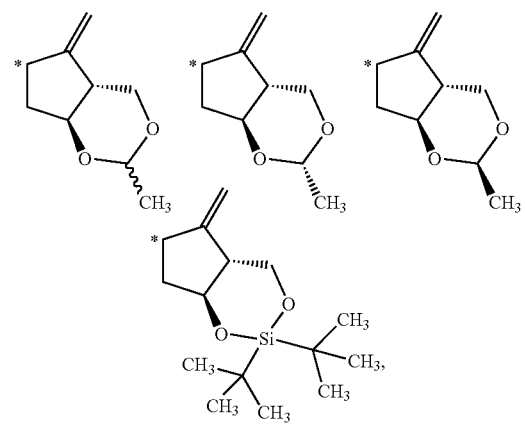

wherein $R_3$ is hydrogen atom, $C_{1-6}$ alkyl, phenyl or substituted phenyl in which the substituent on said phenyl is preferably selected from methoxy, ethoxy, halo, phenyl and nitro; $R_4$ and $R_5$, which are the same or different, are independently selected from $C_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

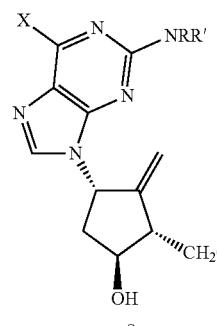

R and R', which are the same or different, are independently selected from hydrogen, alkoxycarbonyl or aralkoxycarbonyl, such as $C_{1-6}$ alkoxycarbonyl or $C_{5-10}$ aralkoxycarbonyl, preferably tort-butyloxycarbonyl, provided that R and R' are not both hydrogen; X is halo, alkoxy, halo-alkoxy or aralkoxy, such as $C_{1-6}$ alkoxy, halo-$C_{1-6}$ alkoxy or $C_{5-10}$ aralkoxy, preferably chloro, methoxy, benzyloxy, tert-butyloxy, particularly preferably chloro. The condition of said reaction is described as above.

In another aspect, the present invention relates to a method for preparation of the compounds of formula 7, comprising removing hydroxy-protecting groups from compound 6 to give compound 7,

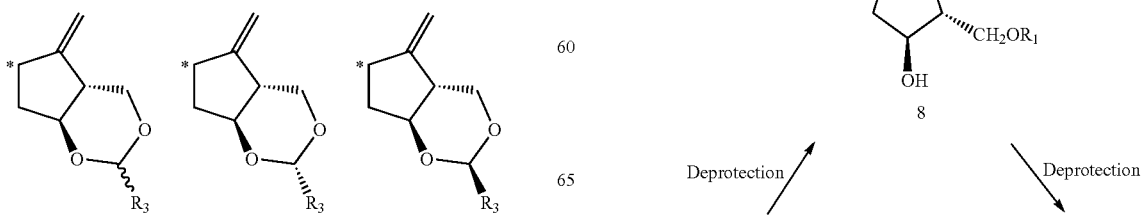

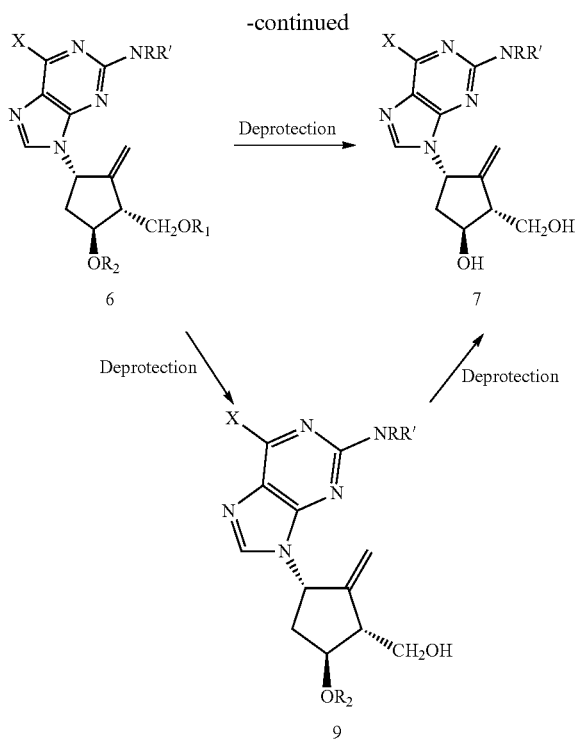

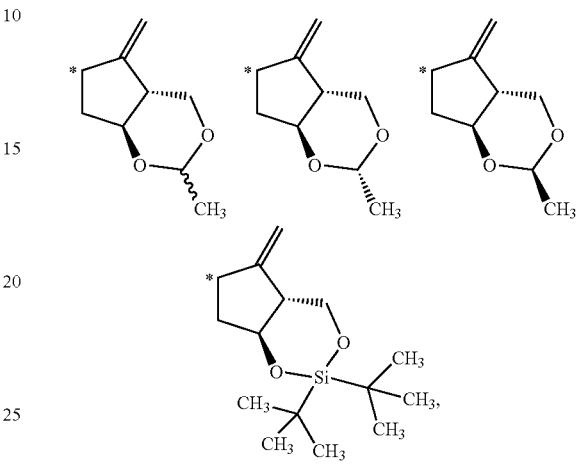

R$_4$ and R$_5$, which are the same or different, are independently selected from C$_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

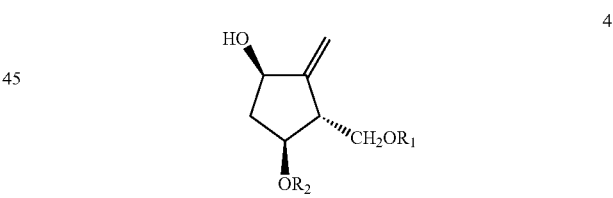

R and R', which are the same or different, are independently selected from hydrogen, alkoxycarbonyl or aralkoxycarbonyl, such as C$_{1-6}$ alkoxycarbonyl or C$_{5-10}$ aralkoxycarbonyl, preferably tert-butyloxycarbonyl, provided that R and R' are not both hydrogen; X is halo, alkoxy, halo-alkoxy or aralkoxy, such as C$_{1-6}$ alkoxy, halo-C$_{1-6}$ alkoxy or C$_{5-10}$ aralkoxy, preferably chloro, methoxy, benzyloxy, tert-butyloxy, particularly preferably chloro. The condition of said reaction is described as above.

In another aspect, the present invention relates to the compounds of formula 4:

wherein

R$_1$ and R$_2$, which are the same or different, are independently selected from hydroxy-protecting groups of the following Groups (i) to (iii):

(i) R$_1$ and R$_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) R$_1$ and R$_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that R$_1$ and R$_2$ are not both t-BuMe$_2$Si; or (iii) R$_1$ and R$_2$ together with the five-member carbocycle to which they are attached form one of the following fused ring systems:

wherein

R$_1$ and R$_2$, which are the same or different, are independently selected from hydroxy-protecting groups of the following Groups (i) to (iii):

(i) R$_1$ and R$_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) R$_1$ and R$_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that R$_1$ and R$_2$ are not both t-BuMe$_2$Si; or (iii) R$_1$ and R$_2$ together with the five-member carbocycle to which they are attached form one of the following fused ring systems:

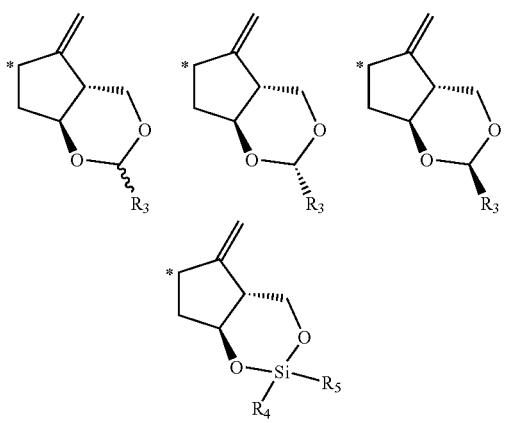

wherein R$_3$ is hydrogen atom, C$_{1-6}$ alkyl, phenyl or substituted phenyl in which the substituent on said phenyl is preferably selected from methoxy, ethoxy, halo, phenyl and nitro;

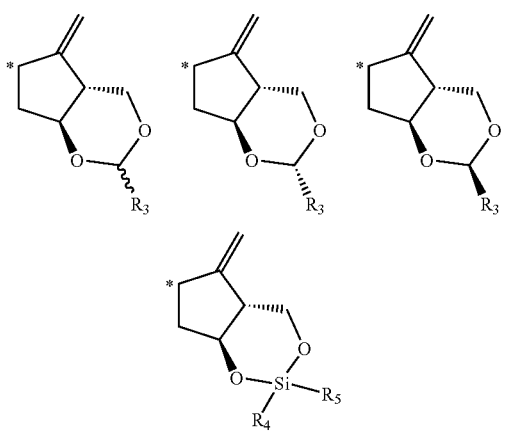

wherein $R_3$ is hydrogen atom, $C_{1-6}$ alkyl, phenyl or substituted phenyl in which the substituent on said phenyl is preferably selected from methoxy, ethoxy, halo, phenyl and nitro; $R_4$ and $R_5$, which are the same or different, are independently selected from $C_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

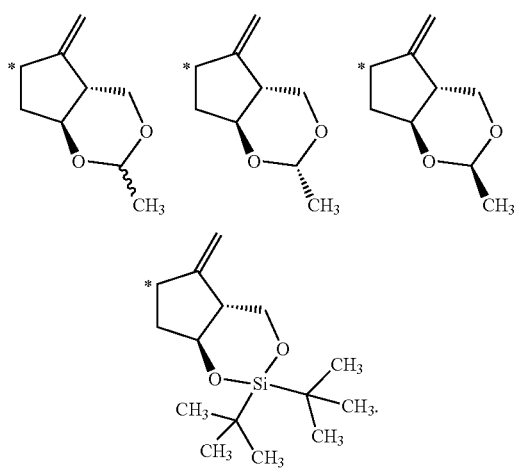

In the compounds of above formula 4, the following compounds are preferred.

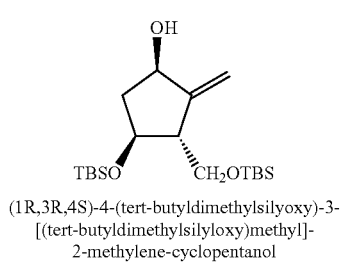

(1R,3R,4S)-4-(tert-butyldimethylsilyoxy)-3-[(tert-butyldimethylsilyloxy)methyl]-2-methylene-cyclopentanol    4a

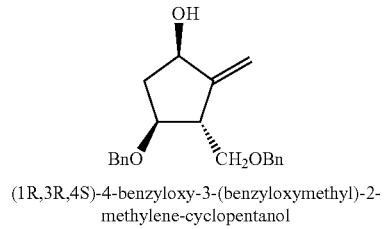

(1R,3R,4S)-4-benzyloxy-3-(benzyloxymethyl)-2-methylene-cyclopentanol    4b

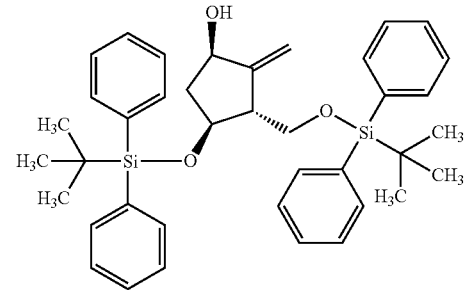

(1R,3R,4S)-4-(tert-butyldiphenylsilyloxy)-3-(tert-butyldiphenylsilyloxymethyl)-2-methylene-1-cyclopentanol    4c

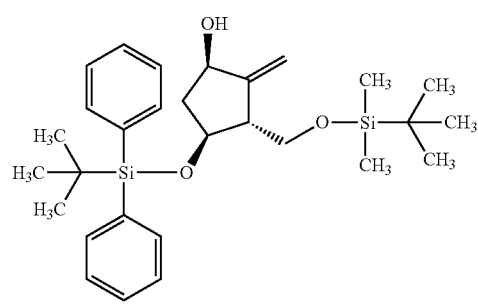

(1R,3R,4S)-4-(tert-butyldiphenylsilyloxy)-3-(tert-butyldimethylsilyloxymethyl)-2-methylene-1-cyclopentanol    4d

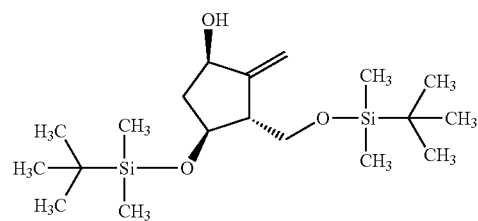

(1R,3R,4S)-4-tert-butyldiimethylsilyloxy-3-(tert-butyldiphenylsilyloxymethyl)-2-methylene-1-cyclopentanol    4e

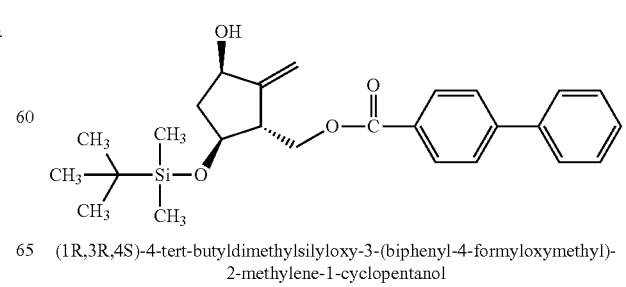

(1R,3R,4S)-4-tert-butyldimethylsilyloxy-3-(biphenyl-4-formyloxymethyl)-2-methylene-1-cyclopentanol    4f

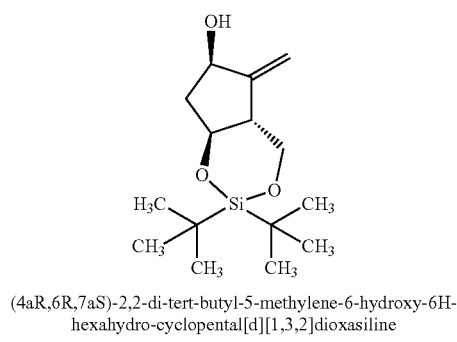

(4aR,6R,7aS)-2,2-di-tert-butyl-5-methylene-6-hydroxy-6H-hexahydro-cyclopenta[d][1,3,2]dioxasiline 4h

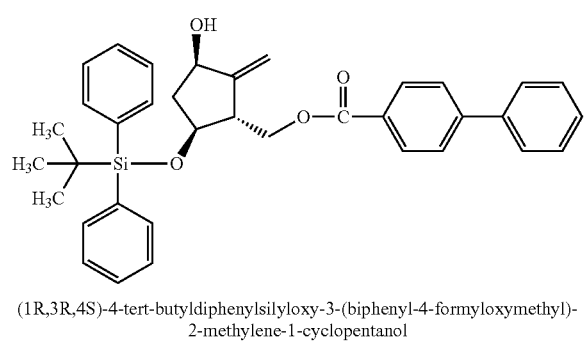

(1R,3R,4S)-4-tert-butyldiphenylsilyloxy-3-(biphenyl-4-formyloxymethyl)-2-methylene-1-cyclopentanol 4i

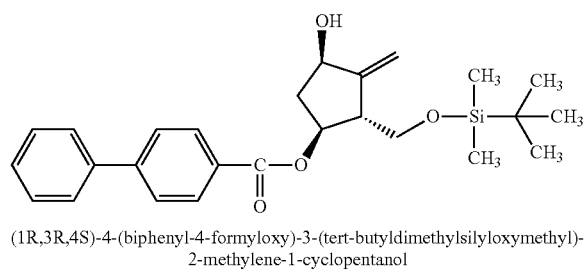

(1R,3R,4S)-4-(biphenyl-4-formyloxy)-3-(tert-butyldimethylsilyloxymethyl)-2-methylene-1-cyclopentanol 4j

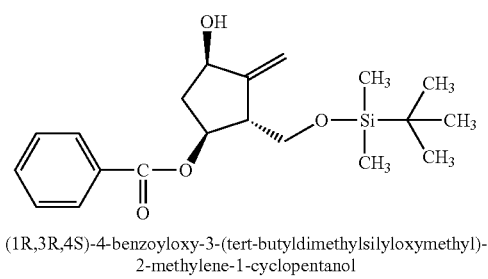

(1R,3R,4S)-4-benzoyloxy-3-(tert-butyldimethylsilyloxymethyl)-2-methylene-1-cyclopentanol 4k

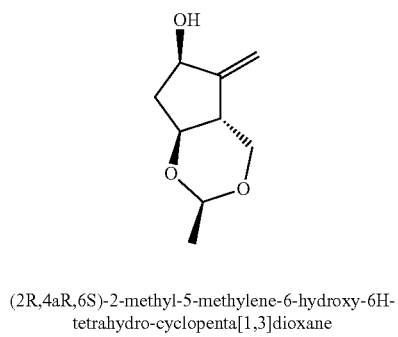

(2R,4aR,6S)-2-methyl-5-methylene-6-hydroxy-6H-tetrahydro-cyclopenta[1,3]dioxane

4l

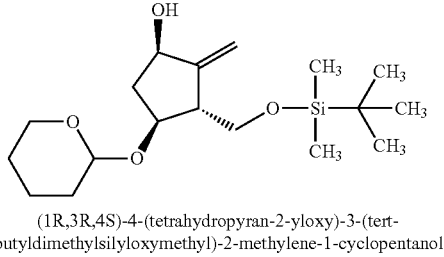

(1R,3R,4S)-4-(tetrahydropyran-2-yloxy)-3-(tert-butyldimethylsilyloxymethyl)-2-methylene-1-cyclopentanol Compound 4 may be synthesized according to the methods similar to those described in literatures, or compound 4 may also be prepared by the method comprising:

a) opening the ring of compound 2 to directly yield cyclopentane intermediate 3

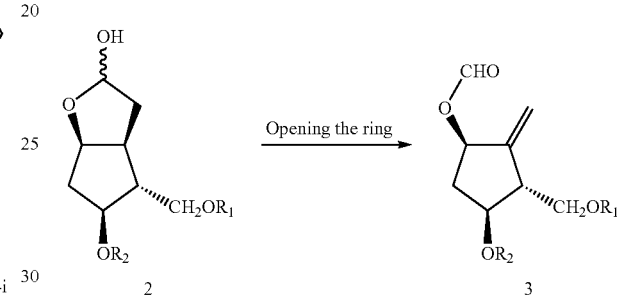

wherein $R_1$ and $R_2$, which are the same or different, are independently selected from hydroxy-protecting groups of the following Groups (i) to (iii):

(i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si; or (iii) $R_1$ and $R_2$ together with the five-member carbocycle to which they are attached form one of the following fused ring systems:

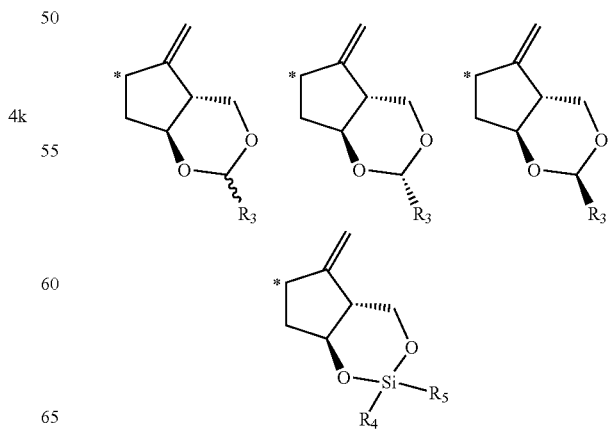

wherein $R_3$ is hydrogen atom, $C_{1-6}$ alkyl, phenyl or substituted phenyl in which the substituent on said phenyl is preferably selected from methoxy, ethoxy, halo, phenyl and nitro; $R_4$ and $R_5$, which are the same or different, are independently selected from $C_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

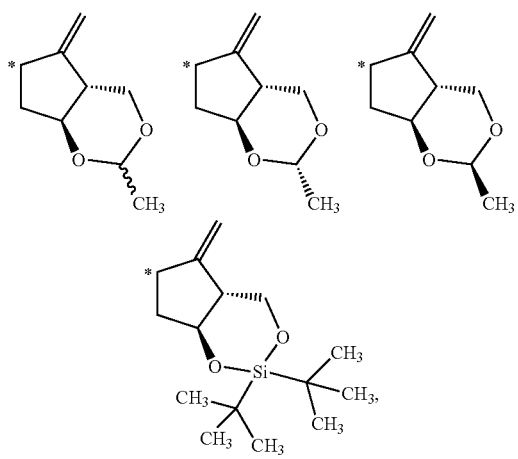

and
b) alcoholysis or hydrolysis of the compound of formula 3 to yield compound 4

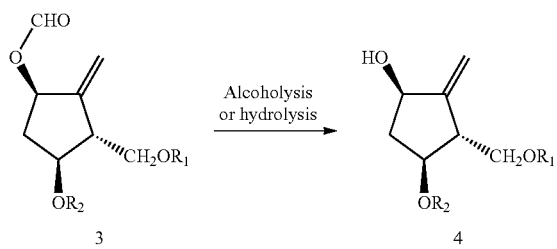

wherein $R_1$ and $R_2$ are defined as above.

Compound 2 may be prepared according to known methods described in references such as EP134153 or similar methods thereof, or according to the methods described in the Examples of the present application or similar methods thereof.

In above step a), the ring of compound 2 is directly opened under catalysis of Cu (II) salt, using suitable reagents which can induce cleavage through free radicals, such as $PhI(OAc)_2$, $Mn(OAc)_3$ or $Pb(OAc)_4$, preferably $Pb(OAc)_4$, to afford cyclopentane intermediate 3. This reaction may be performed in a hydrocarbon solvent, such as benzene, toluene, cyclohexane, petroleum ether or n-heptane, or a non-protonic polar solvent, such as acetonitrile, ethyl acetate, halogenated hydrocarbons or halogenated aromatic hydrocarbons such as trifluorotoluene, or mixtures thereof, preferably in the presence of organic base such as triethylamine or pyridine.

In above step b), alcoholysis or hydrolysis of the compound of formula 3 is performed in the presence of a base such as ammonia, triethylamine, $K_2CO_3$ or alkoxide, in an organic solvent such as methanol, ethanol or a mixture thereof, or in water or a mixture of water and organic solvents, e.g., a mixture of EtOH and water, to afford Compound 4. Preferably, $K_2CO_3$ and methanol are used in the reaction of this step.

Thus, in a preferred embodiment, Compound 4 may be prepared by the method comprising:

a) opening the ring of Compound 2 under catalysis of Cu (II) salt by using $Pb(OAc)_4$, preferably in the presence of organic base such as triethylamine or pyridine, to directly afford cyclopentane intermediate 3; and b) alcoholysis of the compound of formula 3 is performed in the presence of $K_2CO_3$, in methanol, to afford Compound 4.

In each step of above methods, depending on the reaction condition used, reaction time may be from several minutes to several days, such as from 30 minutes to 14 days; reaction temperature may be from about −78° C. to the reflux temperature of the solvent used, such as from 0° C. to 150° C., especially from room temperature to the reflux temperature of the solvent used.

In above step a), the compounds of formula 3 obtained are novel compounds.

Thus, in one aspect, the present invention also relates to the compounds of formula 3:

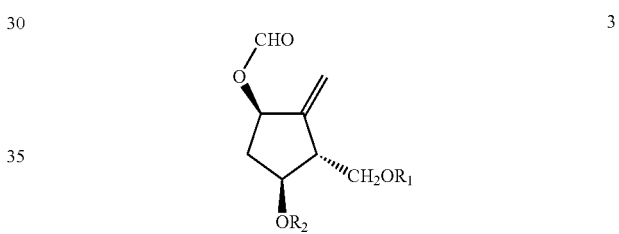

wherein $R_1$ and $R_2$, which are the same or different, are independently selected from hydroxy-protecting groups of the following Groups (i) to (iii):

(i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si; or (iii) $R_1$ and $R_2$ together with the five-member carbocycle to which they are attached form one of the following fused ring systems:

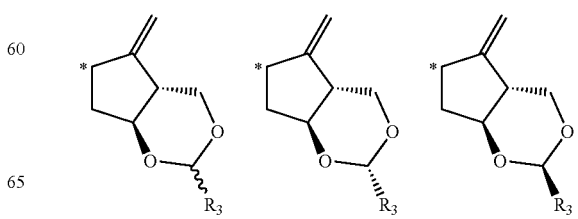

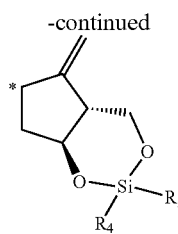

wherein $R_3$ is hydrogen atom, $C_{1-6}$ alkyl, phenyl or substituted phenyl in which the substituent on said phenyl is preferably selected from methoxy, ethoxy, halo, phenyl and nitro; $R_4$ and $R_5$, which are the same or different, are independently selected from $C_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

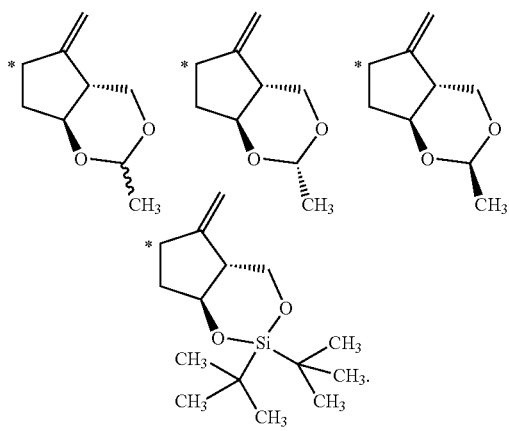

Particularly preferably the compound of formula 3 is (1R, 3R,4S)-4-(tert-butyldimethylsilyloxy)-3-[(tert-butyldimethylsilyloxy)methyl]-2-methylene-cyclopentyl formate, which has the structure below.

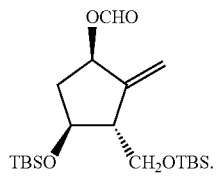

Furthermore, particularly preferably the compounds of formula 3 are the following compounds.

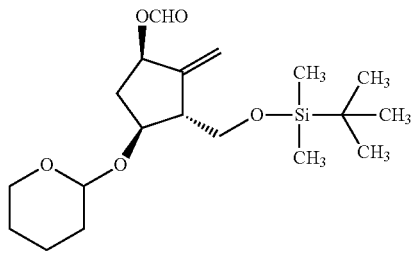

(1R,3R,4S)-4-(tetrahydropyran-2-yloxy)-3-(tert-butyldimethylsilyloxymethyl)-2-methylene-cyclopentyl formate

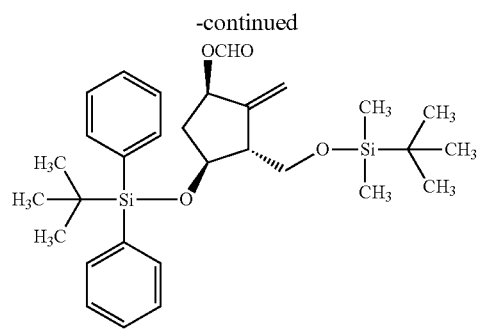

(1R,3R,4S)-4-(tert-butyldiphenylsilyloxy)-3-(tert-butyldimethylsilyloxymethyl)-2-methylene-cyclopentyl formate

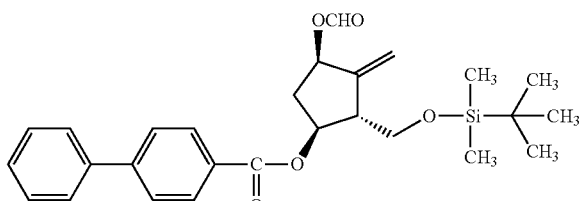

(1R,3R,4S)-4-(biphenyl-4-formyloxy)-3-(tert-butyldimethylsilyloxymethyl)-2-methylene-cyclopentyl formate

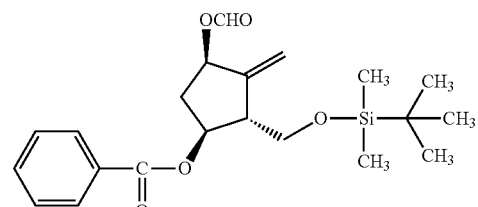

(1R,3R,4S)-4-benzoloxy-3-(tert-butyldimethylsilyloxymethyl)-2-methylene-cyclopentyl formate

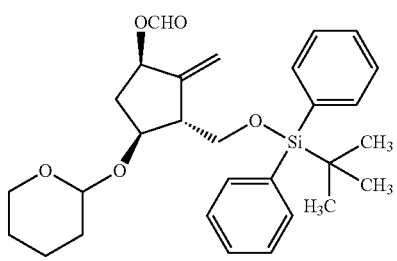

(1R,3R,4S)-4-(tetrahydropyran-2-yloxy)-3-(tert-butyldiphenylsilyloxymethyl)-2-methylene-cyclopentyl formate

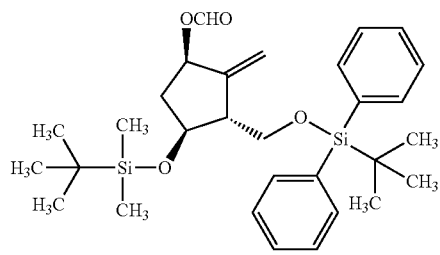

(1R,3R,4S)-4-tert-butyldiphenylsilyloxy-3-(tert-butyl-diphenylsilyloxymethyl)-2-methylene-cyclopentyl formate -continued

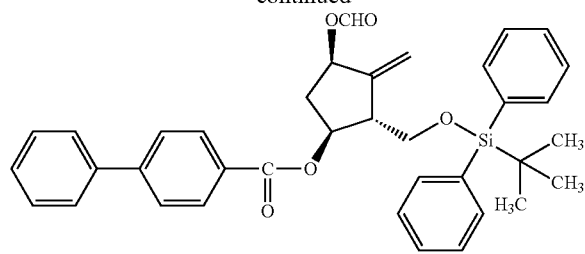

(1R,3R,4S)-4-(biphenyl-4-formyloxy)-3-(tert-butyldimethylsilyloxymethyl)-2-methylene-cyclopentanol formate

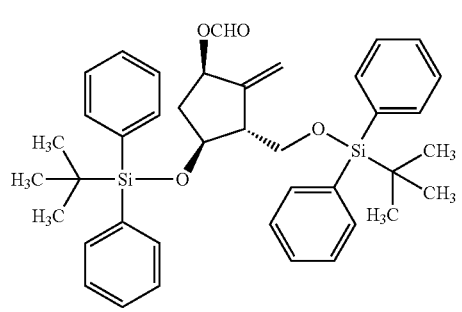

(1R,3R,4S)-4-(tert-butyldimethylsilyloxy)-3-(tert-butyldiphenylsilyloxymethyl)-2-methylene-cyclopentyl formate

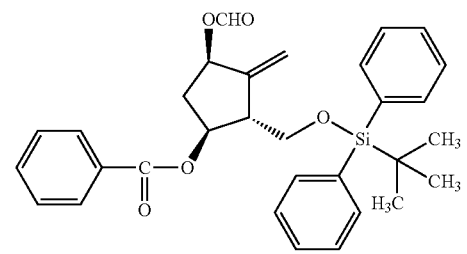

(1R,3R,4S)-4-benzoyloxy-3-(tert-butyldiphenylsilyloxymethyl)-2-methylene-cyclopentyl formate

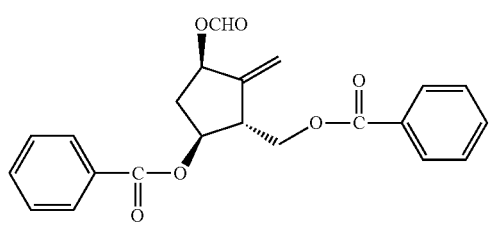

(1R,3R,4S)-4-benzoyloxy-3-benzoyloxymethyl)-2-methylene-cyclopentyl formate

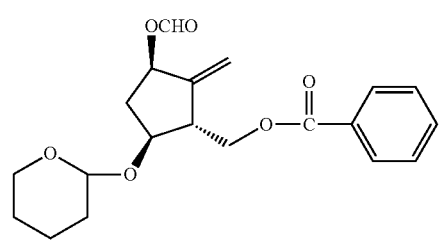

(1R,3R,4S)-4-(tetrahydropyran-2-yloxy)-3-(benzoyloxymethyl)-2-methylene-cyclopentyl formate -continued

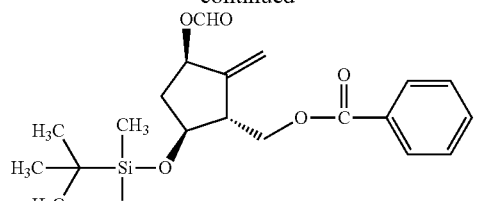

(1R,3R,4S)-4-tert-butyldiphenylsilyloxy-3-(benzoyloxymethyl)-2-methylene-cyclopentyl formate

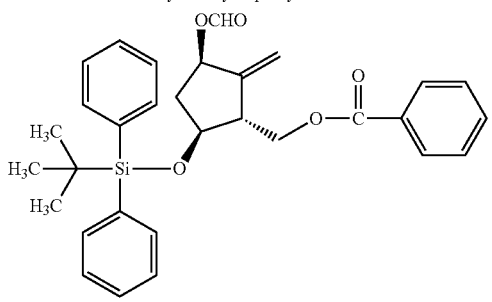

(1R,3R,4S)-4-(tert-butyldiphenylsilyloxy)-3-(benzoyloxymethyl)-2-methylene-cyclopentanol formate

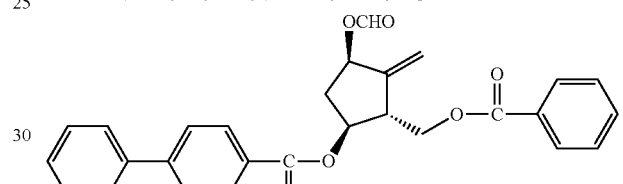

(1R,3R,4S)-4-(biphenyl-4-formyloxy)-3-(benzoyloxymethyl)-2-methylene-cyclopentanol formate

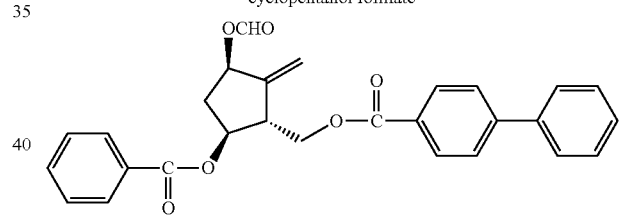

(1R,3R,4S)-4-benzoyloxy-3-(biphenyl-4-formyloxymethyl)-2-methylene-cyclopentanol formate

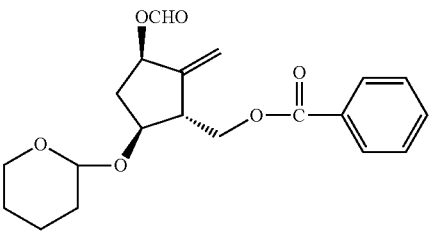

(1R,3R,4S)-4-(tetrahydropyran-2-yloxy)-3-(biphenyl)-4-formyloxymethyl)-2-methylene-cyclopentyl formate

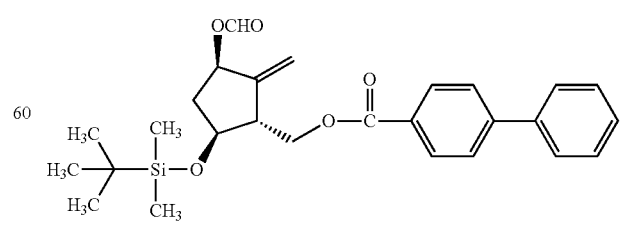

(1R,3R,4S)-4-tert-butyldimethylsilyloxy-3-(biphenyl-4-formyloxymethyl)-2-methylene-cyclopentyl formate

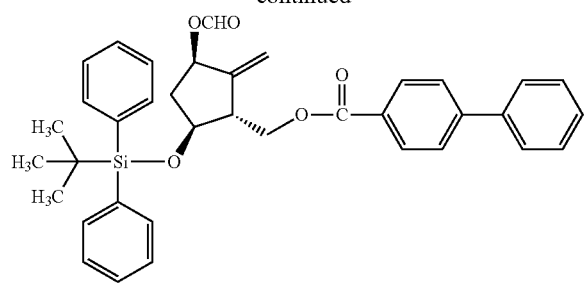

(1R,3R,4S)-4-(tert-butyldiphenylsilyloxy)-3-(biphenyl-4-formyloxymethyl)-2-methylene-cyclopentyl formate

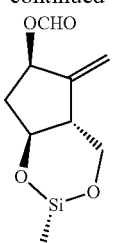

(2S,4aR,6S,7aS)-2-methylene-6H-tetrahydro-cyclopenta[1,3]dioxasilin-6-yl formate

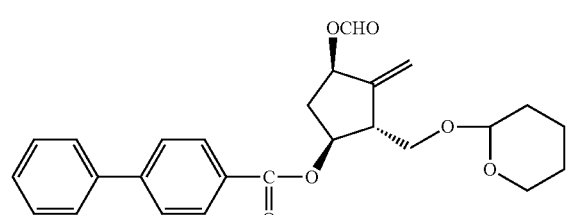

(1R,3R,4S)-4-(biphenyl-4-formyloxy)-3-(tetrahydropyran-2-yloxymethyl)-2-methylene-cyclopentyl formate

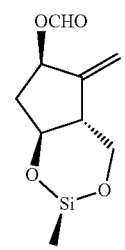

(2S,4aR,6S,7aS)-2-methyl-5-methylene-6H-tetrahydro-cyclopenta[1,3]dioxan-6-yl formate In another aspect, the present invention relates to the method for preparing the compound of formula 3, comprising the following step:

a) opening the ring of compound 2 to directly yield cyclopentane intermediate 3

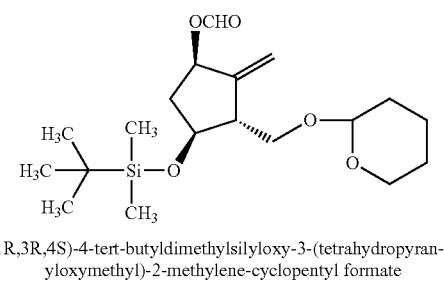

(1R,3R,4S)-4-tert-butyldimethylsilyloxy-3-(tetrahydropyran-2-yloxymethyl)-2-methylene-cyclopentyl formate

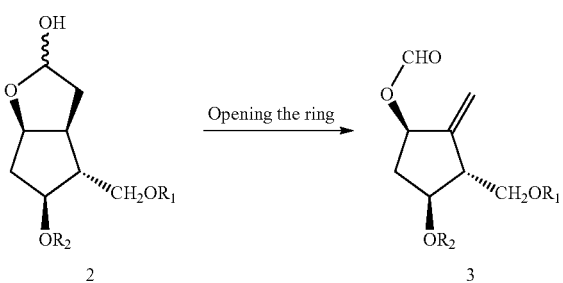

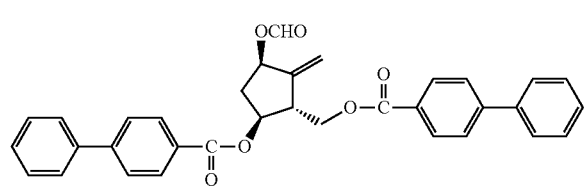

(1R,3R,4S)-4-(biphenyl-4-formyloxy)-3-(biphenyl-4-formyloxymethyl)-2-methylene-cyclopentanol formate wherein $R_1$ and $R_2$, which are the same or different, are independently selected from hydroxy-protecting groups of the following Groups (i) to (iii):

(i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si; or

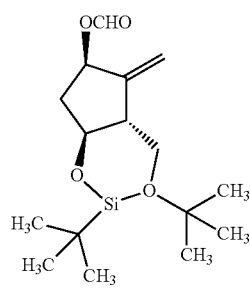

(4aR,6R,7aS)-2,2-di-tert-butyl-5-methylene-6H-hexahydro-cyclopenta[d][1,3,2]dioxasilin-6-yl formate (iii) $R_1$ and $R_2$ together with the five-member carbocycle to which they are attached form one of the following fused ring systems:

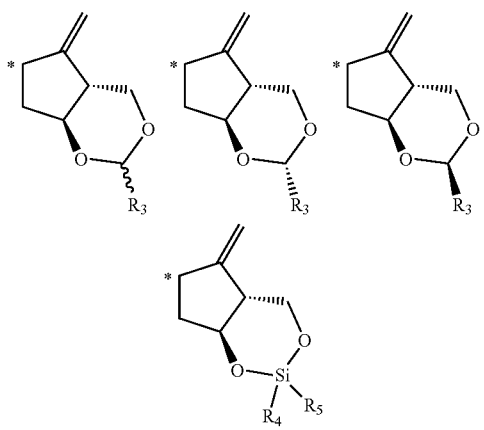

wherein R$_3$ is hydrogen atom, C$_{1-6}$ alkyl, phenyl or substituted phenyl in which the substituent on said phenyl is preferably selected from methoxy, ethoxy, halo, phenyl and nitro; R$_4$ and R$_5$, which are the same or different, are independently selected from C$_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

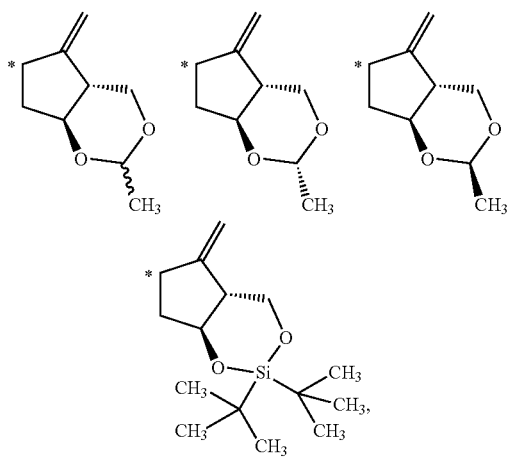

and
the reaction condition of step a) is described as above.

In another aspect, the present invention relates to the method for preparing the compound of formula 1 using compound 2 as starting material, comprising the following steps:

a) opening the ring of compound 2 to directly yield cyclopentane intermediate 3

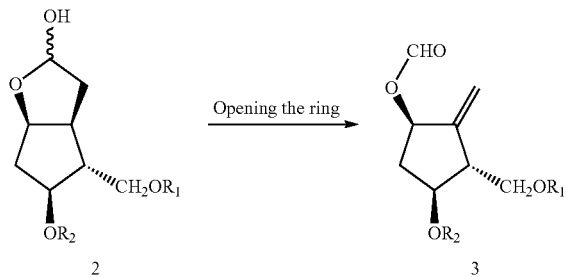

wherein
R$_1$ and R$_2$, which are the same or different, are independently selected from hydroxy-protecting groups of the following Groups (i) to (iii):

(i) R$_1$ and R$_2$, independent of each other, are selected from alkyl, halo-alkyl, benzyl, t-BuMe$_2$Si, t-BuPh$_2$Si, (i-Pr)$_3$Si or Et$_3$Si, preferably t-BuMe$_2$Si; or (ii) R$_1$ and R$_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that R$_1$ and R$_2$ are not both t-BuMe$_2$Si; or (iii) R$_1$ and R$_2$ together with the five-member carbocycle to which they are attached form one of the following fused ring systems:

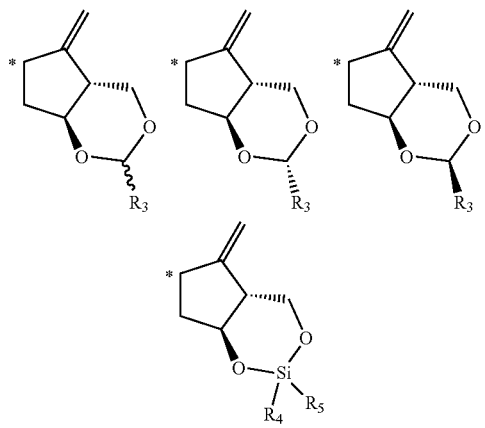

wherein R$_3$ is hydrogen atom, C$_{1-6}$ alkyl, phenyl or substituted phenyl in which the substituent on said phenyl is preferably selected from methoxy, ethoxy, halo, phenyl and nitro; R$_4$ and R$_5$, which are the same or different, are independently selected from C$_{1-6}$ alkyl or aryl, preferably tert-butyl or phenyl; wherein the symbol * represents the attachment point through which said fused ring is attached to the remaining moiety of the molecule;

said fused ring preferably being one of the following fused ring systems:

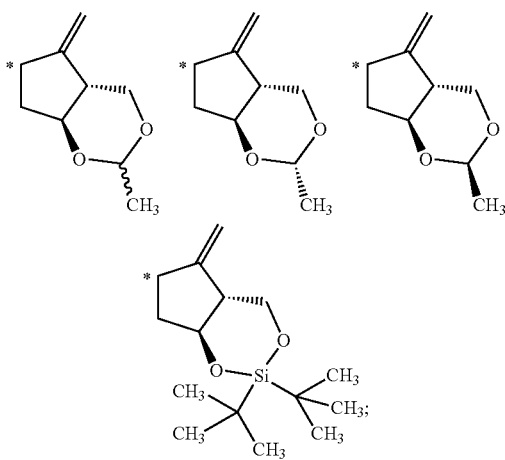

b) alcoholysis or hydrolysis of the compound of formula 3 to yield compound 4

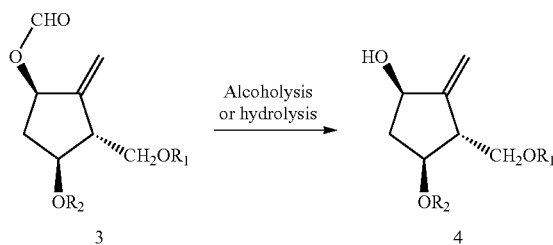

wherein $R_1$ and $R_2$ are defined as above;

c) Mitsunobu reaction of compound 4 with 2-protected amino-6-substituted purine compound 5 to give the coupling reaction product 6

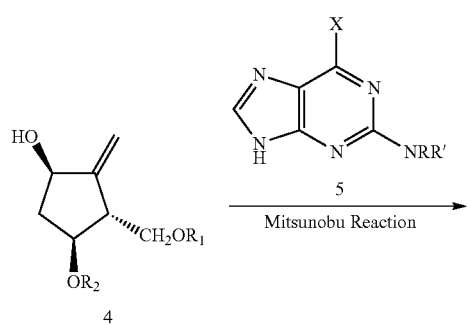

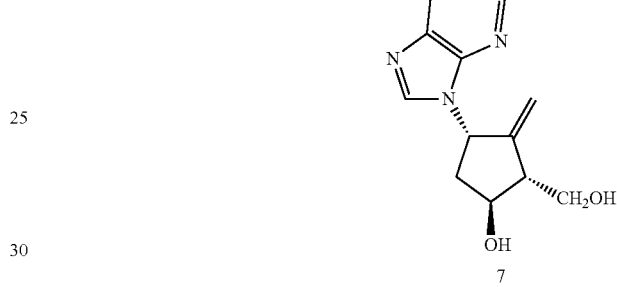

wherein $R_1$ and $R_2$ are defined as above;

R and R', which are the same or different, are independently selected from hydrogen, alkoxycarbonyl or aralkoxycarbonyl, such as $C_{1-6}$ alkoxycarbonyl or $C_{5-10}$ aralkoxycarbonyl, preferably tert-butyloxycarbonyl, provided that R and R' are not both hydrogen; X is halo, alkoxy, halo-alkoxy or aralkoxy, such as $C_{1-6}$ alkoxy, halo-$C_{1-6}$ alkoxy or $C_{5-10}$ aralkoxy, preferably chloro, methoxy, benzyloxy, tert-butyloxy, particularly preferably chloro;

d) when $R_1$ and $R_2$ are both acyl protective groups or neither of them is acyl protective group, removing hydroxy-protecting groups from compound 6, to give compound 7

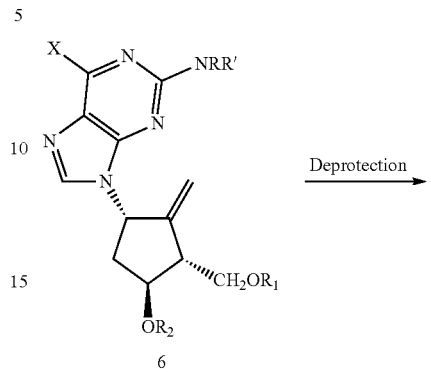

wherein X, $R_1$, $R_2$, R and R' are defined as above;

e) hydrolysis of compound 7 to give the compound of formula 1 (Entecavir)

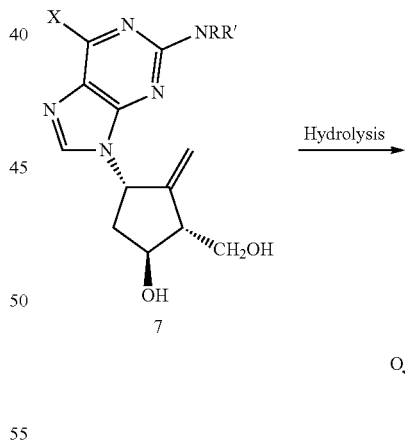

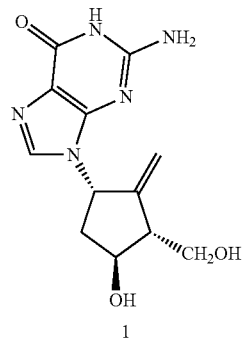

wherein X, R and R' are defined as above; or d') when neither of $R_1$ and $R_2$ is acyl protective group, deprotecting compound 6 while hydrolysis in one-pot manner, to directly yield the compound of formula 1

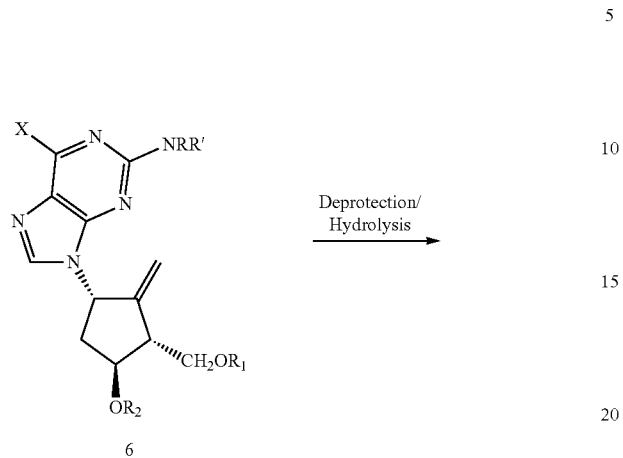

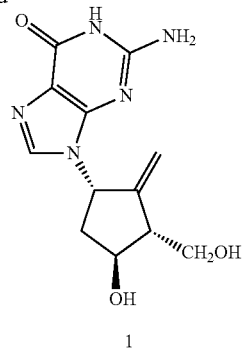

wherein X, $R_1$, $R_2$, R and R' are defined as above; or d") when either of $R_1$ and $R_2$ is acyl protective group, such as benzoyl, benzoyl in which the phenyl ring bears substituent(s), or biphenylformyl, deprotecting compound 6 to give compound 8 or 9 which is then hydrolyzed to give compound 1 or is converted to compound 7 followed by hydrolysis to give compound 1,

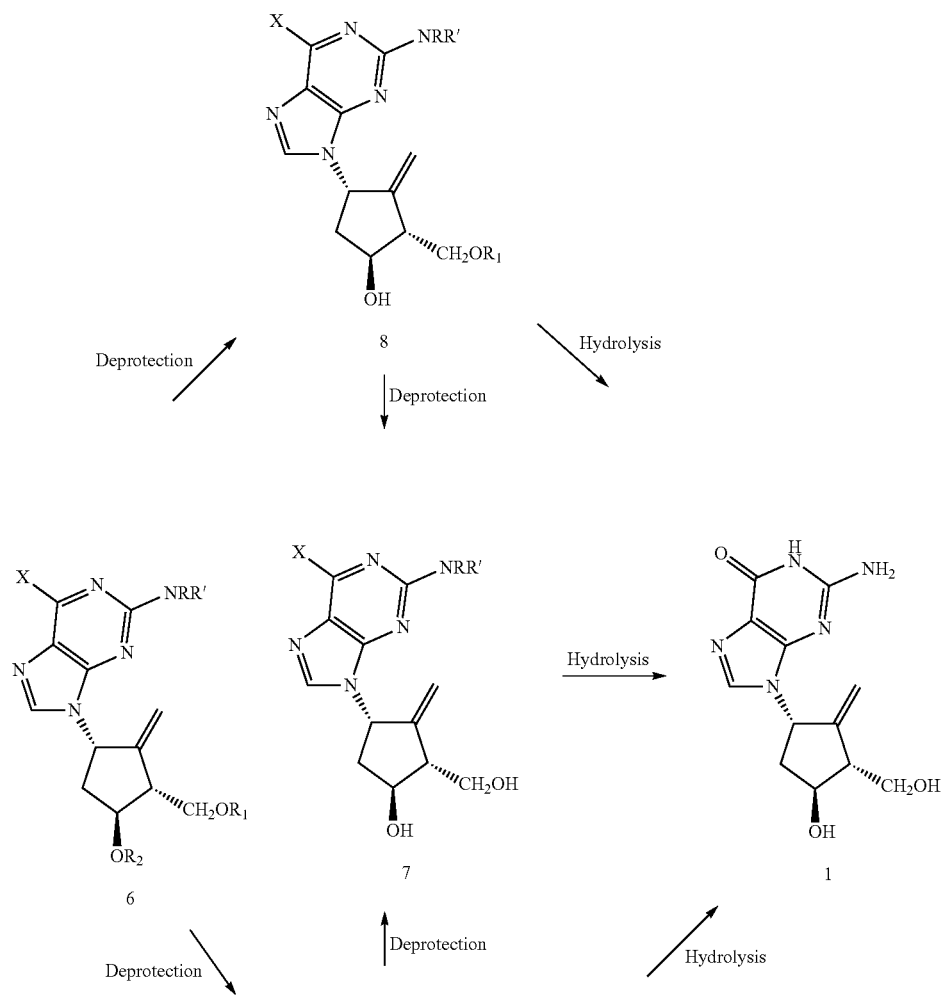

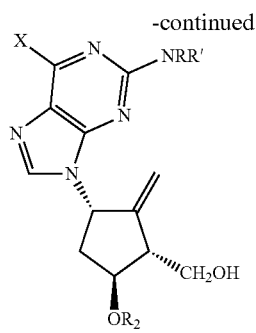

9 wherein X, $R_1$, $R_2$, R and R' are defined as above.

The reaction conditions of each step of said method are described as above.

In a preferred embodiment, the method for preparing the compound of formula 1 comprises the following steps:

a) opening the ring of compound 2 to directly yield cyclopentane intermediate 3

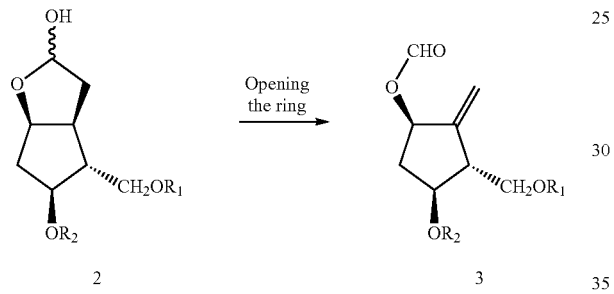

b) alcoholysis or hydrolysis of the compound of formula 3 to yield compound 4

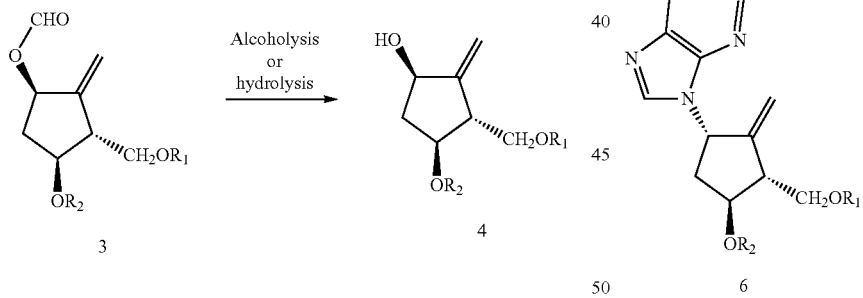

c) Mitsunobu reaction of compound 4 with 2-protected amino-6-substituted purine compound 5 to give the coupling reaction product 6

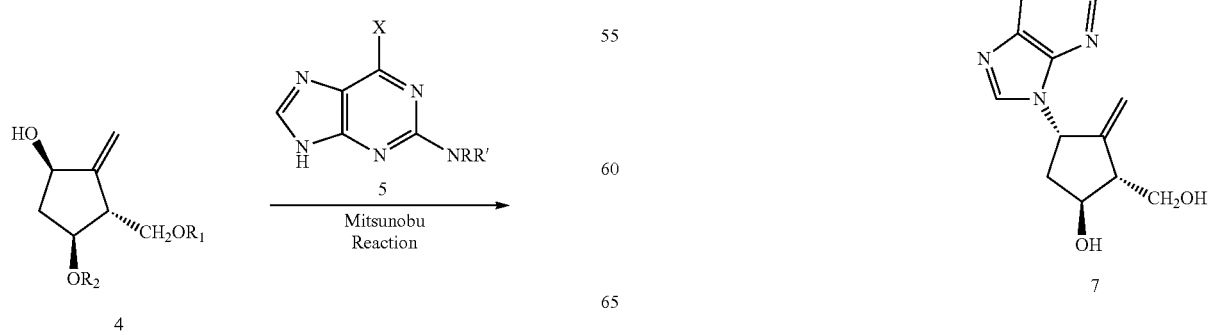

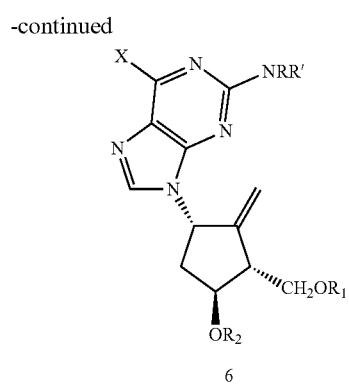

6 d) removing hydroxy-protecting groups from compound 6 to give compound 7 e) hydrolysis of compound 7 to afford the compound of formula 1

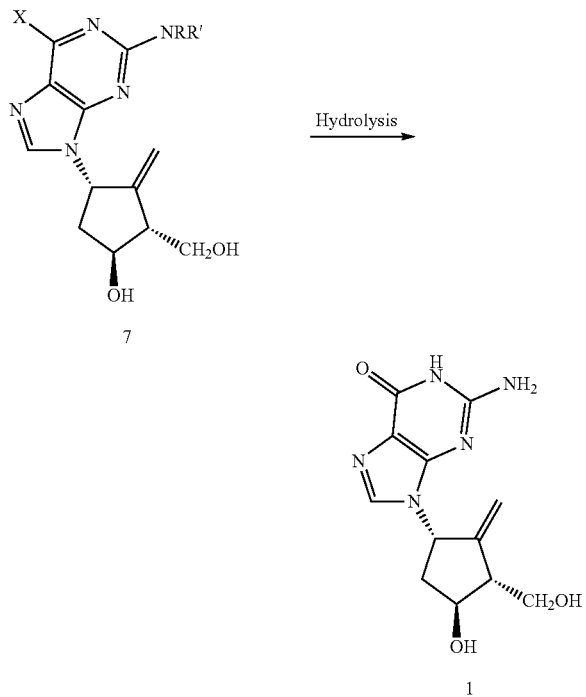

or
d') deprotecting compound 6 while hydrolysis in one-pot manner, to directly yield the compound of formula 1

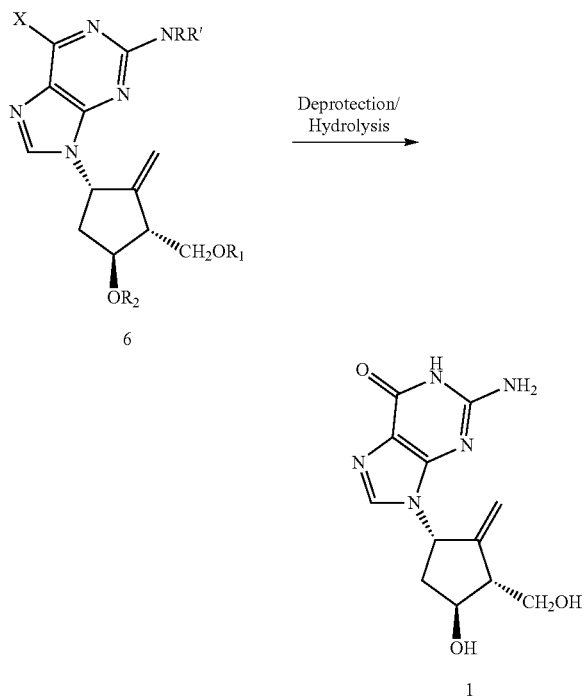

in each step of above method, $R_1$ and $R_2$, which are the same or different, are independently selected from hydroxy-protecting group, such as alkyl, halo-alkyl, benzyl, t-BuMe$_2$Si, t-BuPh$_2$Si, (i-Pr)$_3$Si or Et$_3$Si, preferably t-BuMe$_2$Si; R and R', which are the same or different, are independently selected from hydrogen, alkoxycarbonyl or aralkoxycarbonyl, such as $C_{1-6}$ alkoxycarbonyl or $C_{5-10}$ aralkoxycarbonyl, preferably tert-butyloxycarbonyl, provided that R and R' are not both hydrogen; X is halo, alkoxy, halo-alkoxy or aralkoxy, such as $C_{1-6}$ alkoxy, halo-$C_{1-6}$ alkoxy or $C_{5-10}$ aralkoxy, preferably chloro, methoxy, benzyloxy, tert-butyloxy, particularly preferably chloro.

The reaction conditions of step a) to step e) are described as above.

In a particularly preferred embodiment, Entecavir of formula 1 is synthesized by the method comprising the following steps:

a) opening the ring of Compound 2 under catalysis of Cu (II) salt by using Pb(OAc)$_4$, preferably in the presence of organic base such as triethylamine or pyridine, to directly afford cyclopentane intermediate 3;

b) alcoholysis of the compound of formula 3 in the presence of K$_2$CO$_3$, in methanol, to afford Compound 4;

c) Mitsunobu reaction of compound 4 with 2-protected amino-6-substituted purine compound 5, in the presence of Ph$_3$P/EtO$_2$CN=NCO$_2$Et or Ph$_3$P/i-PrO$_2$CN=NCO$_2$i-Pr, in a non-protonic solvent such as aromatic hydrocarbons, halogenated aromatic hydrocarbons, halogenated hydrocarbons or ethers, e.g., THF, to give the coupling reaction product 6;

d) removing hydroxy-protecting groups from compound 6, in the presence of tetrabutylammonium fluoride (TBAF) or hydrochloric acid, to give compound 7;

e) hydrolysis of compound 7 in the presence of hydrochloric acid, in tetrahydrofuran, to give the compound of formula 1.

A skilled person in the art will understand that, in above method for preparation of Entecavir, the reaction product of any one of step a) to step e) can be used as starting material to perform subsequent steps described above to afford the compound of formula 1. For example, the compounds of formula 3 can be used as starting material to perform steps b) to e) described above to afford the compound of formula 1, or the compounds of formula 6 can be used as starting material to perform steps d) and e) described above to afford the compound of formula 1, or the compounds of formula 7 can be used as starting material to perform step e) described above to afford the compound of formula 1.

EXAMPLES

The methods of the present invention will be further illustrated by the following examples. It should be understood that the following examples are provided for purpose of better understanding the present invention, not intended to limit the scope of the present invention in any manner.

The abbreviations used in the present application have the following meanings.

ABBREVIATIONS

Boc tert-butyloxycarbonyl
DEAD diethyl azodicarboxylate
EtOAc ethyl acetate
TBAF tetrabutylammonium fluoride
THF tetrahydrofuran
t-BuMe$_2$Si tert-butyldimethylsilyl
Preparation of Starting Materials:
The starting materials and methods for synthesis of the compounds of formula 2 are known in the art. The compounds of formula 2 can be prepared by the following methods or similar methods thereof.

(1) When $R_1$ and $R_2$ together with the five-member carbocycle to which they are attached form fused ring systems in the compounds of formula 2, for example, the synthesis of starting material is illustrated as below.

Synthesis of the following compound: (4aR,4bS, 7aR,8aS)-2-methyl-octahydro-furo[3',2':3,4]cyclopenta[1,2-d][1,3,2]dioxasiline-6(7aH)-one

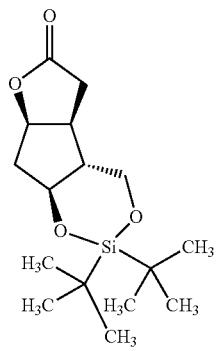 [SMILES: CC(C)(C)[Si]1(C(C)(C)C)OC[C@H]2[C@@H]3CC(=O)O[C@@H]3C[C@@H]2O1]

To a reaction bottle under $N_2$, Corey Diol (172 g, 1 mol), 2,6-dimethylpyridine (257 ml, 2.2 mol) and DMF (1700 g) were added. To the mixture di-tert-butylsilyl bis(trifluoromethanesulfonic acid) ester (400 ml, 1.1 mol) was added dropwise with stirring at room temperature. After addition, the reaction was performed at room temperature until the reaction completed. The reaction mixture was poured into water slowly. A solid was precipitated, filtered, and the filter cake was dried to afford the desired product.

NMR (CDCl$_3$, 500 MHz) $^1$HNMR: δ=0.98 (s, 9H), 1.03 (s, 9H), 1.83 (m, 2H), 2.29 (m, 1H), 2.39 (m, 1H), 2.70 (m, 2H), 3.86 (m, 1H), 2.01 (m, 1H), 4.24 (m, 1H), 4.83 (m, 1H);
$^{13}$CNMR: δ=20.04, 22.92, 27.30, 27.62, 33.20, 37.80, 40.25, 50.52, 68.25, 78.83.

Synthesis of the Following Compound: (2R,4aR, 4bS,7aR,8aS)-2-methyl-hexahydro-furo[3',2':3,4] cyclopenta[1,2-d][1,3]dioxin-6(7aH)-one

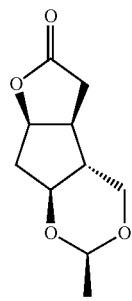

To a reaction bottle under $N_2$, Corey lactone diol (172 g, 1 mol), anhydrous p-toluene sulfonic acid (17.2 g), dichloromethane (1720 ml) and acetal (354 g, 3 mol) were added. The mixture was stirred at room temperature for 1 hour, and then heated to reflux until the reaction was completed. The reaction mixture was concentrated to allow crystallization, to give 90 g of desired product.

NMR (CDCl$_3$, 500 MHz) $^1$HNMR: δ=1.32 (d, 3H), 1.63 (m, 1H), 1.82 (m, 1H), 2.27 (m, 2H), 2.63 (m, 2H), 3.36 (m, 1H), 3.53 (m, 1H), 4.23 (m, 1H), 4.64 (m, 1H), 4.85 (m, 1H);
$^{13}$CNMR: δ=20.70, 32.56, 36.70, 37.07, 45.40, 70.52, 79.84, 80.68, 99.80, 176.18.

(2) When each of $R_1$ and $R_2$ in the compounds of formula 2 is independently silyl protective group or acyl protective group, for example, the synthesis of starting materials is illustrated as below.

Firstly, the following compound (its abbreviation: TCOD) was synthesized: (3aS,4R,5S,6aR)-hexahydro-5-hydroxy-4-(tert-butyldimethylsilyloxymethyl)-2H-cyclopenta[b]furan-2-one

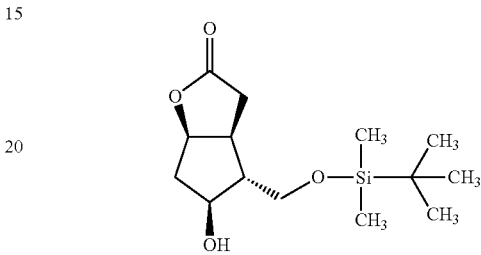

To a reaction bottle under $N_2$, Corey lactone diol (172 g, 1 mol), imidazole (95.2 g, 1.4 mol) and DMF (1000 g) were added, and the mixture was stirred. To the mixture, TBDMCl (150.5 g, 1 mol) was added portionwise under controlled temperature. After addition was completed, the mixture was maintained at the same temperature with stirring until the reaction was completed. After work-up, 220 g of desired product was obtained.

Subsequently, the following starting materials were synthesized from TCOD.

Synthesis of the following compound: (3aS,4R,5S, 6aR)-hexahydro-5-(tert-butyldiphenylsilyloxy)-4-(tert-butyldimethylsilyloxymethyl)-2H-cyclopenta[b] furan-2-one

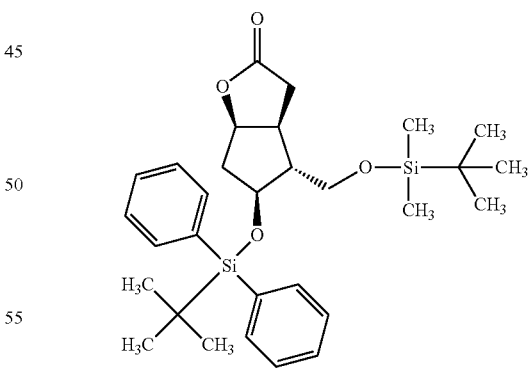

To a reaction bottle under $N_2$, TCOD (286 g, 1 mol), imidazole (95.2 g, 1.4 mol) and DMF (1144 g) were added, and the mixture was stirred at room temperature until it becomes clear. To the solution, tert-butyldiphenylchlorosilane (330 g, 1.2 mol) was added portionwise. After addition was completed, the reaction mixture was maintained at the same temperature until the reaction was completed. After work-up, the mixture was purified by column chromatography, to give 515 g of desired product.

NMR (CDCl$_3$, 500 MHz) $^1$HNMR: δ=−0.02 (s, 6H), 0.87 (s, 9H), 1.09 (s, 9H), 2.01 (m, 1H), 2.05 (m, 1H), 2.14 (m, 1H), 2.64 (m, 2H), 2.80 (m, 1H), 3.3. (m, 1H), 3.44 (m, 1H), 4.15 (m, 1H), 4.84 (m, 1H) 7.39 (m, 6H) 7.69 (m, 4H);

$^{13}$CNMR: δ=−5.61, 18.10, 18.97, 25.83, 26.75, 35.89, 39.90, 41.05, 57.24, 63.34, 76.36, 84.52, 127.57, 129.72, 133.58, 135.83, 177.08.

Synthesis of the following compound: (3aS,4R,5S,6aR)-hexahydro-5-(biphenyl-4-formyloxy)-4-(tert-butyldimethylsilyloxymethyl)-2H-cyclopenta[b]furan-2-one

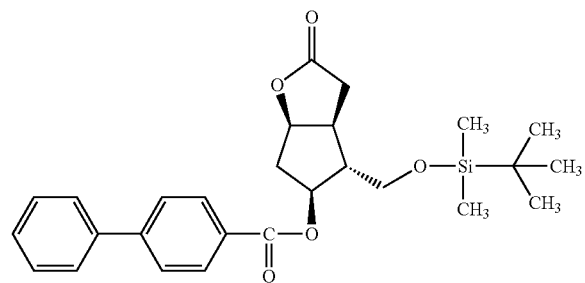 [SMILES: CC(C)(C)[Si](C)(C)OC[C@H]1[C@@H]2CC(=O)O[C@@H]2C[C@@H]1OC(=O)c1ccc(-c2ccccc2)cc1]

To a reaction bottle under N$_2$, TCOD (286 g, 1 mol), imidazole (95.2 g, 1.4 mol) and DMF (1144 g) were added, and the mixture was stirred at room temperature until it becomes clear. To the solution, biphenyl-4-formyl chloride (239 g, 1.1 mol) was added portionwise. After addition was completed, the reaction mixture was maintained at the same temperature until the reaction was completed. After work-up, 343 g of desired product was obtained.

NMR (CDCl$_3$, 500 MHz) $^1$HNMR: δ=0.08 (s, 6H), 0.91 (s, 9H), 2.35 (m, 2H), 2.49 (m, 1H), 2.59 (m, 1H), 2.92 (m, 2H), 3.70 (m, 1H), 3.76 (m, 1H), 5.11 (m, 1H), 5.38 (m, 19H), 7.74 (m, 9H);

$^{13}$CNMR: δ=−5.35, 18.37, 26.05, 36.45, 39.28, 40.74, 55.37, 63.64, 78.99, 85.65, 127.40, 128.34, 128.72, 129.11, 130.36, 140.15, 146.08, 166.10, 177.10.

Synthesis of the following compound: (3aS,4R,5S,6aR)-hexahydro-5-benzoyloxy-4-(tert-butyldimethylsilyloxymethyl)-2H-cyclopenta[b]furan-2-one

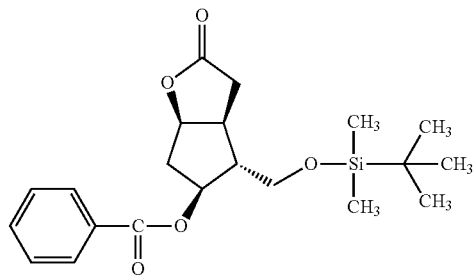 [SMILES: CC(C)(C)[Si](C)(C)OC[C@H]1[C@@H]2CC(=O)O[C@@H]2C[C@@H]1OC(=O)c1ccccc1]

To a reaction bottle under N$_2$, TCOD (286 g, 1 mol), imidazole (95.2 g, 1.4 mol) and DMF (1144 g) were added, and the mixture was stirred at room temperature until it becomes clear. To the solution, benzoyl chloride (239 g, 1.1 mol) was added dropwise. After addition was completed, the reaction mixture was maintained at the same temperature until the reaction was completed. After work-up, the mixture was purified by column chromatography, to give 300 g of desired product.

NMR (CDCl$_3$, 500 MHz) $^1$HNMR: δ=0.02 (s, 6H), 0.86 (s, 9H), 2.28 (m, 2H), 2.43 (m, 1H), 2.51 (m, 1H), 2.87 (m, 2H), 3.64 (m, 1H), 3.70 (m, 1H), 5.03 (m, 1H), 5.28 (m, 1H) 7.67 (m, 5H);

$^{13}$CNMR: δ=−5.53, 18.18, 25.88, 36.21, 39.05, 40.55, 55.12, 63.45, 78.78, 85.38, 128.43, 129.72, 133.05, 165.96, 176.85.

Example 1

Preparation of (3aS,4R,5S,6aR)-5-(tert-butyldimethylsilyloxy)-4-(tert-butyldimethylsilyloxy-methyl)-hexahydro-cyclopenta[b]furan-2-ol (Compound 2a; R$_1$=R$_2$=t-BuMe$_2$Si)

The synthesis was performed by the method of reference example 1 disclosed in EP134153, to afford 7.55 g (94%) of title compound as white solid. MS 402.3.

According to similar methods, using the starting materials for preparation of Compound 2 as described above, various compounds of formula 2 wherein R$_1$ and R$_2$ are various types of protective groups such as cyclic ether protective groups, silyl protective groups or acyl protective groups were prepared.

Example 2

Preparation of (1R,3R,4S)-4-(tert-butyldimethylsilyloxy)-3-[(tert-butyldimethylsilyloxy)methyl]-2-methylene-cyclopentyl formate (Compound 3a; R$_1$=R$_2$=t-BuMe$_2$Si)

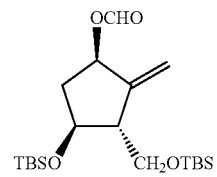

1.23 g (3 mmol) Compound 2a (R$_1$=R$_2$=t-BuMe$_2$Si), 2.65 g Pb(OAc)$_4$ (6 mmol) and 0.1 g anhydrous Cu(OAc)$_2$ (0.2 mmol) were added into 100 ml toluene and 0.5 ml pyridine (6.1 mmol). The mixture was heated to reflux with stirring for 1 hour, and then was cooled to room temperature, filtered with Celite. The filter cake was washed with petroleum ether/ethyl acetate (50/1), and the filtrate was washed with water before dried with Na$_2$SO$_4$. Then the mixture was filtered and the filtrate was evaporated to dryness, to give 1.1 g of residue. The residue was purified with short column filled with 10 g silica gel, eluting with petroleum ether/ethyl acetate (50/1, v/v), to afford 0.74 g (62%) of title compound as colorless oil.

$^1$HNMR (CDCl$_3$, 300 MHz): δ=0.02, 0.03, 0.05, 0.058 (s, each 3H, 4XCH$_3$—), 0.87 (s, 18H), 1.7 (m, 1H), 2.4 (m, 1H), 2.58 (m, 1H), 3.68 (d, J=4.5 Hz, 2H, —CH$_2$—O), 4.12 (m, 1H), 5.19 (t, 1H, J=1.8 Hz), 5.21 (t, 1H, J=1.8 Hz), 5.47 (t, 1H, J=7.5 Hz), 8.11 (s, 1H).

Example 3

According to the method similar to Example 2, using various corresponding starting materials for preparation of Compound 2 as described above, the following compounds were prepared:

| Compound name | Structure | MS data |
|---|---|---|
| 3c: (1R,3R,4S)-4-(tert-butyldiphenylsilyloxy)-3-(tert-butyldiphenylsilyloxymethyl)-2-methylene-cyclopentyl formate | 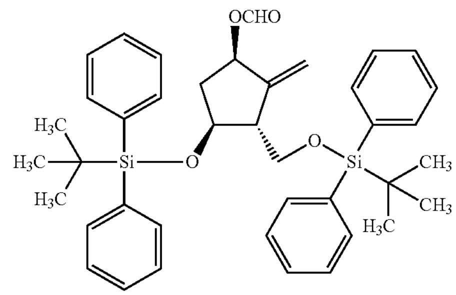 | 648.31 |
| 3d: (1R,3R,4S)-4-(tert-butyldiphenylsilyloxy)-3-(tert-butyldimethylsilyloxymethyl)-2-methylene-cyclopentyl formate | 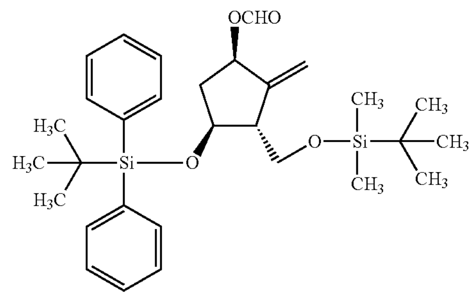 | 524.28 |
| 3e: (1R,3R,4S)-4-tert-butyldimethylsilyloxy-3-(tert-butyl-diphenylsilyloxymethyl)-2-methylene-cyclopentyl formate | 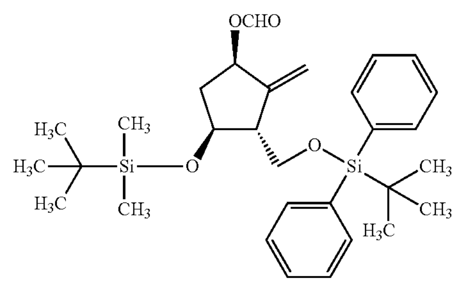 | 524.28 |
| 3f: (1R,3R,4S)-4-tert-butyldimethylsilyloxy-3-(biphenyl-4-formyloxymethyl)-2-methylene-cyclopentyl formate | 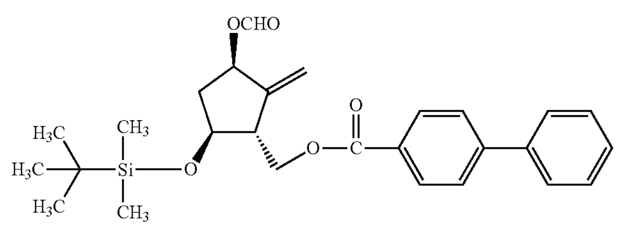 | 466.22 |
| 3g: (4aR,6R,7aS)-2,2-di-tert-butyl-5-methylene-6H-hexahydro-cyclopenta[d][1,3,2]dioxasilin-6-yl formate | 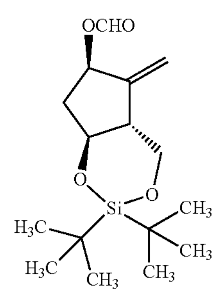 | 312.18 |

-continued

| Compound name | Structure | MS data |
|---|---|---|
| 3h: (1R,3R,4S)-4-(tert-butyldiphenylsilyloxy)-3-(biphenyl-4-formyloxymethyl)-2-methylene-cyclopentyl formate | 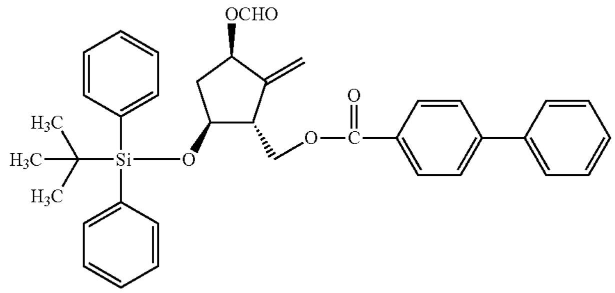 | 590.25 |
| 3i: (1R,3R,4S)-4-(biphenyl-4-formyloxy)-3-(tert-butyldimethylsilyloxymethyl)-2-methylene-cyclopentyl formate | 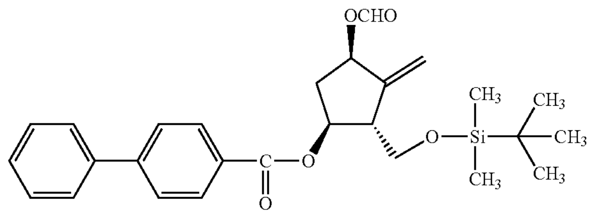 | 466.22 |
| 3j: (1R,3R,4S)-4-benzoyloxy-3-(tert-butyldimethylsilyloxymethyl)-2-methylene-cyclopentyl formate | 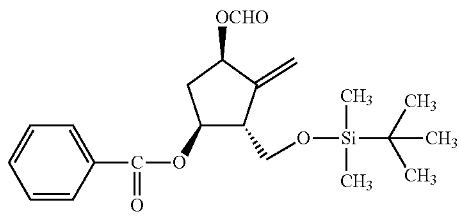 | 390.19 |
| 3k: (2R,4aR,6S,7aS)-2-methyl-5-methylene-6H-tetrahydro-cyclopenta[1,3]dioxan-6-yl formate | 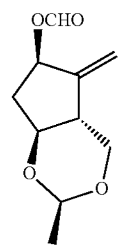 | 198.09 |
| 3l: (1R,3R,4S)-4-(tetrahydropyran-2-yloxy)-3-(tert-butyldimethylsilyloxymethyl)-2-methylene-cyclopentyl formate | 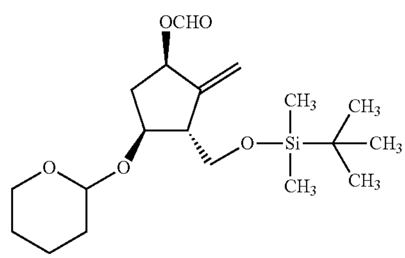 | 370.22 |
| 3m: (1R,3R,4S)-4-(tetrahydropyran-2-yloxy)-3-(tert-butyldiphenylsilyloxymethyl)-2-methylene-cyclopentyl formate | 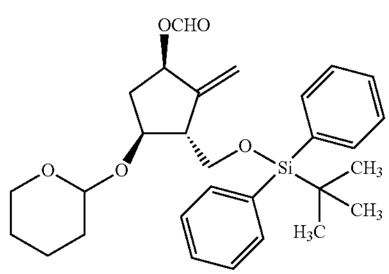 | 494.25 |

-continued

| Compound name | Structure | MS data |
|---|---|---|
| 3n: (1R,3R,4S)-4-(biphenyl-4-formyloxy)-3-(tert-butyldiphenylsilyloxymethyl)-2-methylene-cyclopentyl formate | 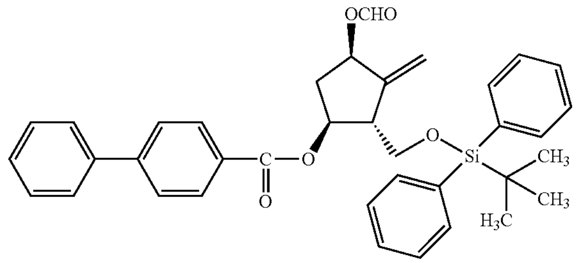 | 590.25 |
| 3o: (1R,3R,4S)-4-benzoyloxy-3-(tert-butyldiphenylsilyloxymethyl)-2-methylene-cyclopentyl formate | 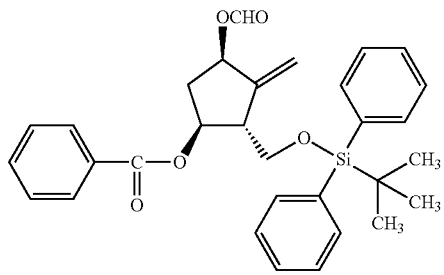 | 514.22 |
| 3p: (1R,3R,4S)-4-benzoyloxy-3-(benzoyloxymethyl)-2-methylene-cyclopentyl formate | 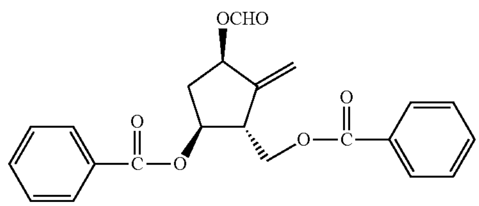 | 380.13 |
| 3q: (1R,3R,4S)-4-(tetrahydropyran-2-yloxy)-3-(benzoyloxymethyl)-2-methylene-cyclopentyl formate | 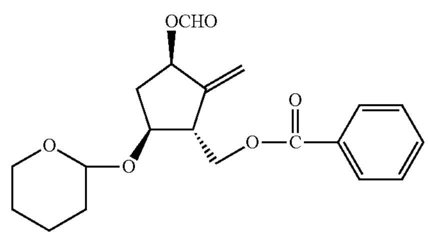 | 360.16 |
| 3r: (1R,3R,4S)-4-tert-butyldimethylsilyloxy-3-(benzoyloxymethyl)-2-methylene-cyclopentyl formate | 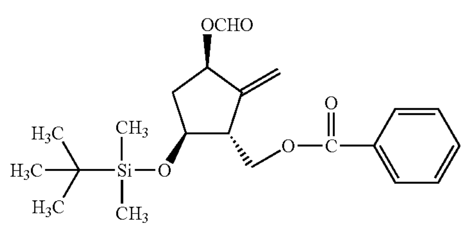 | 390.19 |
| 3s: (1R,3R,4S)-4-(tert-butyldiphenylsilyloxy)-3-(benzoyloxymethyl)-2-methylene-cyclopentyl formate | 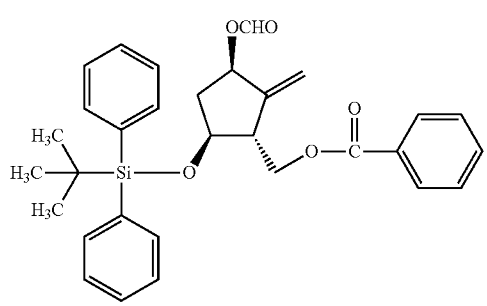 | 514.22 |

-continued

| Compound name | Structure | MS data |
| --- | --- | --- |
| 3t: (1R,3R,4S)-4-(biphenyl-4-formyloxy)-3-(benzoyloxymethyl)-2-methylene-cyclopentyl formate | 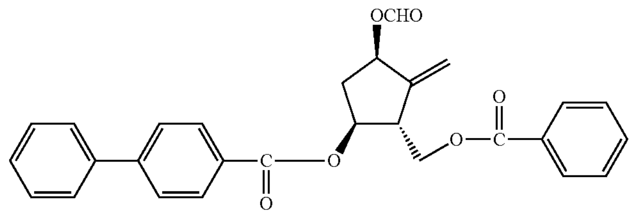 | 456.16 |
| 3u: (1R,3R,4S)-4-benzoyloxy-3-(biphenyl-4-formyloxymethyl)-2-methylene-cyclopentyl formate | 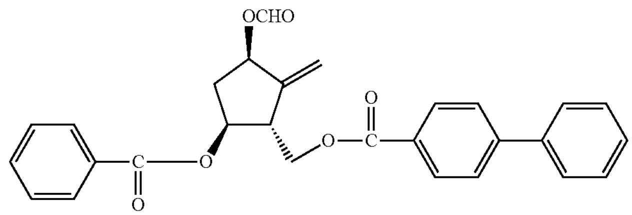 | 456.16 |
| 3v: (1R,3R,4S)-4-(tetrahydropyran-2-yloxy)-3-(biphenyl-4-formyloxymethyl)-2-methylene-cyclopentyl formate | 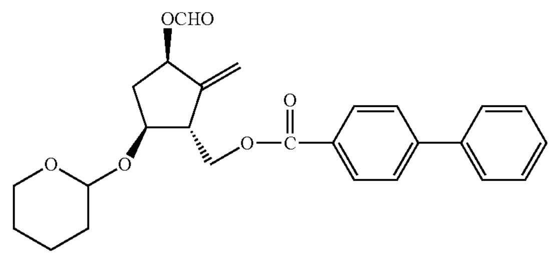 | 436.19 |
| 3w: (1R,3R,4S)-4-(biphenyl-4-formyloxy)-3-(tetrahydropyran-2-yloxymethyl)-2-methylene-cyclopentyl formate | 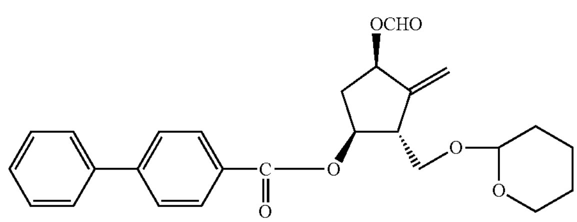 | 436.19 |
| 3x: (1R,3R,4S)-4-tert-butyldimethylsilyloxy-3-(tetrahydropyran-2-yloxymethyl)-2-methylene-cyclopentyl formate | 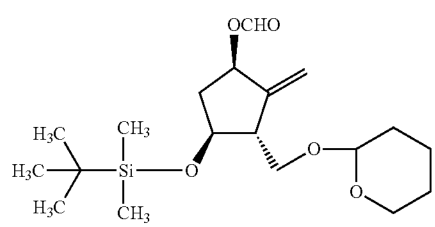 | 370.22 |
| 3y: (1R,3R,4S)-4-(biphenyl-4-formyloxy)-3-(biphenyl-4-formyloxymethyl)-2-methylene-cyclopentyl formate | 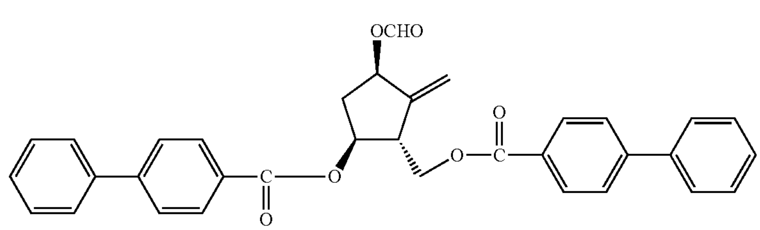 | 532.19 |

| Compound name | Structure | MS data |
|---|---|---|
| 3z: (2S,4aR,6S,7aS)-2-methyl-5-methylene-6H-tetrahydro-cyclopenta[1,3]dioxan-6-yl formate | 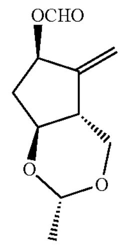 | 198.09 |

Among these compounds, the NMR data of Compound 3k was shown below.

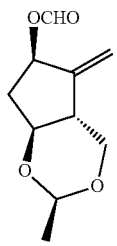

NMR (CDCl$_3$, 500 MHz): $^1$HNMR: δ=1.34 (d, 3H), 1.76 (m, 1H), 2.51 (m, 1H), 2.63 (m, 1H), 3.23 (m, 1H), 3.59 (m, 1H), 4.36 (m, 1H), 4.67 (m, 1H), 4.90 (s, 1H), 5.22 (d, 1H), 5.50 (t, 1H), 8.03 (s, 1H);

$^{13}$CNMR: δ=20.78, 36.04, 45.16, 68.64, 71.75, 78.59, 100.02, 113.04, 144.77, 160.79.

Example 4a

Preparation of (1R,3R,4S)-4-(tert-butyldimethylsilyloxy)-3-[(tert-butyldimethylsilyloxy)methyl]-2-methylene-cyclopentanol (Compound 4a; R$_1$=R$_2$=t-BuMe$_2$Si)

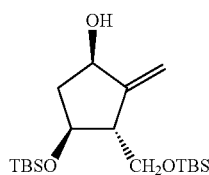

To 490 mg (1.22 mmol) of Compound 3a (R$_1$=R$_2$=t-BuMe$_2$Si), 15 ml methanol and 250 mg anhydrous K$_2$CO$_3$ were added. The mixture was stirred at room temperature for 1 hour, and evaporated to dryness under reduced pressure. To the residue, 20 ml petroleum ether and 15 ml water were added, and the mixture was stirred for 15 min. The organic layer was isolated, washed with saturated NaCl solution, dried with anhydrous Na$_2$SO$_4$, and filtered. The filtrate was evaporated to dryness, to give 440 mg (96%) of title compound as white solid. mp 64-66° C.

$^1$HNMR (CDCl$_3$, 300 MHz): δ=0.02 (s, 3H), 0.04 (s, 3H), 0.09 (s, 6H), 0.88 (s, 18H), 1.8 (dd, J=1.8, 12 Hz, 1H), 1.99 (m, 1H), 2.75 (m, 1H), 3.30 (dd, 1H, J=8, 7, 10 Hz), 3.56 (dd, 1H, J=5.1, 10 Hz), 4.36 (m, 2H), 5.12 (d, 1H, J=1 Hz), 5.38 (d, 1H, J=1 Hz).

Example 4b

Preparation of (1R,3R,4S)-4-benzyloxy-3-(benzyloxymethyl)-2-methylene-cyclopentanol (Compound 4b; R$_1$=R$_2$=benzyl)

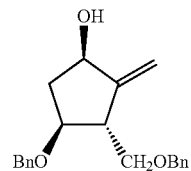

Title compound was prepared according to the methods similar to Examples 1 to 4a.

$^1$HNMR (CDCl$_3$, 300 MHz): δ=1.92 (m, 1H), 2.0-2.1 (m, 1H), 3.07 (m, 1H), 3.30 (t, J=9 Hz, 1H), 3.45 (m, 1H), 4.06 (m, 1H), 4.4 (m, 1H), 4.48 (dd, 2H), 4.53 (s, 2H), 5.14 (s, 1H), 5.37 (s, 1H), 7.29-7.36 (m, 10H).

According to the methods similar to Examples 4a and 4b, the following compounds can also be prepared:

Compound 4c: (1R,3R,4S)-4-(tert-butyldiphenylsilyloxy)-3-(tert-butyldiphenylsilyloxymethyl)-2-methylene-1-cyclopentanol

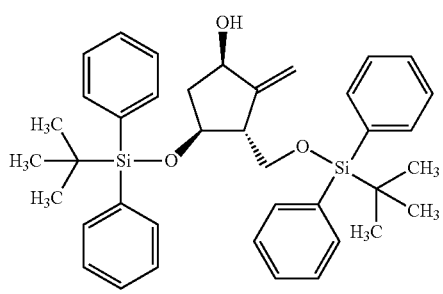 [SMILES: C=C1[C@H](O)C[C@H](O[Si](c2ccccc2)(c2ccccc2)C(C)(C)C)[C@H]1CO[Si](c1ccccc1)(c1ccccc1)C(C)(C)C]

NMR (CDCl$_3$, 500 MHz)

1HNMR: δ=1.03 (s, 9H), 1.17 (s, 9H), 1.94 (m, 1H), 2.05 (m, 1H), 2.93 (m, 1H), 3.02 (m, 1H), 3.51 (m, 2H), 4.43 (m, 1H), 4.49 (m, 1H), 5.22 (m, 1H), 5.48 (m, 1H), 7.49 (m, 20H);

13CNMR: δ=19.20, 19.29, 26.88, 27.19, 42.99, 54.65, 65.24, 74.96, 76.04, 111.43, 127.75, 127.87, 129.76, 129.94, 133.44, 133.70, 135.74, 135.47, 154.66

Compound 4d: (1R,3R,4S)-4-(tert-butyldiphenylsilyloxy)-3-(tert-butyldimethylsilyloxymethyl)-2-methylene-1-cyclopentanol

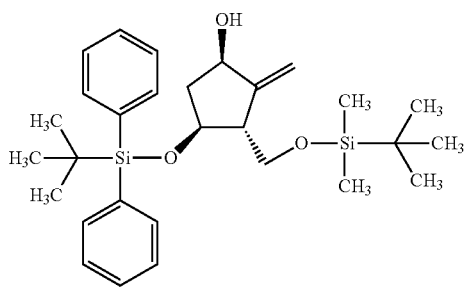 [SMILES: C=C1[C@H](O)C[C@H](O[Si](c2ccccc2)(c2ccccc2)C(C)(C)C)[C@H]1CO[Si](C)(C)C(C)(C)C]

NMR (CDCl$_3$, 500 MHz)
$^1$HNMR: δ=−0.01 (s, 6H), 0.85 (s, 9H), 1.18 (s, 9H), 1.92 (m, 1H), 2.05 (m, 1H), 2.91 (m, 1H), 3.06 (m, 1H), 3.45 (m, 2H), 4.39 (m, 2H), 5.21 (m, 1H), 5.43 (m, 1H), 7.60 (m, 10H);
13CNMR: δ=−5.44, 18.32, 19.18, 26.00, 27.17, 42.95, 54.68, 64.42, 74.67, 75.48, 110.73, 127.72, 129.87, 133.78, 135.93, 154.65

Compound 4e: (1R,3R,4S)-4-tert-butyldimethylsilyloxy-3-(tert-butyldiphenylsilyloxymethyl)-2-methylene-1-cyclopentanol

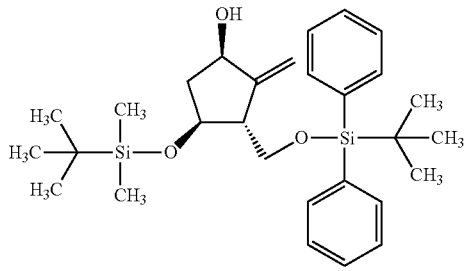 [SMILES: C=C1[C@H](O)C[C@H](O[Si](C)(C)C(C)(C)C)[C@H]1CO[Si](c1ccccc1)(c1ccccc1)C(C)(C)C]

NMR (CDCl$_3$, 500 MHz)
1HNMR: δ=0.20 (s, 6H), 0.97 (s, 9H), 1.18 (s, 9H), 1.89 (m, 1H), 2.09 (m, 1H), 2.92 (m, 1H), 3.20 (m, 1H), 3.56 (m, 1H), 3.75 (m, 1H), 4.45 (m, 1H), 4.52 (m, 1H), 5.16 (m, 1H), 5.46 (m, 1H), 7.61 (m, 10H);
13CNMR: δ=−4.57, 18.01, 19.32, 25.95, 26.81, 42.56, 54.95, 65.28, 74.76, 77.27, 111.63, 127.80, 129.85, 133.43, 135.72, 154.11

Compound 4f: (1R,3R,4S)-4-tert-butyldimethylsilyloxy-3-(biphenyl-4-formyloxymethyl)-2-methylene-1-cyclopentanol

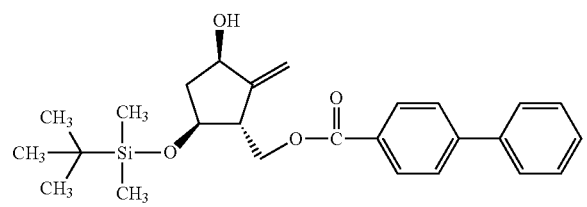 [SMILES: C=C1[C@H](O)C[C@H](O[Si](C)(C)C(C)(C)C)[C@H]1COC(=O)c1ccc(-c2ccccc2)cc1]

NMR (CDCl$_3$, 500 MHz)
$^1$HNMR: δ=0.11 (s, 6H), 0.92 (s, 9H), 1.88 (m, 1H), 2.22 (m, 1H), 3.07 (m, 1H), 3.10 (m, 1H), 4.30 (m, 3H), 4.48 (m, 1H), 5.29 (m, 1H), 5.49 (m, 1H), 7.73 (m, 9H);
$^{13}$CNMR: δ=−4.75, 17.91, 25.79, 42.58, 51.43, 65.22, 74.12, 112.27, 127.15, 127.23, 128.21, 128.72, 128.94, 130.08, 139.80, 145.75, 152.68, 166.32

Compound 4g: (4aR,6R,7aS)-2,2-di-tert-butyl-5-methylene-6-hydroxy-6H-tetrahydro-cyclopenta[d][1,3,2]dioxasiline

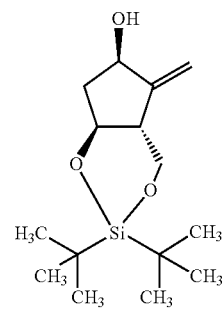 [SMILES: C=C1[C@H](O)C[C@@H]2O[Si](C(C)(C)C)(C(C)(C)C)OC[C@@H]12]

NMR (CDCl$_3$, 500 MHz)
$^1$HNMR: δ=0.99 (s, 18H), 1.60 (s, 1H), 2.11 (m, 1H), 2.59 (m, 1H), 2.80 (m, 1H), 3.86 (m, 2H), 4.48 (m, 2H), 4.84 (m, 1H), 5.18 (m, 1H);
$^{13}$CNMR: δ=20.17, 22.87, 27.42, 27.65, 42.25, 49.65, 67.68, 71.04, 75.03, 110.26, 150.75

Compound 4h: (1R,3R,4S)-4-(tert-butyldiphenylsilyloxy)-3-(biphenyl-4-formyloxymethyl)-2-methylene-1-cyclopentanol

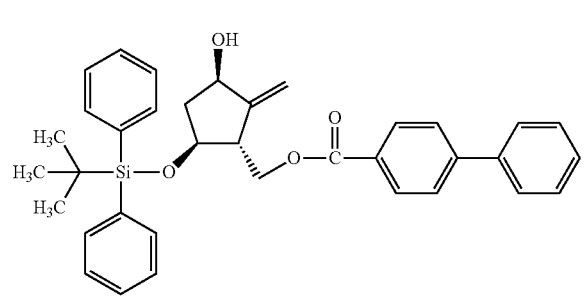 [SMILES: C=C1[C@H](O)C[C@H](O[Si](c2ccccc2)(c2ccccc2)C(C)(C)C)[C@H]1COC(=O)c1ccc(-c2ccccc2)cc1]

NMR (CDCl$_3$, 500 MHz)
$^1$HNMR: δ=1.13 (s, 9H), 1.93 (s, 2H), 2.20 (m, 1H), 3.17 (m, 1H), 3.61 (m, 1H), 4.04 (m, 1H), 4.19 (m, 1H), 4.35 (m, 1H), 5.23 (m, 1H), 5.44 (m, 1H), 7.59 (m, 19H):
$^{13}$CNMR: δ=18.75, 26.71, 42.59, 51.04, 64.23, 72.62, 73.35, 110.73, 126.74, 127.51, 127.90, 128.57, 129.73, 133.10, 135.48, 139.51, 145.19, 152.34, 165.73, 170.57

Compound 4i: (1R,3R,4S)-4-(biphenyl-4-formyloxy)-3-(tert-butyldimethylsilyloxymethyl)-2-methylene-1-cyclopentanol

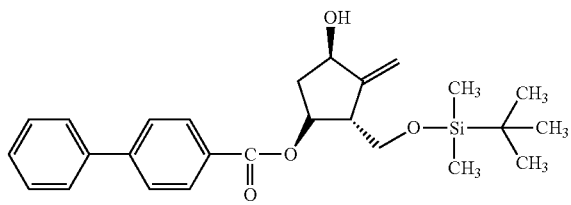

NMR (CDCl₃, 500 MHz)
¹HNMR: δ=0.05 (s, 6H), 0.07 (s, 6H), 0.90 (s, 9H), 1.94 (m, 2H), 2.61 (m, 1H), 3.01 (m, 1H), 3.71 (m, 1H), 3.88 (m, 1H), 4.58 (m, 1H), 5.21 (m, 1H), 5.41 (m, 2H), 7.69 (m, 9H);
¹³CNMR: δ=−5.26, 18.48, 26.10, 41.11, 51.70, 64.97, 74.11, 110.40, 127.28, 127.51, 128.38, 129.16, 129.26, 130.34, 140.22, 145.94, 154.04, 166.27

Compound 4j: (1R,3R,4S)-4-benzoyloxy-3-(tert-butyldimethylsilyloxymethyl)-2-methylene-1-cyclopentanol

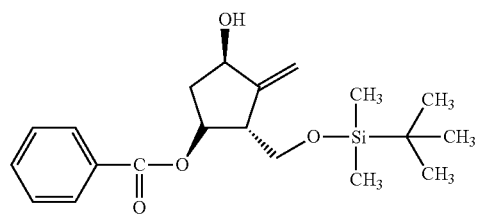

NMR (CDCl₃, 500 MHz)
¹HNMR: δ=0.04 (s, 6H), 0.87 (s, 9H), 1.89 (m, 1H), 2.22 (m, 1H), 2.58 (m, 1H), 2.96 (m, 1H), 3.67 (m, 1H), 3.84 (m, 1H), 4.55 (m, 1H), 5.17 (m, 1H), 5.35 (m, 2H), 7.71 (m, 5H);
¹³CNMR: δ=−5.33, 18.40, 26.03, 40.98, 51.55, 64.88, 73.84, 76.25, 110.18, 128.52, 129.76, 130.47, 133.13, 153.83, 166.36

Compound 4k: (2R,4aR,6S,7aS)-2-methyl-5-methylene-6-hydroxy-6H-tetrahydro-cyclopenta[1,3]dioxane

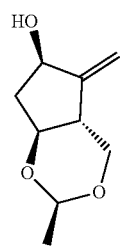

NMR (CDCl₃, 500 MHz)
¹HNMR: δ=1.25 (s, 3H), 1.58 (m, 1H), 2.46 (m, 2H), 3.12 (m, 1H), 3.39 (m, 1H), 3.52 (m, 1H), 4.29 (m, 2H), 4.61 (m, 1H), 4.77 (m, 1H), 5.09 (m, 1H);
¹³CNMR: δ=20.71, 38.76, 45.04, 68.77, 70.59, 78.44, 99.87, 109.99, 148.22

Compound 4l: (1R,3R,4S)-4-(tetrahydropyran-2-yloxy)-3-(tert-butyldimethylsilyloxymethyl)-2-methylene-1-cyclopentanol

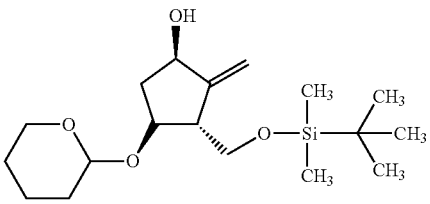

NMR (CDCl₃, 500 MHz)
¹HNMR: δ=0.01 (m, 6H), 0.84 (s, 9H), 1.48 (m, 3H), 1.51 (m, 1H), 1.70 (m, 2H), 1.88 (m, 1H), 2.13 (m, 1H), 2.77 (m, 1H), 3.60 (m, 5H), 4.24 (m, 2H), 4.65 (m, 2H), 5.06 (m, 1H), 5.28 (d, 2H);
¹³CNMR: δ=−5.36, 18.36, 19.62, 25.71, 31.05, 38.46, 41.17, 52.09, 65.16, 62.88, 64.75, 74.62, 78.76, 96.66, 110.44, 154.16

Example 5

Preparation of Compounds 5a-5e

As described above, the compounds of formula 5 have the following general formula:

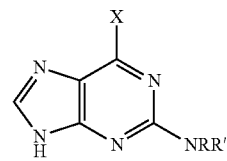

wherein
Compound 5a: X=Cl, R=H, R'=Boc;
Compound 5b: X=OMe, R=H, R'=Boc;
Compound 5c: X=OBn, R=H, R'=Boc;
Compound 5d: X=Cl, R=Boc, R'=Boc;
Compound 5e: X=OBu-t, R=H, R'=Boc.

Compound 5a was prepared according to the method described in J. Org. Chem. 2000, 65, 7697-7699.

Compound 5a

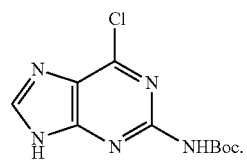 [SMILES: CC(C)(C)OC(=O)Nc1nc(Cl)c2nc[nH]c2n1]

Compounds 5b, 5c and 5d were prepared according to the methods similar to the method for preparation of Compound 5a, and Compound 5e was prepared according to the method described in Org. Lett., 2009, 11, 2465.

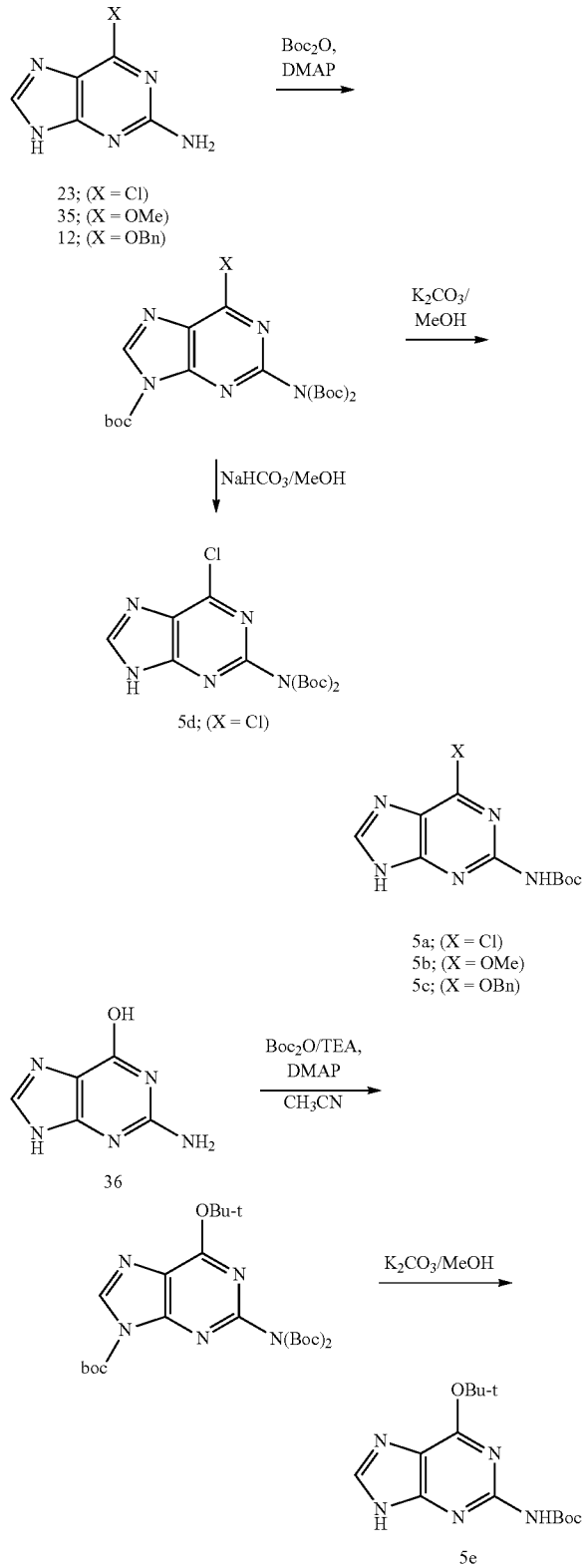

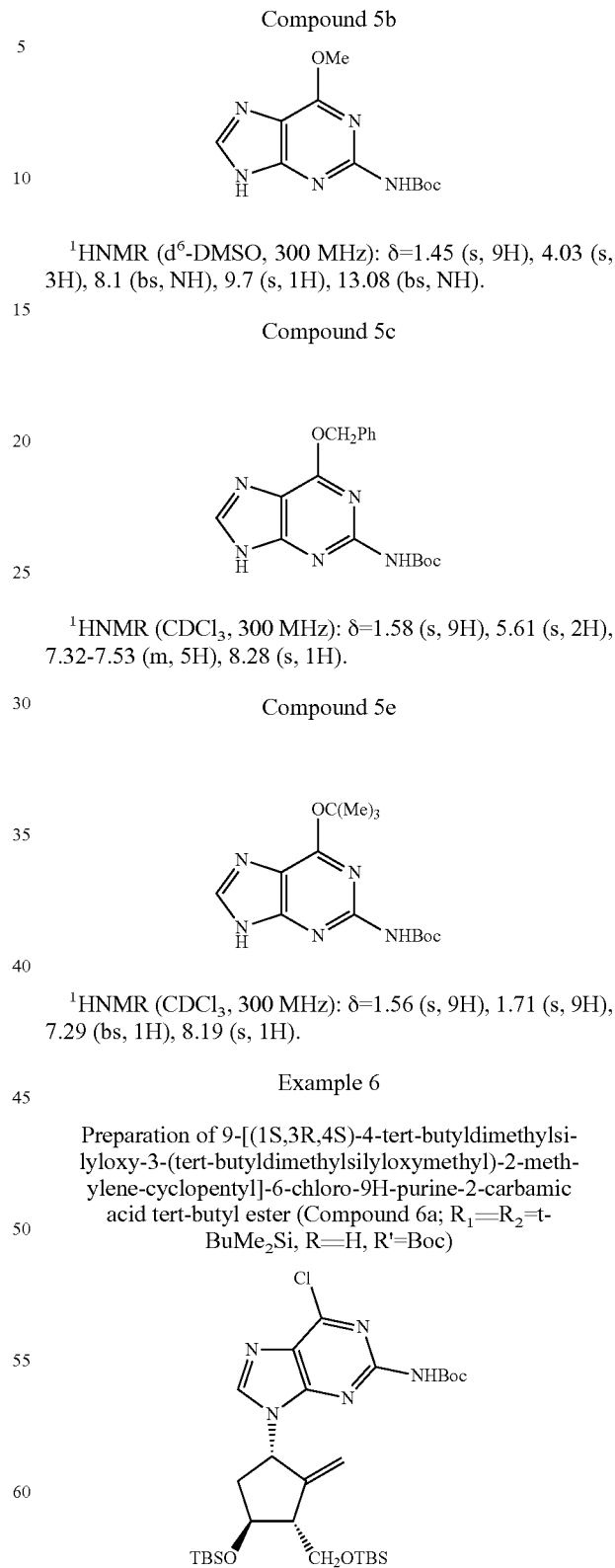

The physical data of Compounds 5b, 5c and 5e obtained were shown below:

Compound 5b

¹HNMR (d⁶-DMSO, 300 MHz): δ=1.45 (s, 9H), 4.03 (s, 3H), 8.1 (bs, NH), 9.7 (s, 1H), 13.08 (bs, NH).

Compound 5c

¹HNMR (CDCl₃, 300 MHz): δ=1.58 (s, 9H), 5.61 (s, 2H), 7.32-7.53 (m, 5H), 8.28 (s, 1H).

Compound 5e

¹HNMR (CDCl₃, 300 MHz): δ=1.56 (s, 9H), 1.71 (s, 9H), 7.29 (bs, 1H), 8.19 (s, 1H).

Example 6

Preparation of 9-[(1S,3R,4S)-4-tert-butyldimethylsilyloxy-3-(tert-butyldimethylsilyloxymethyl)-2-methylene-cyclopentyl]-6-chloro-9H-purine-2-carbamic acid tert-butyl ester (Compound 6a; R₁=R₂=t-BuMe₂Si, R=H, R'=Boc)

186 mg (0.5 mmol) Compound 4a (R₁=R₂=t-BuMe₂Si), 200 mg (0.75 mmol) Compound 5a (R=H, R'=Boc) and 156 mg Ph₃P (0.75 mmol) were placed in 50 ml round bottom flask, to which 8 ml anhydrous THF was added. The reaction mixture was cooled to −23° C., to which 0.17 ml DEAD (1.0 mmol) was then added dropwise. After addition was completed, the reaction mixture was stirred at −23° C. for 3.5 hours. TLC showed the dot of starting material disappeared. 3 drops of water were added. The reaction mixture was warmed to room temperature, and then THF was evaporated off under reduced pressure. 5 ml t-BuOMe was added, the mixture was stirred for 5 min, and 15 ml n-hexane was added. The mixture was maintained standing for 5 hours, and filtered to remove insoluble substance. The filtrate was purified with column chromatography, eluting with petroleum ether/EtOAc (10/1, v/v), to afford 320 mg (~100%) of title compound as colorless syrup.

¹HNMR (CDCl₃, 300 MHz): δ=0.08 (s, 3H), 0.09 (s, 3H), 0.10 (s, 6H), 0.90 (s, 9H), 0.92 (s, 9H), 1.54 (s, 9H), 2.23 (m, 1H), 2.33 (m, 1H), 2.66 (m, 1H), 3.83 (d, 2H, J=5.4 Hz), 4.45 (m, 1H), 4.82 (s, 1H), 5.22 (s, 1H), 5.64 (t, 1H, J=8.1), 7.38 (s, 1H), 8.03 (s, 1H).

Example 7

Preparation of 9-[(1S,3R,4S)-4-tert-butyldimethylsilyloxy-3-(tert-butyldimethylsilyloxymethyl)-2-methylene-cyclopentyl]-6-chloro-N-(tert-butyloxycarbonyl)-9H-purine-2-carbamic acid tert-butyl ester [Compound 6d; R₁=R₂=t-BuMe₂Si, R=Boc, R'=Boc]

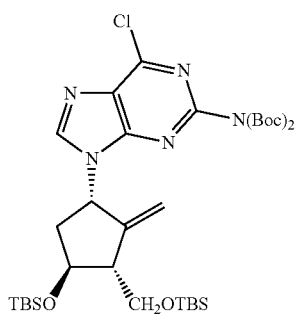

640 mg (1.72 mmol) Compound 4a (R₁=R₂=t-BuMe₂Si), 888 mg (2.4 mmol) Compound 5d [R=Boc, R'=Boc] and 607 mg Ph₃P (2.32 mmol) were placed in 50 ml round bottom flask, to which 20 ml anhydrous THF was added. The reaction mixture was cooled to −23° C., to which 0.5 ml (2.75 mmol) DEAD was then added dropwise. After addition was completed, the reaction mixture was stirred at −23° C. for 2 hours, stirred at room temperature for 12 hours, and then THF was evaporated off under reduced pressure. 150 ml n-hexane was added. The mixture was maintained standing for 5 hours, and filtered to remove insoluble substance. The filtrate was purified with column chromatography, eluting with petroleum ether/EtOAc (10/1, v/v), to afford 1.08 g (87%) of title compound as colorless syrup.

¹HNMR (CDCl₃, 300 MHz): δ=0.07 (s, 3H), 0.08 (s, 3H), 0.10 (s, 6H), −0.89- (s, 9H), 0.93 (s, 9H), 1.43 (s, 18H), 2.30 (m, 2H), 2.70 (m, 1H), 3.83 (m, 2H), 4.50 (m, 1H), 4.85 (s, 1H), 5.25 (s, 1S), 5.70 (t, 1H), 8.24 (s, 1H).

Example 8

According to the methods similar to Example 6, Compounds 6b, 6c and 6e were prepared, using Compounds 5b, 5c and 5e as starting materials to perform coupling reaction with Compound 4a. According to the method similar to Example 6, Compound 6f was prepared, using Compound 5a to perform coupling reaction with Compound 4b.

Compound 6b: 9-[(1S,3R,4S)-4-tert-butyldimethylsilyloxy-3-(tert-butyldimethylsilyloxymethyl)-2-methylene-cyclopentyl]-6-methoxy-9H-purine-2-carbamic acid tert-butyl ester

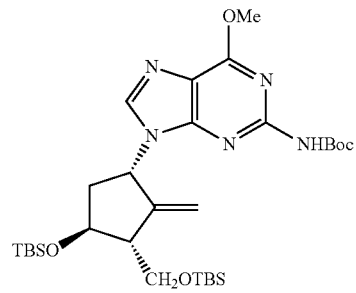

¹HNMR (CDCl₃, 300 MHz): δ=0.001 (s, 12H), 0.11 (s, 3H), 0.19 (s, 6H), 0.90 (s, 6H), 0.92 (s, 6H), 1.54 (s, 6H), 2.27 (m, 2H), 2.65 (m, 1H), 3.81 (d, J=6 Hz, 2H), 4.16 (s, 3H), 4.45 (m, 1H), 4.84 (s, 1H), 5.21 (s, 1H), 5.63 (t, 1H), 7.97 (s, 1H).

Compound 6c: 6-benzyloxy-9-[(1S,3R,4S)-4-tert-butyldimethylsilyloxy-3-(tert-butyldimethylsilyloxymethyl)-2-methylene-cyclopentyl]-9H-purine-2-carbamic acid tert-butyl ester

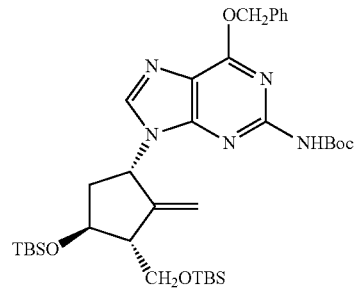

¹HNMR (CDCl₃, 300 MHz): δ=0 (s, 9H), 0.067 (s, 3H), 0.078 (s, 3H), 0.195 (s, 3H), 0.89 (s, 6H), 0.92 (s, 6H), 1.40 (s, 9H), 2.0-2.26 (m, 2H), 2.68 (m, 1H), 3.8 (d, J=4.8 Hz, 2H), 4.44 (bs, 1H), 4.84 (s, 1H), 5.22 (s, 1H), 5.64 (s, 2H), 7.32-7.35 (m, 3H), 7.51-7.53 (m, 2H), 8.1 (s, 1H)

Compound 6e: 6-tert-butyloxy-9-[(1S,3R,4S)-4-tert-butyldimethylsilyloxy-3-(tert-butyldimethylsilyloxymethyl)-2-methylene-cyclopentyl]-9H-purine-2-carbamic acid tert-butyl ester

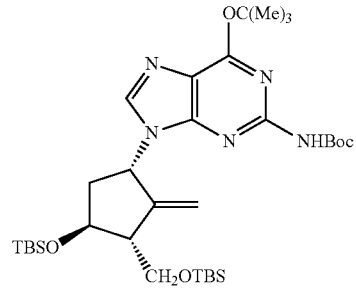

¹HNMR (CDCl₃, 300 MHz): δ=0.01 (s, 6H), 0.09 (s, 6H) 0.86 (s, 12H), 0.88 (s, 12H), 1.54 (s, 6H), 1.63 (s, 6H), 2.19 (m, 2H), 2.68 (m, 1H), 3.77 (m, 2H), 4.43 (bs, 1H), 4.81 (s, 1H), 5.18 (s, 1H), 5.41 (m, 1H), 7.68 (s, 1H)

Compound 6f: 9-[(1S,3R,4S)-4-benzyloxy-3-(benzyloxymethyl)-2-methylene-cyclopentyl]-6-chloro-9H-purine-2-carbamic acid tert-butyl ester

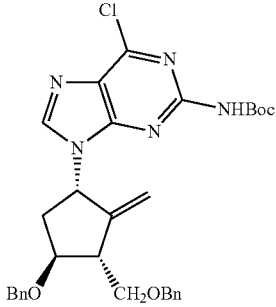

¹HNMR (CDCl₃, 300 MHz): δ=1.53 (s, 9H), 2.52 (m, 2H), 3.0 (bs, 1H), 3.74 (m, 2H), 4.22 (dd, 2H), 4.35 (m, 1H), 4.56 (d, J=6 Hz, 2H), 4.81 (s, 1H), 5.23 (s, 1H), 5.66 (t, 1H), 7.18-7.42 (m, 10H), 8.0 (s, 1H).

According to the methods similar to Example 6, using Compounds 4c to 4l as corresponding starting materials to react with Compound 5a, the following compounds were prepared:

Compound 6g: 9-[(1S,3R,4S)-4-(tert-butyldiphenylsilyloxy)-3-(tert-butyldiphenylsilyloxymethyl)-2-methylene-cyclopentyl]-6-chloro-9H-purine-2-carbamic acid tert-butyl ester

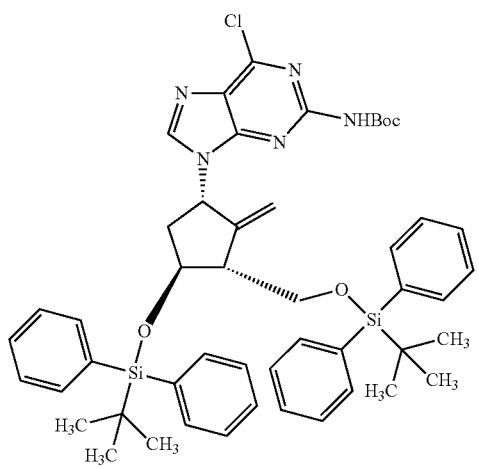 [SMILES: C=C1[C@H](CO[Si](c2ccccc2)(c2ccccc2)C(C)(C)C)[C@@H](O[Si](c2ccccc2)(c2ccccc2)C(C)(C)C)C[C@@H]1n1cnc2c(Cl)nc(NC(=O)OC(C)(C)C)nc21]

NMR (CDCl₃, 500 MHz)
1HNMR: δ=0.99 (s, 9H), 1.12 (s, 9H), 1.55 (s, 9H), 2.04 (m, 1H), 2.10 (m, 1H), 2.91 (m, 1H), 3.61 (m, 2H), 4.51 (m, 1H), 4.78 (m, 1H), 5.17 (m, 1H), 5.83 (m, 1H), 7.49 (m, 21H), 7.81 (s, 1H);
13CNMR: δ=19.23, 19.30, 27.01, 27.14, 28.34, 40.39, 54.47, 56.84, 65.18, 73.86, 81.57, 111.54, 127.88, 127.99, 129.95, 133.02, 133.17, 133.68, 133.80, 133.65, 135.87, 143.47, 149.18, 150.29, 151.23, 152.39, 153.15

Compound 6h: 9-[(1S,3R,4S)-3-(tert-butyldimethylsilyloxymethyl)-4-(tert-butyldiphenylsilyloxy)-2-methylene-cyclopentyl]-6-chloro-9H-purine-2-carbamic acid tert-butyl ester

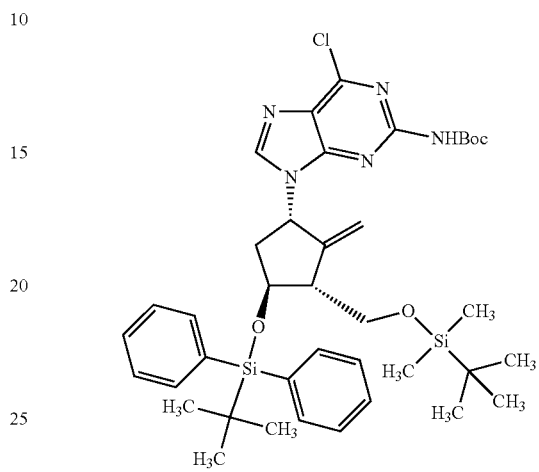

NMR (CDCl₃, 500 MHz)
¹HNMR: δ=−0.04 (s, 6H), 0.83 (s, 9H), 1.11 (s, 9H), 1.55 (m, 9H), 2.12 (m, 1H), 2.28 (m, 1H), 2.77 (m, 1H), 3.55 (m, 1H), 3.66 (m, 1H), 4.40 (m, 1H), 4.84 (m, 1H), 5.22 (m, 1H), 5.77 (m, 1H), 7.48 (m, 1H), 7.92 (s, 1H);
¹³CNMR: δ=−5.31, 18.58, 19.38, 26.16, 27.23, 28.46, 41.13, 84.60, 56.90, 64.62, 74.39, 84.75, 111.88, 127.96, 130.05, 133.87, 133.98, 135.97, 143.87, 149.68, 150.39, 151.25, 152.42, 153.26

Compound 6i: 9-[(1S,3R,4S)-4-tert-butyldimethylsilyloxy-3-(tert-butyldiphenylsilyloxymethyl)-2-methylene-cyclopentyl]-6-chloro-9H-purine-2-carbamic acid tert-butyl ester

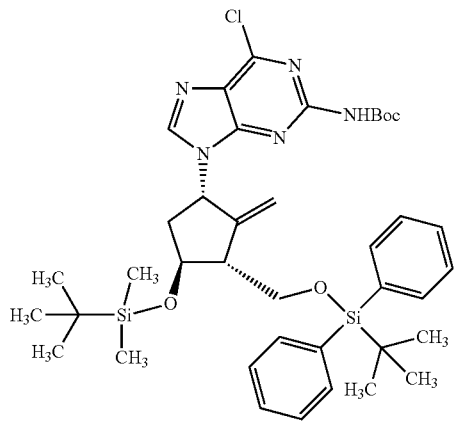 [SMILES: C=C1[C@H](CO[Si](c2ccccc2)(c2ccccc2)C(C)(C)C)[C@@H](O[Si](C)(C)C(C)(C)C)C[C@@H]1n1cnc2c(Cl)nc(NC(=O)OC(C)(C)C)nc21]

NMR (CDCl₃, 500 MHz)
¹HNMR: δ=0.08 (s, 6H), 0.90 (s, 9H), 1.10 (s, 9H), 1.53 (m, 9H), 2.25 (m, 2H), 2.77 (m, 1H), 3.80 (m, 2H), 4.52 (m, 1H), 4.72 (m, 1H), 5.12 (m, 1H), 5.67 (m, 1H), 7.49 (m, 11H), 7.87 (s, 1H);

¹³CNMR: δ=−4.43, 18.21, 19.48, 26.04, 27.20, 28.43, 40.43, 54.99, 56.98, 65.16, 72.47, 81.75, 111.68, 128.13, 130.14, 133.32, 135.81, 135.93, 143.75, 148.98, 150.32, 151.41, 152.40, 153.16

Compound 6j: 9-[(1S,3R,4S)-4-tert-butyldimethylsilyloxy-3-(biphenyl-4-formyloxymethyl)-2-methylene-cyclopentyl]-6-chloro-9H-purine-2-carbamic acid tert-butyl ester

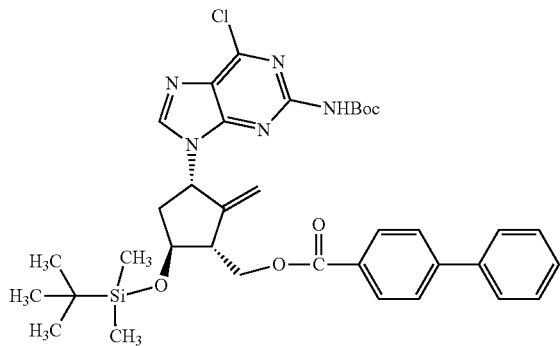 [SMILES: C=C1[C@H](COC(=O)c2ccc(-c3ccccc3)cc2)[C@@H](O[Si](C)(C)C(C)(C)C)C[C@@H]1n1cnc2c(Cl)nc(NC(=O)OC(C)(C)C)nc21]

NMR (CDCl₃, 500 MHz)
¹HNMR: δ=0.11 (s, 6H), 0.91 (s, 9H), 1.52 (s, 9H), 2.22 (m, 1H), 2.76 (m, 1H), 3.08 (m, 1H), 4.60 (m, 2H), 4.72 (m, 1H), 4.83 (m, 1H), 5.33 (m, 1H), 5.63 (m, 1H), 7.49 (m, 8H), 8.01 (s, 1H), 8.12 (m, 2H);
¹³CNMR: δ=−4.52, 18.24, 26.01, 28.40, 39.34, 52.16, 57.68, 65.16, 72.63, 81.65, 112.72, 127.38, 127.50, 128.46, 128.63, 128.83, 129.16, 130.28, 140.06, 144.28, 146.16, 147.82, 150.30, 151.58, 152.35, 152.61, 166.67

Compound 6k: (4aR,6S,7aS)-6-chloro-9-(2,2-di-tert-butyl-5-methylene-hexahydro-cyclopenta[1,3,2]dioxasilin-6-yl)-9H-purine-2-carbamic acid tert-butyl ester

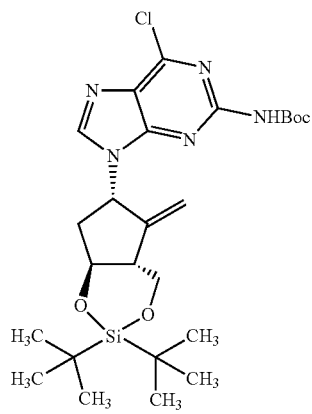 [SMILES: C=C1[C@@H]2CO[Si](C(C)(C)C)(C(C)(C)C)O[C@H]2C[C@@H]1n1cnc2c(Cl)nc(NC(=O)OC(C)(C)C)nc21]

NMR (CDCl₃, 500 MHz)
¹HNMR: δ=1.04 (s, 9H), 1.08 (s, 9H), 1.54 (s, 9H), 2.37 (m, 2H), 2.72 (m, 1H), 4.12 (m, 1H), 4.50 (m, 2H), 4.69 (m, 1H), 4.89 (m, 1H), 5.64 (m, 1H), 7.53 (m, 1H), 7.88 (s, 1H);

¹³CNMR: δ=20.16, 22.95, 27.39, 27.66, 28.45, 40.01, 50.38, 53.81, 67.19, 76.73, 81.87, 110.65, 127.96, 143.36, 146.27, 150.22, 151.57, 152.64, 153.03

Compound 6l: 9-[(1S,3R,4S)-4-(tert-butyldiphenylsilyloxy)-3-(biphenyl-4-formyloxymethyl)-2-methylene-cyclopentyl]-6-chloro-9H-purine-2-carbamic acid tert-butyl ester

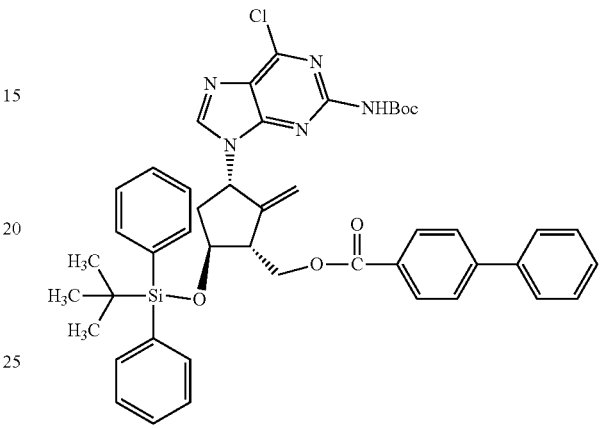

NMR (CDCl₃, 500 MHz)
¹HNMR: δ=1.11 (s, 9H), 1.51 (s, 9H), 2.15 (m, 1H), 2.58 (m, 1H), 3.22 (m, 1H), 4.46 (m, 1H), 4.58 (m, 2H), 4.91 (m, 1H), 5.34 (m, 1H), 5.74 (m, 1H), 7.50 (m, 21H);
¹³CNMR: δ=19.23, 27.06, 28.27, 38.86, 51.84, 57.49, 64.79, 73.59, 81.40, 113.08, 127.13, 127.34, 127.91, 128.31, 128.42, 128.59, 129.05, 130.02, 130.06, 130.18, 133.42, 135.76, 139.96, 144.06, 145.90, 147.59, 150.28, 151.37, 152.27, 152.51

Compound 6m

9-[(1S,3R,4S)-3-(tert-butyldimethylsilyloxymethyl)-4-(biphenyl-4-formyloxy)-2-methylene-cyclopentyl]-6-chloro-9H-purine-2-carbamic acid tert-butyl ester

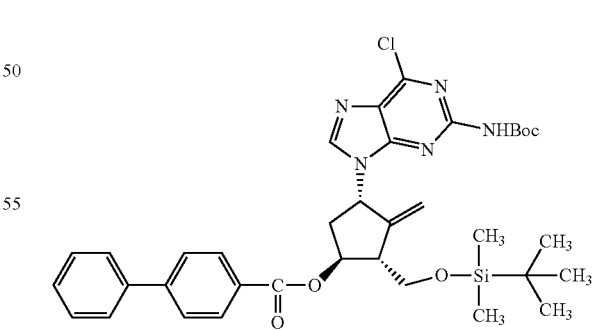

NMR (CDCl₃, 500 MHz)
¹HNMR: δ=0.14 (s, 6H), 0.95 (s, 9H), 1.54 (s, 9H), 2.63 (m, 1H), 3.02 (m, 1H), 3.99 (m, 1H), 4.14 (m, 1H), 4.91 (m, 1H), 5.33 (m, 1H), 5.60 (m, 1H), 5.84 (m, 1H), 7.71 (s, 11H);
¹³CNMR: δ=−5.13, 18.69, 26.26, 28.48, 38.92, 51.56, 56.83, 65.26, 76.68, 81.88, 112.13, 127.38, 127.53, 128.00, 128.49, 128.91, 129.21, 130.50, 140.18, 143.61, 146.25, 149.13, 150.44, 151.52, 152.60, 153.43, 166.15

Compound 6n: 9-[(1S,3R,4S)-3-(tert-butyldimethyl-silyloxymethyl)-4-benzoyloxy-2-methylene-cyclopentyl]-6-chloro-9H-purine-2-carbamic acid tert-butyl ester

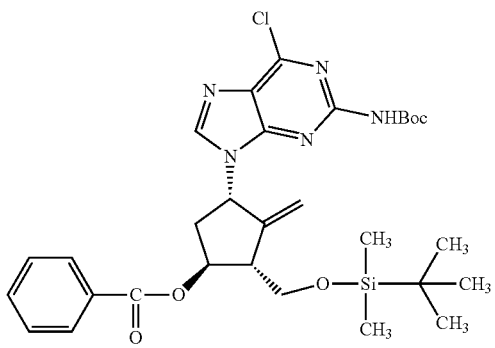 [SMILES: C=C1[C@H](CO[Si](C)(C)C(C)(C)C)[C@@H](OC(=O)c2ccccc2)C[C@@H]1n1cnc2c(Cl)nc(NC(=O)OC(C)(C)C)nc21]

NMR (CDCl$_3$, 500 MHz)

$^1$HNMR: δ=−0.05 (s, 6H), 0.75 (s, 9H), 1.34 (s, 9H), 2.47 (m, 2H), 2.84 (m, 1H), 3.82 (m, 1H), 3.92 (m, 1H), 4.73 (m, 1H), 5.15 (m, 1H), 5.42 (m, 1H), 5.66 (m, 1H), 7.58 (m, 6H), 7.98 (s, 1H);

$^{13}$CNMR: δ=−5.53, 18.28, 25.88, 28.09, 38.27, 51.22, 56.56, 64.80, 76.20, 81.22, 111.73, 127.61, 128.30, 129.56, 129.95, 133.07, 143.35, 148.71, 150.30, 151.00, 152.41, 153.03, 165.78

Compound 6o: (2R,4aR,6S,7aS)-6-chloro-9-(2-methyl-5-methylene-hexahydro-cyclopenta[1,3]dioxin-6-yl)-9H-purine-2-carbamic acid tert-butyl ester

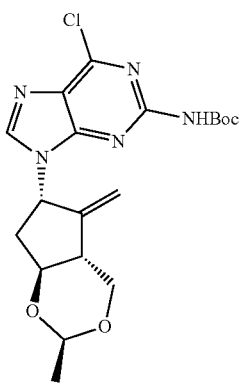 [SMILES: C=C1[C@@H]2CO[C@@H](C)O[C@H]2C[C@@H]1n1cnc2c(Cl)nc(NC(=O)OC(C)(C)C)nc21]

NMR (CDCl$_3$, 500 MHz)

$^1$HNMR: δ=1.41 (d, 3H), 1.52 (s, 9H), 2.33 (m, 1H), 2.46 (m, 2H), 3.93 (m, 1H), 4.44 (m, 1H), 4.56 (m, 2H), 4.88 (s, 1H), 5.00 (m, 1H), 5.50 (d, 1H), 7.65 (s, 1H), 7.94 (s, 1H);

$^{13}$CNMR: δ=20.84, 28.41, 36.69, 46.21, 54.33, 68.53, 79.28, 81.72, 99.99, 109.48, 128.21, 144.01, 145.69, 150.06, 151.51, 152.44, 152.49

Example 9

Preparation of 6-chloro-9-[(1S,3R,4S)-4-hydroxy-3-hydroxymethyl-2-methylene-cyclopentyl]-9H-purine-2-carbamic acid tert-butyl ester (Compound 7a; R═H, R'═Boc)

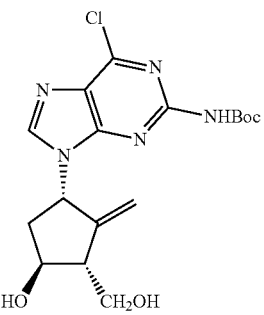

312 mg (0.5 mmol) Compound 6a (R$_1$═R$_2$═t-BuMe$_2$Si, R═H, R'═Boc) was dissolved in 10 ml THF, to which 780 mg TBAF (tetrabutylammonium fluoride) (3 mmol) was then added. The mixture was stirred at room temperature for 2 hours. TLC showed the dot of starting material disappeared. THF was evaporated off under reduced pressure. 30 ml EtOAc was added to the residue. The mixture was washed with water (20 ml×2) and saturated NaCl solution, dried with anhydrous Na$_2$SO$_4$, and filtered. The filtrate was evaporated to dryness under reduced pressure to give a gel which was then subjected to sucking filtration to afford 190 mg (96%) of title compound as solid.

$^1$HNMR (CDCl$_3$, 300 MHz): δ=1.53 (s, 9H), 2.29 (m, 1H), 2.66 (m, 1), 2.75 (m, 1H), 4.03 (dd, 2H, J=1.8, 3.3 Hz), 4.75 (m, 1H), 4.87 (s, 1H), 5.27 (s, 1H), 5.60 (t, 1H, J=8 Hz), 7.41 (s, 1H), 8.16 (s, 1H).

Example 10

Preparation of 6-chloro-9-[(1S,3R,4S)-4-hydroxy-3-hydroxymethyl-2-methylene-cyclopentyl]-9H-purine-2-carbamic acid tert-butyl ester (Compound 7a; R═H, R'═Boc)

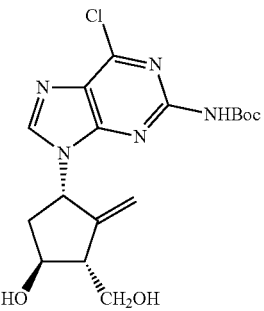

312 mg (0.5 mmol) Compound 6a (R$_1$═R$_2$═t-BuMe$_2$Si, R═H, R'═Boc) was dissolved in 10 ml THF, to which 3 ml methanol and hydrochloric acid (3 mmol) were successively added. The mixture was stirred at room temperature for 2 hours. TLC showed the dot of starting material disappeared. THF was evaporated off under reduced pressure. 30 ml EtOAc was added to the residue. The mixture was washed with water (20 ml×2) and saturated NaCl solution, dried with anhydrous $Na_2SO_4$, and filtered. The filtrate was evaporated to dryness under reduced pressure to give title compound as solid, yield: 95.7%.

$^1$HNMR (CDCl$_3$, 300 MHz): δ=1.53 (s, 9H), 2.29 (m, 1H), 2.66 (m, 1), 2.75 (m, 1H), 4.03 (dd, J=1.8, 3.3 Hz), 4.75 (m, 1H), 4.87 (s, 1H), 5.27 (s, 1H), 5.60 (t, 1H, J=8 Hz), 7.41 (s, 1H), 8.16 (s, 1H).

Example 11

Preparation of 6-chloro-9-[(1S,3R,4S)-4-hydroxy-3-hydroxymethyl-2-methylene-cyclopentyl]-N-(tert-butyloxycarbonyl)-9H-purine-2-carbamic acid tert-butyl ester [Compound 7d; R=Boc, R'=Boc]

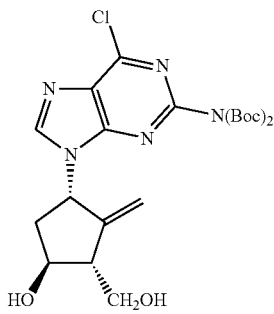

2.16 g (3 mmol) Compound 6d [$R_1$=$R_2$=t-BuMe$_2$Si, R=Boc, R'=Boc] was dissolved in 50 ml THF, to which 4.6 g TBAF (tetrabutylammonium fluoride) (17 mmol) was then added. The mixture was stirred at room temperature for 2 hours. TLC showed the dot of starting material disappeared. THF was evaporated off under reduced pressure. 100 ml EtOAc was added to the residue. The mixture was washed with water (70 ml×2) and saturated NaCl solution, dried with anhydrous $Na_2SO_4$, and filtered. The filtrate was evaporated to dryness under reduced pressure to give a gel which was then subjected to sucking filtration to afford 1.47 g (~100%) of title compound as solid.

$^1$HNMR (CDCl$_3$, 300 MHz): δ=1.43 (s, 18H), 2.34 (m, 1H), 2.61 (m, 1H), 2.77 (m, 1H), 3.90 (dd, 1H, J=5.4, 10.8 Hz), 4.01 (dd, 1H, J=4.5, 10.8 Hz), 4.58 (bs, 1H), 4.84 (s, 1H), 5.26 (s, 1H), 5.65 (t, 1H, J=8.1 Hz), 8.27 (s, 1H).

Example 12

According to the methods similar to Example 9, using Compounds 6b, 6c and 6e as starting materials, Compound 7b, 7c and 7e were prepared.

Compound 7b: 9-[(1S,3R,4S)-4-hydroxy-3-hydroxymethyl-2-methylene-cyclopentyl]-6-methoxy-9H-purine-2-carbamic acid tert-butyl ester

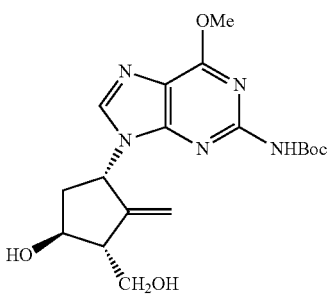 [SMILES: C=C1[C@H](CO)[C@@H](O)C[C@@H]1n1cnc2c(OC)nc(NC(=O)OC(C)(C)C)nc21]

$^1$HNMR (CDCl$_3$, 300 MHz): δ=1.53 (s, 9H), 2.25 (m, 1H), 2.26-2.80 (m, 2H), 3.39 (m, 1H), 4.0 (dd, 2H), 4.15 (s, 3H), 4.65 (m, 1H), 4.90 (s, 1H), 5.27 (s, 1H), 5.56 (t, 1H), 8.14 (s, 1H).

Compound 7c: 6-benzyloxy-9-[(1S,3R,4S)-4-hydroxy-3-hydroxymethyl-2-methylene-cyclopentyl]-9H-purine-2-carbamic acid tert-butyl ester

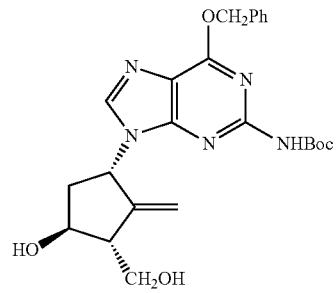

$^1$HNMR (CDCl$_3$, 300 MHz): δ=1.35 (s, 9H), 2.26 (m, 1H), 2.61-2.74 (m, 2H), 3.88 (dd, 1H), 3.93 (dd, 1H), 4.56 (bs, 1H), 4.80 (s, 1H), 5.21 (s, 1H), 5.60 (s, 2H), 7.29-7.35 (m, 3H), 7.48-7.50 (m, 2H), 8.05 (s, 1H).

Compound 7e: 6-tert-butyloxy-9-[(1S,3R,4S)-4-hydroxy-3-hydroxymethyl-2-methylene-cyclopentyl]-9H-purine-2-carbamic acid tert-butyl ester

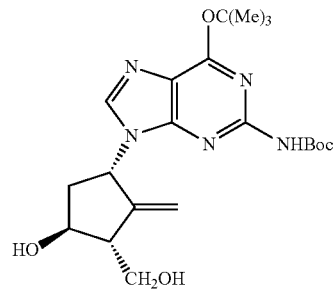

$^1$HNMR (CDCl$_3$, 300 MHz): δ=1.52 (s, 9H), 1.73 (s, 9H), 2.25 (m, 1H), 2.6-2.8 (m, 2H), 4.0 (d, J=6 Hz, 2H), 4.66 (bs, 1H), 4.83 (s, 1H) 5.29 (s, 1H), 5.45 (m, 1H), 7.83 (s, 1H).

Example 13

Preparation of 9-[(1S,3R,4S)-4-hydroxy-3-(tert-butyldimethylsilyloxymethyl)-2-methylene-cyclopentyl]-6-chloro-9H-purine-2-carbamic acid tert-butyl ester (Compound 8a)

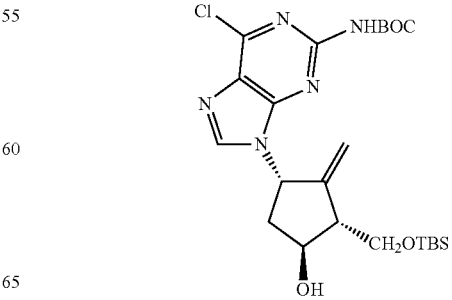

11 g of Compound 6m was dissolved in 155 ml anhydrous methanol, to which 2 g potassium carbonate was added. The reaction mixture was stirred until the starting material was consumed completely. The mixture was filtered and concentrated under reduced pressure. After work-up, Compound 8a was obtained, yield: 95%.

NMR (CDCl$_3$, 500 MHz):
$^1$HNMR: δ=0.07 (s, 6H), 0.86 (s, 9H), 1.50 (s, 9H), 2.28 (m, 1H), 2.43 (m, 1H), 2.71 (s, 1H), 3.81 (m, 1H), 3.95 (m, 1H), 4.47 (m, 1H), 4.79 (m, 1H), 5.11 (m, 1H), 5.87 (m, 1H), 7.4 (m, 1H), 7.82 (s, 1H); $^{13}$CNMR: δ=−5.29, 18.53, 26.13, 28.46, 53.36, 54.39, 56.00, 65.36, 73.42, 81.35, 111.15, 117.85, 140.88, 150.18, 150.94, 152.32, 153.45, 161.37

Example 14

Preparation of 9-[(1S,3R,4S)-4-tert-butyldimethylsilyloxy-3-hydroxymethyl-2-methylene-cyclopentyl]-6-chloro-9H-purine-2-carbamic acid tert-butyl ester (Compound 9a)

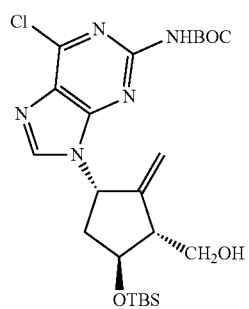

11 g of Compound 6j was dissolved in 155 ml anhydrous methanol, to which 2 g potassium carbonate was added. The reaction mixture was stirred until the starting material was consumed completely. The mixture was filtered and concentrated under reduced pressure. After work-up, Compound 9a was obtained, yield: 94%.

NMR (CDCl$_3$, 500 MHz):
$^1$HNMR: δ=0.03 (s, 6H), 0.83 (s, 9H), 1.45 (s, 9H), 2.10 (m, 1H), 2.55 (m, 1H), 2.62 (s, 1H), 3.89 (m, 2H), 4.00 (m, 1H), 4.53 (m, 1H), 4.70 (m, 1H), 5.14 (m, 1H), 5.43 (m, 1H), 7.38 (m, 1H), 7.84 (s, 1H); $^{13}$CNMR: δ=−4.66, 18.08, 25.90, 28.31, 54.36, 54.92, 58.26, 63.83, 73.76, 81.20, 111.33, 118.85, 141.99, 148.82, 150.72, 151.77, 152.04, 161.46

Example 15

Preparation of Compound 7a (Using Compound 8a as Starting Material)

9 g Compound 8a was dissolved in 100 ml THF. 25 g of tetrabutylammonium fluoride was added at room temperature and the reaction was maintained overnight. The reaction mixture was concentrated under reduced pressure to almost dryness. 100 ml ethyl acetate was added to dissolve the residue completely. The resulting solution was washed with 5% sodium chloride solution for 3 times, dried, and concentrated to dryness. After column chromatography, title compound was obtained as white solid, yield: 96%. $^1$H-NMR data of title compound obtained are the same as the data of Compound 7a obtained in Example 10.

Example 16

Preparation of Compound 7a (Using Compound 9a as Starting Material)

9 g Compound 9a was dissolved in 100 ml THF. 25 g of tetrabutylammonium fluoride was added at room temperature and the reaction was maintained overnight. The reaction mixture was concentrated under reduced pressure to almost dryness. 100 ml ethyl acetate was added to dissolve the residue completely. The resulting solution was washed with 5% sodium chloride solution for 3 times, dried, and concentrated to dryness. After column chromatography, title compound was obtained as white solid, yield: 95%. $^1$H-NMR data of title compound obtained are the same as the data of Compound 7a obtained in Example 10.

Example 17

Preparation of 2-amino-1,9-dihydro-9-[(1S,3R,4S)-4-hydroxy-3-(hydroxymethyl)-2-methylene-cyclopentyl]-6H-purine-6-one (Compound 1)

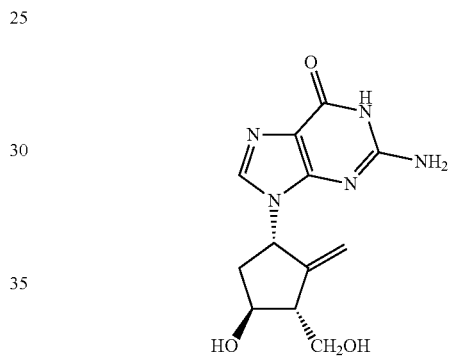

(1) Preparation of Compound 1 Using Compound 7a as Starting Material:

To 150 mg (0.38 mmol) Compound 7a (R=H, R'=Boc), 3 ml 2N HCl and 3 ml THF were added. The reaction mixture was heated to reflux with stirring for 6 hours. A portion of THF was evaporated off under reduced pressure. The remaining solution was adjusted to pH 7 with 2.5N NaOH, maintained standing at room temperature for 20 minutes, and then a crystal started to precipitate. The solution was maintained standing at room temperature overnight, and filtered. After being washed with a small amount of water, an off-white solid was obtained. Said solid was recrystallized from 2 ml water, to give 73 mg (69%) of colorless crystal.

(2) Preparation of Compound 1 Using Compound 7d as Starting Material:

To 1.2 g (2.42 mmol) Compound 7d (R=Boc, R'=Boc), 20 ml 2N HCl and 20 ml THF were added. The reaction mixture was heated to reflux with stirring for 8 hours. A portion of THF was evaporated off under reduced pressure. The remaining solution was extracted with 20 ml ethyl ether. The aqueous layer was adjusted to pH 7 with 2.5N NaOH, maintained standing at room temperature overnight, and filtered. After being washed with a small amount of water, an off-white solid was obtained. Said solid was recrystallized from 2 ml water, to give 360 mg (54%) of colorless crystal.

$^1$HNMR (d$^6$-DMSO, 300 MHz): δ=2.03 (m, 1H), 2.20 (m, 1H), 3.51 (t, 2H, J=6 Hz), 4.21 (bs, 1H), 4.54 (s, 1H), 4.80-

4.86 (m, 2H, exchangeable with D₂O), 5.08 (s, 1), 7.64 (s, 1H, broadened due to exchange with D₂O), 10.54 (s, 1H).

Example 18

Preparation of 2-amino-1,9-dihydro-9-[(1S,3R,4S)-4-hydroxy-3-(hydroxymethyl)-2-methylene-cyclopentyl]-6H-purine-6-one (Compound 1)

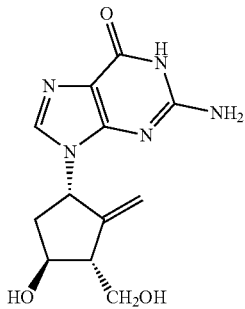 [SMILES: C=C1[C@H](CO)[C@@H](O)C[C@@H]1n1cnc2c(=O)[nH]c(N)nc21]

312 mg (0.5 mmol) Compound 6a (R₁=R₂=t-BuMe₂Si, R=H, R'=Boc) was dissolved in 15 ml tetrahydrofuran, to which 15 ml diluted hydrochloric acid was then added. The reaction mixture was heated with stirring until TLC showed the dot of starting material disappeared. Tetrahydrofuran was evaporated off under reduced pressure. 30 ml EtOAc was added to the residue. The aqueous phase was adjusted to neutral with an alkaline solution, cooled to precipitate crystal. The mixture was filtered. The resulting solid was recrystallized, and dried to give title compound as white solid, yield: 75%. The ¹H-NMR data of title compound obtained are the same as the data of Compound 1 in the Example 17.

Example 19

Preparation of Compound 1 (Using Compound 8a as Starting Material)

9 g Compound 8a was dissolved in 200 ml THF, to which 100 ml 2N HCl was added. The reaction mixture was heated to reflux until the reaction completed. The mixture was concentrated. The aqueous phase was adjusted to basic pH to precipitate crystal. The resulting solid was dried to give title compound as white solid, yield: 80%. The ¹H-NMR data of title compound obtained are the same as the data of Compound 1 in the Example 17.

Example 20

Preparation of Compound 1 (Using Compound 9a as Starting Material)

9 g Compound 9a was dissolved in 200 ml THF, to which 100 ml 2N HCl was added. The reaction mixture was heated to reflux until the reaction completed. The mixture was concentrated. The aqueous phase was adjusted to basic pH to precipitate crystal. The resulting solid was dried to give title compound as white solid, yield: 78%. The ¹H-NMR data of title compound obtained are the same as the data of Compound 1 in the Example 17.

Reference Examples

According to the method described in WO2004/052310A2, using intermediate compound 4 and 2-aminopurine compound in which the amino was unprotected as starting materials, Mitsunobu reaction was performed. The resulting compound was deprotected with TBAF, and then the compound obtained was hydrolyzed to give Entecavir. The reaction conditions in said reactions were substantially the same as the conditions used in the methods of the present invention, except using 2-aminopurine compound in which the amino was unprotected instead of 2-protected amino-6-substituted purine described in the methods of the present invention.

Reference Example 1

Preparation of 9-[(1S,3R,4S)-4-tert-butyldimethylsilyloxy-3-(tert-butyldimethylsilyloxymethyl)-2-methylene-cyclopentyl]-6-chloro-9H-purine-2-amine (Compound 24)

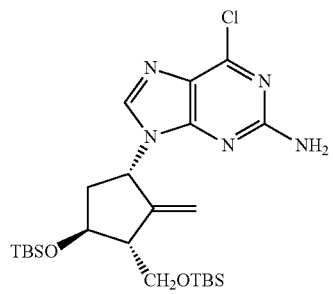

370 mg (1.0 mmol) (1R,3R,4S)-4-(tert-butyldimethylsilyloxy)-3-[(tert-butyldimethylsilyloxy)methyl]-2-methylene-cyclopentanol (Compound 4a, R₁=R₂=t-BuMe₂Si), 338 mg (2.0 mmol) 6-chloro-2-aminopurine (Compound 23) and 524 mg Ph₃P (2.0 mmol) were placed into 20 ml round bottom flask, to which 5 ml anhydrous THF was then added. The mixture was cooled to −23° C., to which a solution of 350 mg DEAD (1.0 mmol)/5 ml THF was added dropwise. After addition was completed, the reaction mixture was stirred at −23° C. for 3.5 hours, warmed to room temperature and stirred at room temperature overnight. Subsequently THF was evaporated off under reduced pressure. 10 ml t-BuOMe was added to the residue. The mixture was stirred for 5 minutes, to which 15 ml n-hexane was added. The mixture was maintained standing for 5 hours, and filtered to remove insoluble substance. The filtrate was purified with column chromatography, eluting with petroleum ether/EtOAc (3/1 (v/v)), to afford 305 mg (59%) of title compound as light yellow oil.

Reference Example 2

Preparation of 6-chloro-9-[(1S,3R,4S)-4-hydroxy-3-(hydroxymethyl)-2-methylene-cyclopentyl]-9H-purine-2-amine (Compound 25)

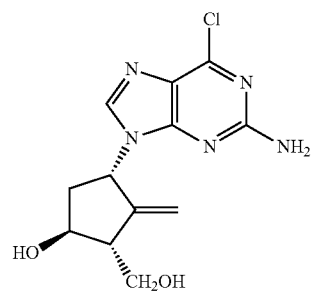

200 mg (0.38 mmol) Compound 24 was dissolved in 10 ml THF, to which 720 mg TBAF (tetrabutylammonium fluoride)

(6 mmol) was added. The mixture was stirred at room temperature for 1 hour. TLC showed the dot of starting material disappeared. THF was evaporated off under reduced pressure. 40 ml EtOAc was added to the residue. The mixture was successively washed with 20 ml water and saturated NaCl solution, dried with anhydrous Na$_2$SO$_4$, and filtered. The filtrate was evaporated to dryness under reduced pressure, to afford 52 mg (47%) of title compound as light yellow solid.

Reference Example 3

Preparation of 2-amino-1,9-dihydro-9-[(1S,3R,4S)-4-hydroxy-3-(hydroxymethyl)-2-methylene-cyclopentyl]-6H-purine-6-one (Compound 1)

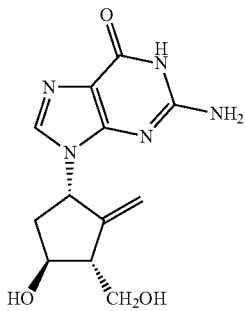 [SMILES: C=C1[C@H](CO)[C@@H](O)C[C@@H]1n1cnc2c(=O)[nH]c(N)nc21]

To 148 mg (0.5 mmol) of Compound 25, 5 ml 2N HCl and 5 ml THF were added. The mixture was heated to reflux with stirring for 6 hours. A portion of THF was evaporated off under reduced pressure. The remaining solution was adjusted to pH 7 with 2.5N NaOH solution, and maintained standing at room temperature for 20 minutes. A crystal started to precipitate. The mixture was maintained standing at room temperature overnight, and filtered. After being washed with a small amount of water, an off-white solid was obtained. Said solid was recrystallized from 2 ml water, to afford 85 mg (61%) of colorless crystal.

As described in above Reference Examples, Mitsunobu reaction was performed according to the method described in WO2004/052310A2, using intermediate compound 4 and 2-aminopurine compound in which the amino was unprotected as starting materials. The resulting compound was then deprotected with TBAF, followed by hydrolysis to afford Entecavir. The total yield of these three steps is only 17% (calculated on basis of the amount of intermediate compound 4).

In contrast, the Mitsunobu reaction described in the present invention is performed using intermediate compound 4 and 2-protected amino-6-substituted purine compound as starting materials, which can afford high yield (~100%), and the resulting product of said coupling reaction can simplify the purifications in subsequent reaction steps, thus the yields of subsequent reactions are also increased. Likewise based on the amount of intermediate compound 4, total yield of the three steps of the present invention is more than 52%. Therefore, the method of the present invention can simplify the preparation process and operations, significantly improve the yield and notably reduce the cost.

The invention claimed is:

1. A method for preparation of the compound of formula 1,

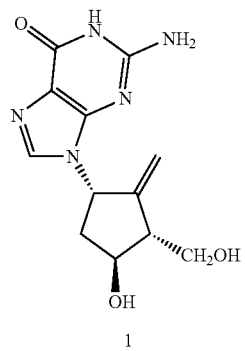 [SMILES: C=C1[C@H](CO)[C@@H](O)C[C@@H]1n1cnc2c(=O)[nH]c(N)nc21]

comprising the following steps:

reacting compound 4

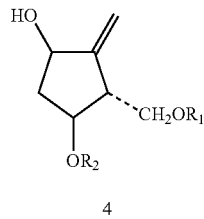

with 2-protected amino-6-substituted purine compound 5

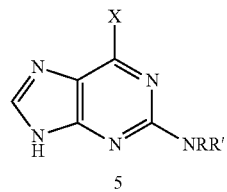

to give the coupling reaction product 6

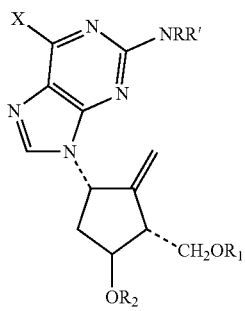

wherein

R₁ and R₂, which are the same or different, are independently selected from hydroxy-protecting groups of the following Groups (i) to (iii):

(i) R₁ and R₂, independent of each other, are selected from alkyl, halo-alkyl, benzyl, t-BuMe₂Si, t-BuPh₂Si, (i-Pr)₃Si or Et₃Si; or (ii) R₁ and R₂, independent of each other, are selected from t-BuMe₂Si, t-BuPh₂Si, benzoyl, tetrahydropyran-2-yl, benzoyl in which the phenyl ring bears substituent(s), and biphenyl-4-formyl, provided that R₁ and R₂ are not both t-BuMe₂Si;

R and R', which are the same or different, are independently selected from hydrogen, alkoxycarbonyl or aralkoxycarbonyl, provided that R and R' are not both hydrogen; X is halo, alkoxy, halo-alkoxy or aralkoxy;

Thereafter when R₁ and R₂ are both acyl protective groups or neither of them is acyl protective group, removing hydroxy-protecting groups from compound 6, to give compound 7

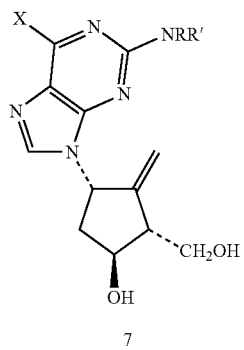

7 wherein X, R₁, R₂, R and R' are defined as above;

Thereafter hydrolysis of compound 7 to give the compound of formula 1

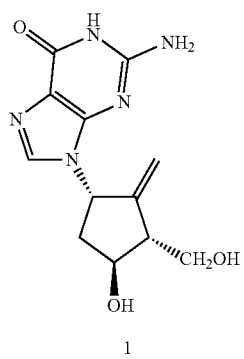 [SMILES: C=C1[C@H](CO)[C@@H](O)C[C@@H]1n1cnc2c(=O)[nH]c(N)nc21]

1 or when neither of R₁ and R₂ is acyl protective group, deprotecting compound 6 while hydrolysis in one-pot manner, to directly yield the compound of formula 1

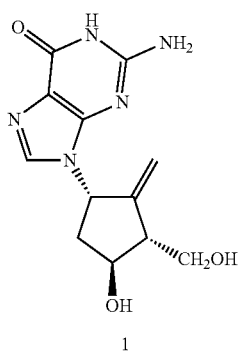 [SMILES: C=C1[C@H](CO)[C@@H](O)C[C@@H]1n1cnc2c(=O)[nH]c(N)nc21]

1 wherein X, R₁, R₂, R and R' are defined as above, or when one, but only one of R₁ and R₂ is acyl protective group, deprotecting compound 6 to give compound 8

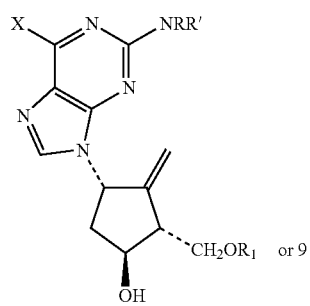

8 or 9

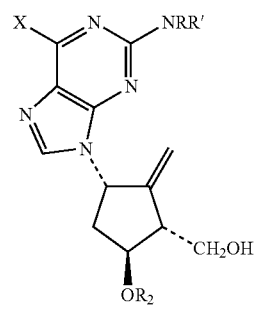

9 which is then hydrolyzed to give compound 1 or is converted to compound 7 followed by hydrolysis to give compound 1.

2. The method according to claim 1, wherein R₁ and R₂, which are the same or different, are independently selected from the group consisting of alkyl, halo-alkyl, benzyl, t-BuMe₂Si, t-BuPh₂Si, (i-Pr)₃Si or Et₃Si.

3. The method according to claim 1, wherein R₁ and R₂, which are the same or different, are independently selected from the group consisting of t-BuMe₂Si, t-BuPh₂Si, benzoyl, tetrahydropyran-2-yl, benzoyl in which the phenyl ring bears substituent(s), and biphenyl-4-formyl; provided that R₁ and R₂ are not both t-BuMe₂Si.

4. The method according to claim 1, wherein the reaction of compound 4 with 5 is performed in the presence of a Mitsunobu reaction reagent, in a non-protonic solvent.

5. The method according to claim 1, wherein deprotection of compound 6 is performed in the presence of an acid or a base or a quaternary ammonium salt containing fluorinion or potassium carbonate or an alkoxide.

6. The method according to claim 1, wherein, said hydrolysis of compound 7 is performed under acid or basic condition in water or in a mixture of water and organic solvents.

7. The method according to claim 1, wherein when neither of $R_1$ and $R_2$ is acyl protective group said deprotection and hydrolysis of compound 6 is performed in the presence of hydrohalogen acid, in an appropriate organic solvent or a mixture of said solvent and water.

8. The method according to claim 1, wherein when neither of $R_1$ and $R_2$ is acyl protective group, acyl protective groups are cleaved in the presence of a base.

9. The method according to claim 1, comprising the following steps:
reacting compound 4 with 2-protected amino-6-substituted purine compound 5 in the presence of $Ph_3P/EtO_2CN=NCO_2Et$ or $Ph_3P/i$-$PrO_2CN=NCO_2i$-Pr, in a non-protonic solvent, to give the coupling reaction product 6;
removing hydroxy-protecting groups from compound 6, in the presence of tetrabutylammonium fluoride (TBAF) or hydrochloric acid, to give compound 7;
hydrolysis of compound 7 in the presence of hydrochloric acid, in tetrahydrofuran, to give the compound of formula 1.

10. The method according to claim 1, wherein the compound of formula 6 is one wherein either both of $R_1$ and $R_2$ are acyl protective groups or neither is an acyl protective group.

11. The method according to claim 1, wherein the compound of formula 6 is one wherein neither of $R_1$ and $R_2$ is an acyl protecting group and compound of formula 6 is deprotected and hydrolized in one-pot manner.

12. The method according to claim 1, wherein the compound of formula 6 wherein either of $R_1$ or $R_2$ is an acyl protecting group.

13. The method according to claim 1, wherein the compound of formula 7 is hydrolyzed to produce the compound of formula 1.

14. A compound having the following formula:

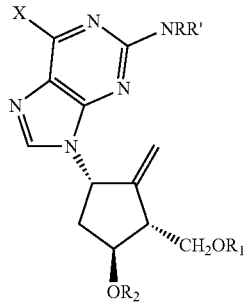

wherein
$R_1$ and $R_2$, which are the same or different, are independently selected from hydrogen or hydroxy-protecting groups of the following Groups (i) to (iii):
(i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si, or
(ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si; or (iii) $R_1$ and $R_2$ together with the five-member carbocycle to which they are attached form one of the following fused ring systems:

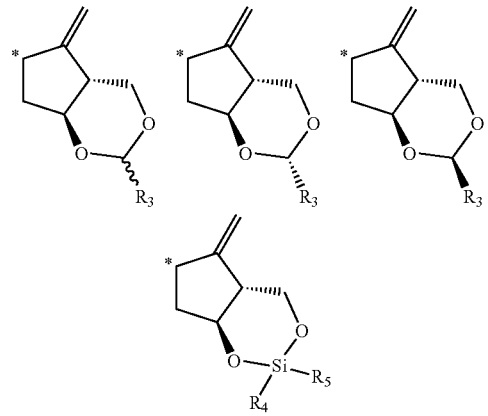

wherein $R_3$ is hydrogen atom, $C_{1-6}$ alkyl, phenyl or substituted phenyl in which the substituent on said phenyl is selected from methoxy, ethoxy, halo, phenyl and nitro; $R_4$ and $R_5$, which are the same or different, are independently selected from $C_{1-6}$ alkyl or aryl; wherein the symbol * represents the attachment point through which said fused ring is attached to the remaining moiety of the molecule;
R and R', which are the same or different, are independently selected from hydrogen, alkoxycarbonyl or aralkoxycarbonyl, provided that R and R' are not both hydrogen; X is halo, alkoxy, halo-alkoxy or aralkoxy.

15. The compound according to claim 14, wherein $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl; provided that $R_1$ and $R_2$ are not both t-BuMe$_2$Si.

16. A compound selected from:
9-[(1S,3R,4S)-4-tert-butyldimethylsilyloxy-3-(tert-butyldimethylsilyloxymethyl)-2-methylene-cyclopentyl]-6-chloro-9H-purine-2-carbamic acid tert-butyl ester;
9-[(1S,3R,4S)-4-tert-butyldimethylsilyloxy-3-(tert-butyldimethylsilyloxymethyl)-2-methylene-cyclopentyl]-6-chloro-N-(tert-butyloxycarbonyl)-9H-purine-2-carbamic acid tert-butyl ester;
9-[(1S,3R,4S)-4-tert-butyldimethylsilyloxy-3-(tert-butyldimethylsilyloxymethyl)-2-methylene-cyclopentyl]-6-methoxy-9H-purine-2-carbamic acid tert-butyl ester;
6-benzyloxy-9-[(1S,3R,4S)-4-tert-butyldimethylsilyloxy-3-(tert-butyldimethylsilyloxymethyl)-2-methylene-cyclopentyl]-9H-purine-2-carbamic acid tert-butyl ester;
6-tert-butyloxy-9-[(1S,3R,4S)-4-tert-butyldimethylsilyloxy-3-(tert-butyldimethylsilyloxymethyl)-2-methylene-cyclopentyl]-9H-purine-2-carbamic acid tert-butyl ester;
9-[(1S,3R,4S)-4-benzyloxy-3-(benzyloxymethyl)-2-methylene-cyclopentyl]-6-chloro-9H-purine-2-carbamic acid tert-butyl ester;
6-chloro-9-[(1S, 3R,4S)-4-hydroxy-3-hydroxymethyl-2-methylene-cyclopentyl]-9H-purine-2-carbamic acid tert-butyl ester;
6-chloro-9-[(1S,3R,4S)-4-hydroxy-3-hydroxymethyl-2-methylene-cyclopentyl]-N-(tert-butyloxycarbonyl)-9H-purine-2-carbamic acid tert-butyl ester;

9-[(1S,3R,4S)-4-hydroxy-3-hydroxymethyl-2-methylene-cyclopentyl]-6-methoxy-9H-purine-2-carbamic acid tert-butyl ester;
6-benzyloxy-9-[(1S,3R,4S)-4-hydroxy-3-hydroxymethyl-2-methylene-cyclopentyl]-9H-purine-2-carbamic acid tert-butyl ester;
6-tert-butyloxy-9-[(1S,3R,4S)-4-hydroxy-3-hydroxymethyl-2-methylene-cyclopentyl]-9H-purine-2-carbamic acid tert-butyl ester;
9-[(1S,3R,4S)-3-(tert-butyldimethylsilyloxymethyl)-4-(tetrahydropyran-2-yloxy)-2-methylene-cyclopentyl]-6-chloro-9H-purine-2-carbamic acid tert-butyl ester;
9-[(1S,3R,4S)-3-(tert-butyldimethylsilyloxymethyl)-4-(tert-butyldiphenylsilyloxy)-2-methylene-cyclopentyl]-6-chloro-9H-purine-2-carbamic acid tert-butyl ester;
9-[(1S,3R,4S)-3-(tert-butyldimethylsilyloxymethyl)-4-(biphenyl-4-formyloxy)-2-methylene-cyclopentyl]-6-chloro-9H-purine-2-carbamic acid tert-butyl ester;
9-[(1S,3R,4S)-3-(tert-butyldimethylsilyloxymethyl)-4-benzoyloxy-2-methylene-cyclopentyl]-6-chloro-9H-purine-2-carbamic acid tert-butyl ester;
9-[(1S,3R,4S)-3-(tert-butyldiphenylsilyloxymethyl)-4-(tetrahydropyran-2-yloxy)-2-methylene-cyclopentyl]-6-chloro-9H-purine-2-carbamic acid tert-butyl ester;
9-[(1S,3R,4S)-4-tert-butyldimethylsilyloxy-3-(tert-butyldiphenylsilyloxymethyl)-2-methylene-cyclopentyl]-6-chloro-9H-purine-2-carbamic acid tert-butyl ester;
9-[(1S,3R,4S)-4-(biphenyl-4-formyloxy)-3-(tert-butyldiphenylsilyloxymethyl)-2-methylene-cyclopentyl]-6-chloro-9H-purine-2-carbamic acid tert-butyl ester;
9-[(1S,3R,4S)-4-(tert-butyldiphenylsilyloxy)-3-(tert-butyldiphenylsilyloxymethyl)-2-methylene-cyclopentyl]-6-chloro-9H-purine-2-carbamic acid tert-butyl ester;
9-[(1S,3R,4S)-4-benzoyloxy-3-(tert-butyldiphenylsilyloxymethyl)-2-methylene-cyclopentyl]-6-chloro-9H-purine-2-carbamic acid tert-butyl ester;
9-[(1S,3R,4S)-4-benzoyloxy-3-(benzoyloxymethyl)-2-methylene-cyclopentyl]-6-chloro-9H-purine-2-carbamic acid tert-butyl ester;
9-[(1S,3R,4S)-4-(tetrahydropyran-2-yloxy)-3-(benzoyloxymethyl)-2-methylene-cyclopentyl]-6-chloro-9H-purine-2-carbamic acid tert-butyl ester;
9-[(1S,3R,4S)-4-tert-butyldimethylsilyloxy-3-(benzoyloxymethyl)-2-methylene-cyclopentyl]-6-chloro-9H-purine-2-carbamic acid tert-butyl ester;
9-[(1S,3R,4S)-4-(tert-butyldiphenylsilyloxy)-3-(benzoyloxymethyl)-2-methylene-cyclopentyl]-6-chloro-9H-purine-2-carbamic acid tert-butyl ester;
9-[(1S,3R,4S)-4-(biphenyl-4-formyloxy)-3-(benzoyloxymethyl)-2-methylene-cyclopentyl]-6-chloro-9H-purine-2-carbamic acid tert-butyl ester;
9-[(1S,3R,4S)-4-benzoyloxy-3-(biphenyl-4-formyloxymethyl)-2-methylene-cyclopentyl]-6-chloro-9H-purine-2-carbamic acid tert-butyl ester;
9-[(1S,3R,4S)-4-(tetrahydropyran-2-yloxy)-3-(biphenyl-4-formyloxymethyl)-2-methylene-cyclopentyl]-6-chloro-9H-purine-2-carbamic acid tert-butyl ester;
9-[(1S,3R,4S)-4-tert-butyldimethylsilyloxy-3-(biphenyl-4-formyloxymethyl)-2-methylene-cyclopentyl]-6-chloro-9H-purine-2-carbamic acid tert-butyl ester;
9-[(1S,3R,4S)-4-(tert-butyldiphenylsilyloxy)-3-(biphenyl-4-formyloxymethyl)-2-methylene-cyclopentyl]-6-chloro-9H-purine-2-carbamic acid tert-butyl ester;
9-[(1S,3R,4S)-4-(biphenyl-4-formyloxy)-3-(tetrahydropyran-2-yloxymethyl)-2-methylene-cyclopentyl]-6-chloro-9H-purine-2-carbamic acid tert-butyl ester;
9-[(1S,3R,4S)-4-tert-butyldimethylsilyloxy-3-(tetrahydropyran-2-yloxymethyl)-2-methylene-cyclopentyl]-6-chloro-9H-purine-2-carbamic acid tert-butyl ester;
9-[(1S,3R,4S)-4-(biphenyl-4-formyloxy)-3-(biphenyl-4-formyloxymethyl)-2-methylene-cyclopentyl]-6-chloro-9H-purine-2-carbamic acid tert-butyl ester;
(4aR,6S,7aS)-6-chloro-9-(2,2-di-tert-butyl-5-methylene-hexahydro-cyclopenta[1,3,2]dioxasilin-6-yl)-9H-purine-2-carbamic acid tert-butyl ester;
(2S,4aR,6S,7aS)-6-chloro-9-(2-methyl-5-methylene-hexahydro-cyclopenta[1,3]dioxin-6-yl)-9H-purine-2-carbamic acid tert-butyl ester;
(2R,4aR,6S,7aS)-6-chloro-9-(2-methyl-5-methylene-hexahydro-cyclopenta[1,3]dioxin-6-yl)-9H-purine-2-carbamic acid tert-butyl ester; or
(4aR,6S,7aS)-6-chloro-9-(2-methyl-5-methylene-hexahydro-cyclopenta[1,3]dioxin-6-yl)-9H-purine-2-carbamic acid tert-butyl ester.

17. A compound having the formula 4,

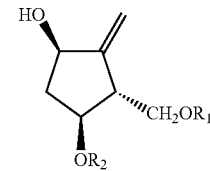

wherein
  $R_1$ and $R_2$, which are the same or different, are independently selected from hydroxy-protecting groups of the following Groups (i) to (iii):
  (i) $R_1$ and $R_2$, independent of each other, are selected from alkyl, halo-alkyl, benzyl, t-BuMe$_2$Si, t-BuPh$_2$Si, (i-Pr)$_3$Si or Et$_3$Si; or
  (ii) $R_1$ and $R_2$, independent of each other, are selected from t-BuMe$_2$Si, t-BuPh$_2$Si, benzoyl, tetrahydropyran-2-yl, benzoyl in which the phenyl ring bears substituent(s), and biphenyl-4-formyl, provided that $R_1$ and $R_2$ are not both t-BuMe$_2$Si;
  (iii) $R_1$ and $R_2$ together with the five-member carbocycle to which they are attached form one of the following fused ring systems:

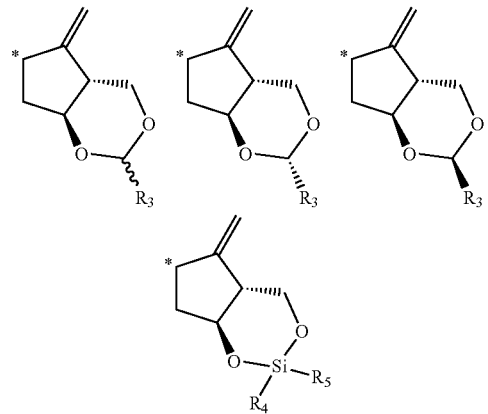

wherein $R_3$ is hydrogen atom, $C_{1-6}$ alkyl, phenyl or substituted phenyl in which the substituent on said phenyl is selected from methoxy, ethoxy, halo, phenyl and nitro;

R₄ and R₅, which are the same or different, are independently selected from $C_{1-6}$ alkyl or aryl; wherein the symbol * represents the attachment point through which said fused ring is attached to the remaining moiety of the molecule.

18. The compound according to claim 17, wherein $R_1$ and $R_2$, independent of each other, are selected from t-BuMe₂Si, t-BuPh₂Si, benzoyl, tetrahydropyran-2-yl, benzoyl in which the phenyl ring bears substituent(s), and biphenyl-4-formyl; provided that $R_1$ and $R_2$ are not both t-BuMe₂Si.

19. A compound selected from:
- (1R,3R,4S)-4-(tert-butyldimethylsilyloxy)-3-[(tert-butyldimethylsilyloxy)methyl]-2-methylene-cyclopentanol;
- (1R,3R,4S)-4-benzyloxy-3-(benzyloxymethyl)-2-methylene-cyclopentanol;
- (1R,3R,4S)-4-(tertahydropyran-2-yloxy)-3-(tert-butyldimethylsilyloxymethyl)-2-methylene-1-cyclopentanol;
- (1R,3R,4S)-4-(tert-butyldiphenylsilyloxy)-3-(tert-butyldimethylsilyloxymethyl)-2-methylene-1-cyclopentanol;
- (1R,3R,4S)-4-(biphenyl-4-formyloxy)-3-(tert-butyldimethylsilyloxymethyl)-2-methylene-1-cyclopentanol;
- (1R,3R,4S)-4-benzoyloxy-3-(tert-butyldimethylsilyloxymethyl)-2-methylene-1-cyclopentanol;
- (1R,3R,4S)-4-(tetrahydropyran-2-yloxy)-3-(tert-butyldiphenylsilyloxymethyl)-2-methylene-1-cyclopentanol;
- (1R,3R,4S)-4-tert-butyldimethylsilyloxy-3-(tert-butyldiphenylsilyloxymethyl)-2-methylene-1-cyclopentanol;
- (1R,3R,4S)-4-(biphenyl-4-formyloxy)-3-(tert-butyldiphenylsilyloxymethyl)-2-methylene-1-cyclopentanol;
- (1R,3R,4S)-4-(tert-butyldiphenylsilyloxy)-3-(tert-butyldiphenylsilyloxymethyl)-2-methylene-1-cyclopentanol;
- (1R,3R,4S)-4-benzoyloxy-3-(tert-butyldiphenylsilyloxymethyl)-2-methylene-1-cyclopentanol;
- (1R,3R,4S)-4-benzoyloxy-3-(benzoyloxymethyl)-2-methylene-1-cyclopentanol;
- (1R,3R,4S)-4-(tetrahydropyran-2-yloxy)-3-(benzoyloxymethyl)-2-methylene-1-cyclopentanol;
- (1R,3R,4S)-4-tert-butyldimethylsilyloxy-3-(benzoyloxymethyl)-2-methylene-1-cyclopentanol;
- (1R,3R,4S)-4-(tert-butyldiphenylsilyloxy)-3-(benzoyloxymethyl)-2-methylene-1-cyclopentanol;
- (1R,3R,4S)-4-(biphenyl-4-formyloxy)-3-(benzoyloxymethyl)-2-methylene-1-cyclopentanol;
- (1R,3R,4S)-4-benzoyloxy-3-(biphenyl-4-formyloxymethyl)-2-methylene-1-cyclopentanol;
- (1R,3R,4S)-4-(tetrahydropyran-2-yloxy)-3-(biphenyl-4-formyloxymethyl)-2-methylene-1-cyclopentanol;
- (1R,3R,4S)-4-tert-butyldimethylsilyloxy-3-(biphenyl-4-formyloxymethyl)-2-methylene-1-cyclopentanol;
- (1R,3R,4S)-4-(tert-butyldiphenylsilyloxy)-3-(biphenyl-4-formyloxymethyl)-2-methylene-1-cyclopentanol;
- (1R,3R,4S)-4-(biphenyl-4-formyloxy)-3-(tetrahydropyran-2-yloxymethyl)-2-methylene-1-cyclopentanol;
- (1R,3R,4S)-4-tert-butyldimethylsilyloxy-3-(tetrahydropyran-2-yloxymethyl)-2-methylene-1-cyclopentanol;
- (1R,3R,4S)-4-(biphenyl-4-formyloxy)-3-(biphenyl-4-formyloxymethyl)-2-methylene-1-cyclopentanol;
- (4aR,6R,7aS)-2,2-di-tert-butyl-5-methylene-6-hydroxy-6H-hexahydro-cyclopenta[d][1,3,2]dioxasiline;
- (2S,4aR,6S,7aS)-2-methyl-5-methylene-6-hydroxy-6H-tetrahydro-cyclopenta[1,3]dioxane;
- (2R,4aR,6S,7aS)-2-methyl-5-methylene-6-hydroxy-6H-tetrahydro-cyclopenta[1,3]dioxane; or
- (4aR,6S,7aS)-2-methyl-5-methylene-6-hydroxy-6H-tetrahydro-cyclopenta[1,3]dioxane.

20. The method according to claim 1 wherein X is selected from the group consisting of halo, C1-6-alkoxy, halo-C1-C6 alkoxy, or C5-C10-aralkoxy.

21. The method according to claim 1 wherein R and R' are each independently selected from hydrogen and tert-butoxycarbonyl, provided that R and R' are not both hydrogen.

22. The method according to claim 1 wherein the reaction of compound 4 with 5 is performed in the presence of Ph3P/EtO2CN=NCO2Et or Ph3P/i-PrO2CN=NCO2-iPr, in a non-protonic solvent selected from the group consisting of aromatic hydrocarbons, halogenated aromatic hydrocarbons, halogenated hydrocarbons or ethers.

23. The method according to claim 1 wherein deprotection of compound 6 is effected in presence of a reagent selected from the group consisting of hydrochloric acid or hydrogen fluoride, formic acid tetra-butylammonium fluoride (TBAF).

24. The method according to claim 1 wherein one step deprotection and hydrolysis of compound 6 is effected by dilute hydrochloric acid in an organic solvent or mixture of organic solvent with water.

25. The method according to claim 1 wherein X is $C_{1-6}$ alkoxy, halo-$C_{1-6}$ alkoxy or $C_{5-10}$ aralkoxy.

26. The compound as claimed in claim 14 wherein R and R' are each independently selected from the group consisting of $C_{1-6}$ alkoxycarbonyl and $C_{5-10}$ aralkoxycarbonyl.

27. A compound according to claim 17 wherein $R_4$ and $R_5$, which are the same or different, are independently selected from tert-butyl or phenyl.

* * * * *